(12) United States Patent
DeMarco et al.

(10) Patent No.: US 9,073,973 B2
(45) Date of Patent: Jul. 7, 2015

(54) DYE CONJUGATES OF TEMPLATE-FIXED PEPTIDOMIMETICS

(75) Inventors: Steven J. DeMarco, Dietgen (CH); Frank Gombert, Hultingen (DE); Daniel Obrecht, Battwil (CH); Christian Ludin, Aesch (CH); Barbara Romagnoli, St. Louis (FR)

(73) Assignees: Polyphor LTD., Allschwil (CH); Universitat Zurich, Zurich (CH)

( * ) Notice: Subject to any disclaimer, the term of this patent is extended or adjusted under 35 U.S.C. 154(b) by 1529 days.

(21) Appl. No.: 11/913,511

(22) PCT Filed: May 2, 2005

(86) PCT No.: PCT/EP2005/004751
§ 371 (c)(1),
(2), (4) Date: Jul. 30, 2009

(87) PCT Pub. No.: WO2006/117011
PCT Pub. Date: Nov. 9, 2006

(65) Prior Publication Data
US 2011/0135576 A1   Jun. 9, 2011

(51) Int. Cl.
A61K 38/10 (2006.01)
C07K 5/00 (2006.01)
C07K 7/64 (2006.01)
A61K 38/48 (2006.01)

(52) U.S. Cl.
CPC ............. C07K 7/64 (2013.01); A61K 38/4886 (2013.01)

(58) Field of Classification Search
CPC ....... C07K 14/705; C07K 16/30; A61K 38/10
See application file for complete search history.

(56) References Cited

FOREIGN PATENT DOCUMENTS

| WO | WO2004096840 A1 | * | 4/2004 | ............... C07K 7/64 |
| WO | WO 2004/096839 A1 | | 11/2004 | |
| WO | WO2004/096840 | * | 11/2004 | |
| WO | WO 2004/096840 A1 | | 11/2004 | |
| WO | WO 2004096840 A1 | * | 11/2004 | |

OTHER PUBLICATIONS

Cabrera et. al. (Anti-Human Immunodeficiency Virus Activity of Novel Aminoglycoside-Arginine Conjugates at Early Stages of Infection, Aids Research and Human Retroviruses vol. 16, No. 7, p. 627-634, 2000.*
Brinkley (A Brief Summary of Methods for Preparing protein Conjugates with Dyes, Haptens, and Cross-linking Reagents, Bioconjugate Chem. vol. 3, p. 2-13, 1992.*
Hendrix et. al. (Pharmacokinetics and Safety of AMD-3100 a Novel Antagonist of the CXCR4 Chemokine Receptor, in Human Volunteers, Antimicrobial Agents and Chemotherapy 44(6):1667, 2000).*
Brinkley, Michael, A Brief Summary of Methods for Preparing protein Conjugates with Dyes, Haptens, and Cross-linking Reagents, Bioconjugate Chem. vol. 3, p. 2-13, 1992.*
Licha, K., et al., "New Contrast Agents for Optical Imaging: Acid-Cleavable Conjugates of Cyanine Dyes with Biomolecules", SPIE vol. 3600, pp. 29-25, (1999).
Sheehan, J., et al., "A New Method of Forming Peptide Bonds", J. Am. Chem. Soc., vol. 77, pp. 1067-1068, (1955).
Sarantakis, D., et al., "A Novel Cyclic Undecapeptide, WY-40, 770, with Prolonged Growth Hormone Release Inhibiting Activity", Biochemical Biophysical Research Communnications, vol. 73, No. 2, pp. 336-342, (1976).
König, W. et al., "Eine Neue Methode zur Synthese von Peptiden: Aktivierung der Carboxylgruppe mit Dicyclohexylcarbodiimid unter Zusatz von 1-Hydroxy-benzotriazolen", Chem. Ber., vol. 103, pp. 788-798, (1970).
Castro, B., et al., "Reactifs de Couplage Peptidique IV (1)—L'Hexafluorophosphate de Benzotriazolyl N-Oxytrisoimethylamio Phosphonium", Tetrahedron Lett., No. 14, pp. 1219-1222, (1975).
Coste, J., et al., "PyBOP®: A New Peptide Coupling Reagent Devoid of Toxic By-Product", Tetrahedron Lett., vol. 31, No. 2, pp. 205-208, (1990).
Knorr, R., et al., "New Coupling Reagents in Peptide Chemistry", Tetrahedron Lett., vol. 30, No. 15, pp. 1927-1930, (1989).

(Continued)

*Primary Examiner* — James H Alstrum Acevedo
*Assistant Examiner* — Jeanette Lieb
(74) *Attorney, Agent, or Firm* — Hoffmann & Baron, LLP

(57) ABSTRACT

Dye conjugates of template-fixed β-hairpin peptidomimetics of the general formula (I) wherein Z is a template-fixed chain of 14 α-amino acid residues which, depending on their positions in the chain (counted starting from the N-terminal amino acid), are Gly, or Pro or of certain types which, as the remaining symbols in the above formula, are defined in the description and the claims, and salts thereof, have CXCR4 antagonizing properties, and are useful for cancer therapy; diagnostic imaging; for detection of tumors and other abnormalities; for photoacoustic tumor imaging, detection and therapy; and for sonofluorescence tumor imaging, detection and therapy. The various dyes forming part of these conjugates are useful over the range of 300-1200 nm, the exact range being dependent upon the particular dye. These dye conjugates of β-hairpin peptidomimetic can be manufactured by processes which are based on a mixed solid- and solution phase synthetic strategy.

(I)

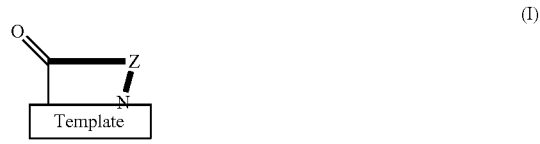

11 Claims, 1 Drawing Sheet

(56) References Cited

OTHER PUBLICATIONS

Carpino, L., et al., "Racemization Studies during Solid-Phase Peptide Synthesis using Azabenzotriazole-based Coupling Reagents", Tetrahedron Lett., vol. 35, No. 15, pp. 2279-2282, (1994).

Kaiser, E., et al., "Color Test for Detection of Free Terminal Amino Groups in the Solid-Phase Synthesis of Peptides", Anal. Biochemistry, vol. 34, pp. 595-589, (1970).

Meienhofer, J., et al., "Solid Phase Synthesis without Repetitive Acidolysis", Int. J. Peptide Protein Res., vol. 13, pp. 35-42, (1979).

Oberlin, E., et al., "The CXC chemokine SDF-1 is the ligand for LESTR/fusin and prevents infection by T-cell-lineadapted HIV-1", Nature, vol. 382, pp. 833-835, (1996).

Loetscher, M., et al., "Cloning of a Human Seven-transmembrane Domain Receptor, LESTR, that is Highly Expressed in Leukocytes", J. Biol. Chem., vol. 269, No. 1, pp. 232-237, (1994).

D'Apuzzo, M., et al., "The chemokine SDF-1, stromal cell-derived factor 1, attracts early stage B cell precursors via the chemokine receptor CXCR4", Eur. J. Immunol., vol. 27, pp. 1788-1793, (1997).

Mosmann, T., "Rapid Colorimetric Assay for Cellular Growth and Survival: Application to Proliferation and Cytotoxicity Assays", Journal of Immunological Methods, vol. 65, pp. 55-63, (1983).

Berridge, M.V., et al., "Characterization of the Cellular Reduction of 3-(4,5-dimethylthiazol-2-yl)-2,5-diphenyltetrazolium bromide (MMT): Subcellular Localization, Substrate Dependence, and Involvement of Mitochondrial Electron Transport in Mtt Reduction", Arch. Biochem. Biophys., vol. 303, No. 2, pp. 474-482, (1993).

Fantini, S., et al., "Assessment of the size, position, and optical properties of breast tumors in vivo by noninvasive optical methods", Applied Optics, vol. 37, No. 10, pp. 1982-1989, (1998).

Shaw, D., "Contrast Media Directions for the 1990's", Investigative Radiology, vol. 28, Supplement 3, pp. S138-S139, (1993).

Kwekkeboom, D.J., et al., "Somatostatin receptor imaging in patients with sarcoidosis", European Journal of Nuclear Medicine, vol. 25, No. 9, pp. 1284-1292, (1998).

Levy, J.A., "Infection by Human Immunodeficiency Virus—CD4 is Not Enough", New England J. Med., vol. 335, No. 20, 1528-1530, (1996).

Müller, A., et al., "Involvement of chemokine receptors in breast cancer metastasis", Nature, vol. 410, pp. 50-56, (2001).

Hall, J.M., et al., "Stromal Cell-Derived Factor 1, a Novel Target of Estrogen Receptor Action, Mediates the Mitogenic Effects of Estradiol in Ovarian and Breast Cancer Cells", Molecular Endocrinology, vol. 17, No. 5, pp. 792-803 (2003).

Bertolini, F., et al., "CXCR4 Neutralization, a Novel Therapeutic Approach for Non-Hodgkin's Lymphoma", Cancer Research, vol. 62, pp. 3106-3112, (2002).

Kijima, T., et al., "Regulation of Cellular Proliferation, Cytoskeletal Function, and Signal Transduction through CXCR4 and c-Kit in Small Cell Lung Cancer Cells", Cancer Research, vol. 62, pp. 6304-6311, (2002).

Tamamura, H., et al., "T140 analogs as CXCR4 antagonists identified as anti-metastatic agents in the treatment of breast cancer", FEBS Letters, vol. 550, pp. 79-83, (2003).

Rubin, J.B., et al., "A small-molecule antagonist of CXCR4 inhibits intracranial growth of primary brain tumors", PNAS, vol. 100, No. 23, 13513-13518, (2003).

Barbero, S., et al., "Stromal Cell-derived Factor 1α Stimulates Human Glioblastoma Cell Growth through the Activation of Both Extracellular Signal-regulated Kinases 112 and Akt", Cancer Research, vol. 63, pp. 1969-1974, (2003).

Schimanski, C.C., et al., "Effect of Chemokine Receptors CXCR4 and CCR7 on the Metastatic Behavior of Human Colorectal Cancer", Clinical Cancer Research, vol. 11, pp. 1743-1750, (2005).

Arya, M., et al., "The importance of the CXCL12—CXCR4 chemokine ligand—receptor interaction in prostate cancer metastasis", Journal of Experimental Therapeutics and Oncology, vol. 4, pp. 291-303, (2004).

Scala, S., et al., "Expression of CXCR4 Predicts Poor Prognosis in Patients with Malignant Melanoma", Clinical Cancer Research, vol. 11, pp. 1835-1841, (2005).

Chen, X., et al., "Tannic Acid Is an Inhibitor of CXCL12 (SDF-1α)/CXCR4 with Antiangiogenic Activity", Clinical Cancer Research, vol. 9, pp. 3115-3123, (2003).

Salcedo, R., et al., "Role of Chemokines in Angiogenesis: CXCL 12/SDF-1 and CXCR4 Interaction, a Key Regulator of Endothelial Cell Responses", Microcirculation, vol. 10, pp. 359-370, (2003).

Obrecht, D., et al., "Novel Peptide Mimetic Building Blocks and Strategies for Efficient Lead Finding", Advances of Medicinal Chemistry, vol. 4, pp. 1-68, (1999).

Robinson, J.A., "The Design, Synthesis and Conformation of Some New 6-Hairpin Mimetics: Novel Reagents for Drug and Vaccine Discovery", Synlett, No. 4, pp. 429-441, (1999).

Jiang, L., et al., "Combinatorial Biomimetic Chemistry: Parallel Synthesis of a Small Library of 3-Hairpin Mimetics Based on Loop III from Human Platelet-Derived Growth Factor B", Helvetica Chimica Acta, vol. 83, pp. 3097-3112, (2000).

Venkatachalam, C.M., "Stereochemical Criteria for Polypeptides and Proteins. V. Conformation of a System of Three Linked Peptide Units", Biopolymers, vol. 6, pp. 1425-1434, (1968).

Kabsch, W., et al., "Dictionary of Protein Secondary Structure: Pattern Recognition of Hydrogen-Bonded and Geometrical Features", Biopolymers, vol. 22, pp. 2577-2637, (1983).

Balaram, P., "Non-standard amino acids in peptide design and protein engineering", Current Opinion on Structural Biology, vol. 2, pp. 845-851, (1992).

Crisma, M., et al., "β-Turn Conformations in Crystal Structures of Model Peptides Containing α,α-Di-n-Propylglycine and α,α-Di-n-Butylglycine", Biopolymers, vol. 35, pp. 1-9, (1995).

Hruby, V.J., et al., "Emerging approaches in the molecular design of receptor-selective peptide ligands: conformational, topographical and synamic considerations", Biochem. J. col. 268, pp. 249-262, (1990).

Obrecht, D. et al., . "129. A New General Approach to Enantiomerically Pure Cyclic and Open-Chain (R)- and (S)-α,α-Disubstituted α-Amino Acids", Helvetuca Chimica Acta, vol. 75, pp. 1666-1696, (1992).

Obrecht, D., et al., "A Novel Synthehsis of (R)- and (S)-α-Alkylated Aspartic and Glutamic Acids: α-Alkylated Aspartic Succinimides as New Type of β-Turn Type II and II' Mimetics", Tetrahedron, vol. 51, No. 40, pp. 10883-10900, (1995).

Obrecht, D., et al., "119. Novel Open-Chain and Cyclic Conformationally Constrained (R)- and (S)-α,α-Disubstituted Tyrosine Analogues", Helvetica Chimica Acta, vol. 78, pp. 1567-1587, (1995).

Obrecht, D., et al., "44. L-Phenylalanine Cyclohexylamide: A Simple and Convenient Auxiliary for the Synthesis of Optically Pure α,α-Disubstituted (R)- and (S)-Amino Acids", Helvetica Chimica Acta, vol. 78, pp. 563-580, (1995).

Obrecht, D., et al., "56. An Efficient Synthesis of Optically Pure (R)- and (S)-2-(Aminomethyl)alanine ((R)-and (S)-Ama) and (R)- and (S)-2-(Aminomethyl)leucine ((R)- and (5)-Aml)", Helvetica Chimica Acta, vol. 78, pp. 703-714, (1995).

van Lier, J., et al., "Photosensitizing Compounds: Their Chemistry, Biology and Clinical Use", Ciba Foundation Symposium 146, pp. 17-32, (1989).

Giulio, J., "Far-red-absorbing photosensitizers: their use in the photodynamic therapy of tumors", J. Photochem. Photobiol. A: Chem., vol. 62, pp. 371-378, (1992).

Patonay, G., et al., "Near-Infrared Fluorogenic Labels: New Approach to an Old Problem", Analytical Chemistry, vol. 63, No. 6, pp. 321A-327A, (1991).

Giulio, J., et al., "Second Generation Photosensitizers for the Photodynamic Therapy of Tumours", Light in Biology and Medicine, vol. 2, pp. 253-266, (1991).

Tam, J.P., et al., "Improved Synthesis of 4-(Boc-aminoacyloxymethyl)-phenylacetic Acids for use in Solid Phase Peptide Synthesis", Communications, pp. 955-957, (1979).

Ahmed, A.K, et al., "Nonenzymic Reactivation of Reduced Bovine Pancreatic Ribonuclease by Air Oxidation and by Glutathione

(56) References Cited

OTHER PUBLICATIONS

Oxidoreduction Buffers", The Journal of Biological Chemistry,., vol. 250, No. 21, pp. 8477-8482, (1975).

Pennington, M.W., et al., "Comparison of folding procedures on synthetic-conotoxin", Peptide Chemistry, pp. 164-166, (1990).

Rink, H., "Solid-Phase Synthesis of Protected Peptide Fragments using a Trialkoxy-Diphenyl-Methylester Resin", Tetrahedron Letters, vol. 28, No. 33, pp. 3783-3790, (1987).

Fields, G.B., et al., "Solvation Effects in Solid-Phase Peptide Synthesis", J. Am. Chem. Soc., 113, pp. 4202-4207, (1991).

Mergler,M., et al., "Peptide Synthesis by a Combination of Solid-Phase and Solution Methods I: A New Very Acid-Labile Anchor Group for the Solid Phase Synthesis of Fully Protected Fragments", Tetrahedron Letters, vol. 29, No. 32, pp. 4005-4008, (1988).

Flersheimer & Riniker, "Solid-phase synthesis of peptides with the highly acid-sensitive HMPB linker", Peptides, 1990, pp. 131-133, (1991).

Barlos, K., et al., "Darstellung Geschutzter Peptid-Fragmente Unter Einsatz Substituierter Triphenylmethyl-Harze", Tetrahedron Letters, Vol, 30, No. 30, pp. 3943-3946, (1989).

Hnatowich, D.J., et al., "Radioacitve Labeling of Antibody: A Simple and Efficient Method", Science, vol. 220, No. 4597, pp. 613-615, (1983).

Pelegrin, A., et al., "Photoimmunodiagnosis with antibody-fluorescein conjugates: in vitro and in vivo preclinical studies", Journal of Cellular Pharmacology, vol. 3, pp. 141-145, (1992).

* cited by examiner

DYE CONJUGATES OF TEMPLATE-FIXED PEPTIDOMIMETICS

CROSS-REFERENCE TO RELATED APPLICATIONS

This application is the National Stage of International Application No. PCT/EP2005/004751, filed May 2, 2005, the contents of which are incorporated by reference herein.

FIELD OF THE INVENTION

The present invention provides dye conjugates of template-fixed β-hairpin peptidomimetics incorporating a template-fixed chain of 14 α-amino acid residues which, depending on their positions in the chain, are Gly, Pro, or of certain types, as defined hereinbelow. These dye conjugates of template-fixed β-hairpin mimetics have CXCR4 antagonizing activity and are useful for therapy and diagnostic imaging; for detection of tumors and other abnormalities; for photoacoustic tumor imaging, detection and therapy; for sonofluorescence tumor imaging, detection and therapy; and for photodynamic therapy. They show improved efficacy, bioavailability, half-life and most importantly a significantly enhanced ratio between CXCR4 antagonizing activity and selectivity leading to enhanced localization in tumors on the one hand, and low cytotoxicity on the other.

In addition, the present invention provides efficient synthetic processes by which these compounds can, if desired, be made in parallel library-format.

BACKGROUND OF THE INVENTION

The use of visible and near infrared (NIR) light in clinical practice is rapidly growing (Fanini S et al, *Appl. Opt.* 1998, 37, 1982-1989).

Compounds absorbing or emitting in the visible, or NIR, or long wave region of the electromagnetic spectrum are potentially useful for optical tomographic imaging, or endoscopic visualization.

Common methods for cancer diagnosis rely on the physical detection of a palpable tumor mass or the use of different forms of roentgenography, scintigraphy, ultrasound and imaging techniques for tissue imaging which require the presence of a significant tumor mass (Shaw M L et al, *Invest. Radiol.* 1993, 28, 138-139).

Large molecules such as antibodies have, for scintigraphic imaging, the disadvantage that they are preferably taken up by the liver and can elicit adverse immunogenic reactions in humans (Guyton, A C, textbook of medical physiology. Philadelphia, Pa., W.B. Saunders CO 1996). Recent studies have demonstrated that attachment of chelating agents to small-molecular peptides can be used to target tumors without loss of receptor affinity (Kweckenboom D J et al, *Eur. J. Nucl. Med.* 1998, 25, 1284-1292).

Such advantages include enhanced localization in tumors, and rapid clearance from the blood.

Recently, it has been shown that the CXCR4-receptor is not only involved in the entry of HIV (N. Levy, *Engl. J. Med.*, 335, 29, 1528-1530) but also in the chemotactic activity of cancer cells, such as breast cancer metastasis or metastasis of ovarian cancer (A. Muller, B. Homey, H. Soto, N. Ge, D. Catron, M. E. Buchanan, T. Mc Clanahan, E. Murphey, W. Yuan, S. N. Wagner, J. Luis Barrera, A. Mohar, E. Verastegui, A. Zlotnik, *Nature* 2001, 50, 410, J. M. Hall, K. S. Korach, Molecular Endocrinology, 2003, 1-47); non-Hodgin's Lymphoma (F. Bertolini, C. DellÀgnola, P. Manusco, C. Rabascio, A. Burlini, S. Monestiroli, A. Gobbi, G. Pruneri, G. Martinelli, *Cancer Research* 2002, 62, 3106-3112); lung cancer (T. Kijima, G. Maulik, P. C. Ma, E. V. Tibaldi, R:E. Turner, B. Rollins, M. Sattler, B. E. Johnson, R. Salgia, *Cancer Research* 2002, 62, 6304-6311); melanoma; prostate cancer; kidney cancer; neuroblastomia; pancreatic cancer; multiple myeloma; or chronic lymphocytic leukemia (H. Tamamura et al. *Febs Letters* 2003, 550 79-83). Blocking the chemotactic activity with a CXCR4 inhibitor should stop the migration of cancer cells.

The CXCR4 receptor has also been implicated in the growth and proliferation of tumors. It was shown that activation of the CXCR4 receptor was critical for the growth of both malignant neuronal and glial tumors, and small-cell lung tumors. Moreover, systemic administration of the CXCR4 antagonist AMD3100 inhibits growth of intracranial glioblastoma and medulloblastoma xenografts by increasing apoptosis and decreasing the proliferation of tumor cells (Rubin J B, Kung A L, Klein R S, Chan J A, Sun Y, Schmidt K, Kieran M W, Luster A D, Segal R A. *Proc Natl Acad Sci USA.* 2003 100(23):13513-13518; Barbero S, Bonavia R, Bajetto A, Porcile C, Pirani P, Ravetti J L, Zona G L, Spaziante R, Florio T, Schettini G. Stromal *Cancer Res.* 2003, 63(8):1969-1974; Kijima T, Maulik G, Ma P C, Tibaldi E V, Turner R E, Rollins B, Sattler M, Johnson B E, Salgia R. *Cancer Res.* 2002; 62(21):6304-6311, and *Cancer Res.* 2002; 62(11):3106-3112. High level of expression of chemokine receptors has been associated with tumor dissemination and poor prognosis for colorectal cancer (Schimanski C. C. et al, *Clinical Cancer Research* 2005 11, 1743-1750); prostate cancer (Arya M. et al, *J. Experimental. Therapeutics and Oncology* 2004, 4, 291-303); and malignant melanoma (Scala S. et al, *Clinical Cancer Research* 2005, 11, 1835-1841).

There is increasing evidence suggesting that chemokines in general, and the interaction between the chemoattractant CXCL12/stromal cell-derived factor-1alpha and its receptor CXCR4 in particular, play a pivotal role in angiogenesis. Chemokines induce angiogenesis directly by binding their cognate receptors on endothelial cells, or indirectly by promoting inflammatory cell infiltrates, which deliver other angiogenic stimuli. A number of pro-inflammatory chemokines including interleukin 8 (IL-8), growth-regulated oncogene, stromal cell-derived factor 1 (SDF-1), monocyte chemotactic protein 1 (MCP-1), eotaxin 1, and I-309 have been shown to act as direct inducers of angiogenesis (Chen X, Beutler J A, McCloud T G, Loehfehn A, Yang L, Dong H F, Chertov O Y, Salcedo R, Oppenheim J J, Howard O M. *Clin Cancer Res.* 2003 9(8):3115-3123; Salcedo R, Oppenheim J J. *Microcirculation* 2003 (3-4):359-370).

Therefore, receptor specific tumor localization of dye-conjugated CXCR4-inhibitors is highly desirable and could in addition be used as inhibitors for treatment of cancer.

SUMMARY OF THE INVENTION

In the compounds described below, a new strategy is introduced to stabilize beta-hairpin conformations in dye conjugates of cyclic backbone-turn peptidomimetics which are exhibiting high CXCR4 antagonizing activity and having anticancer activity and which can be used as receptor-targeted contrast agents as well as in photodynamic therapy.

This involves transplanting the cationic and hydrophobic hairpin sequence onto a template, whose function is to restrain the peptide loop backbone into a hairpin geometry. The rigidity of the hairpin may be further influenced by introducing a disulfide bridge. Template-bound hairpin mimetic peptides have been described in the literature (D, Obrecht, M.

Altorfer, J. A. Robinson, *Adv. Med. Chem.* 1999, 4, 1-68; J. A. Robinson, *Syn. Lett.* 2000, 4, 429-441), but such molecules have not previously been evaluated for development of CXCR4 antagonizing dye-conjugated peptides. However, the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112).

These methods allow the synthesis and screening of large hairpin mimetic libraries, which in turn considerably facilitates structure-activity studies, and hence the discovery of new molecules with highly potent CXCR4 antagonizing activity or anti cancer activity and low cyclotoxicity and which are useful for diagnostic imaging and therapy; for detection of tumors and other abnormalities; for photoacoustic tumor imaging, detection and therapy; and sonofluorescence tumor imaging, detection and therapy; for and photodynamic therapy.

The dye conjugates of β-hairpin peptidomimetics obtained by the approach described here are useful as anticancer agents, as inhibitors of tumor growth, as apoptosis inducing agents, or as anti-metastasis agents; or as diagnostic agents. For diagnostic purposes the present dye conjugates of template-fixed β-hairpin peptidomimetics can be used in a diagnostic kit, and for therapeutic purposes in pharmaceutical compositions.

DETAILED DESCRIPTION OF PREFERRED EMBODIMENTS

Figure 1:
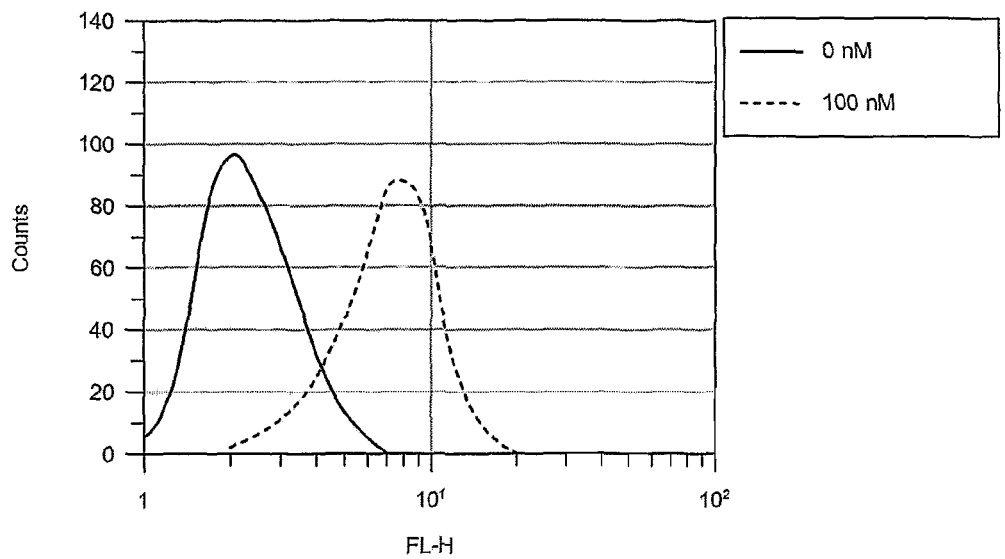
FIG. 1 shows histograms of untransfected cells (continuous line) or CXCR4 transfected cells (dotted line) labeled with peptidomimetic-dye conjugates and analyzed by FACS.

The β-hairpin peptidomimetics of the present invention are compounds of the general formula

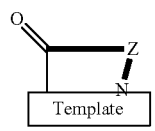

(I)

wherein

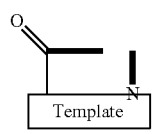

is a group of one of the formulae

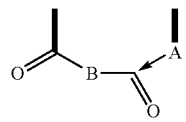

(a1)

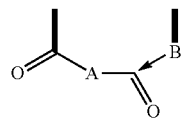

(a2)

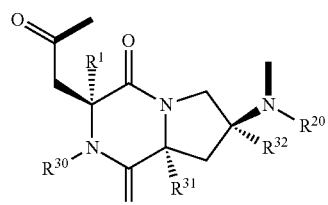

(b1)

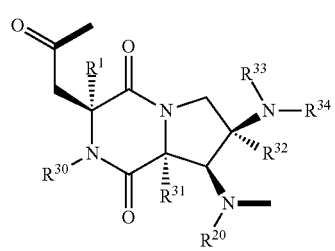

(b2)

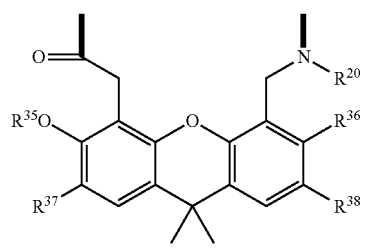

(c1)

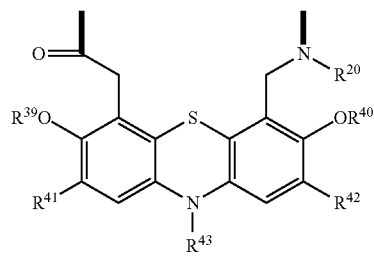

(c2)

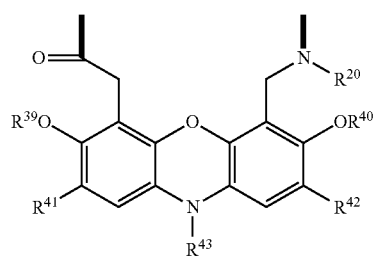

(c3)

(d)
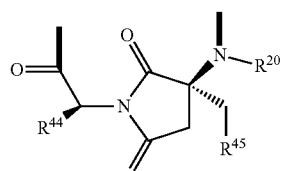
(e1)
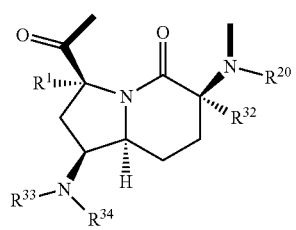
(e2)
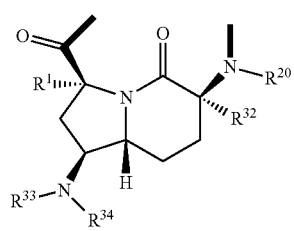
(e3)
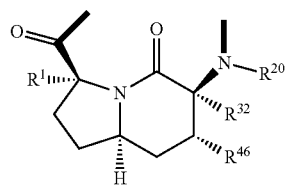
(e4)
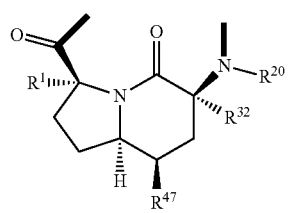
(f)
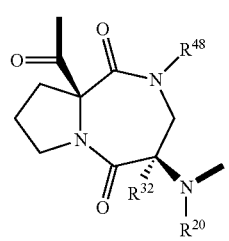
(g)
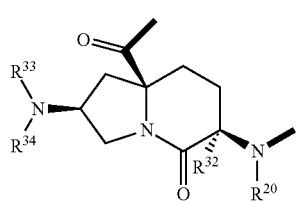
(h)
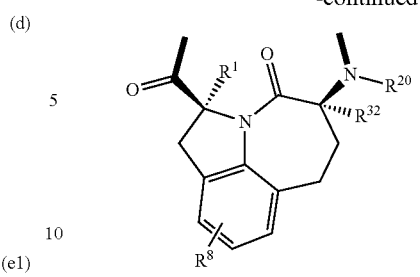
(i1)
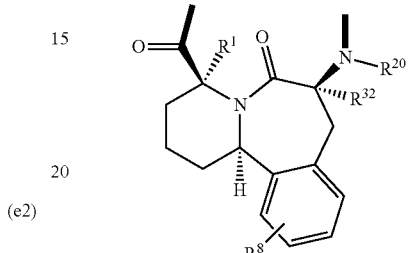
(i2)
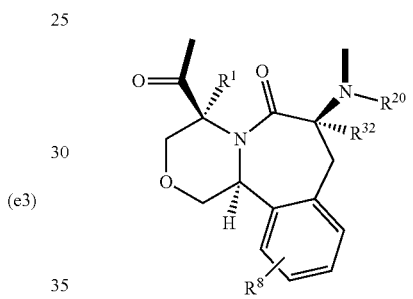
(i3)
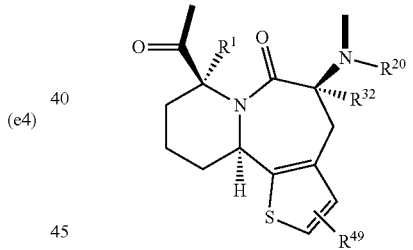
(i4)
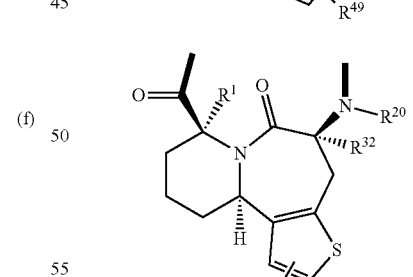
(j)
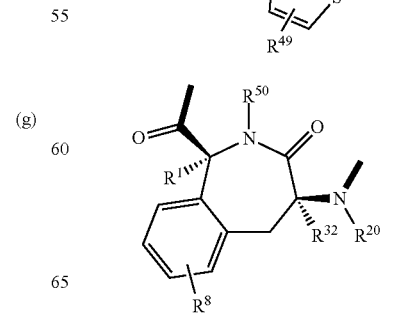

-continued
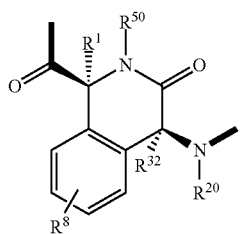
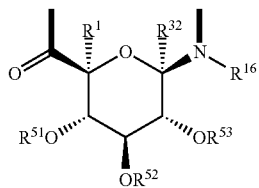
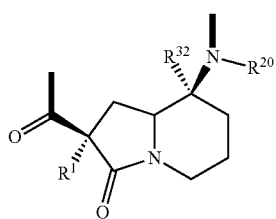
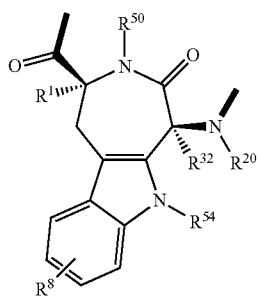
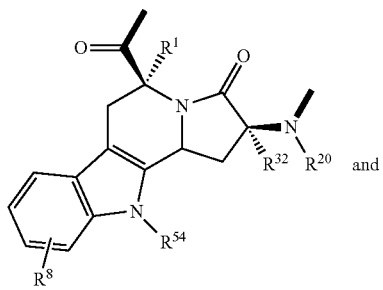
and
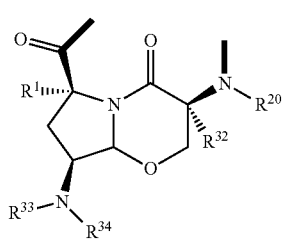
wherein
(k)
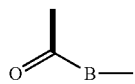
is Gly or the residue of an L-α-amino acid with B being a residue of formula —NR$^{20}$H(R$^{71}$)— or the enantiomer of one of the groups A1 to A69 as defined hereinafter; is a group of one of the formulae
(l)
(m)
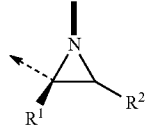  A1
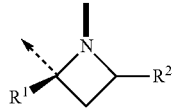 A2
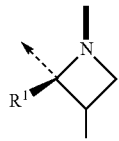 A3
(n)
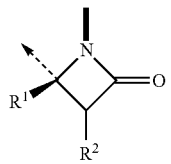 A4
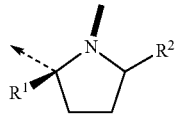 A5
(o)
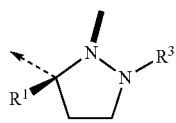 A6
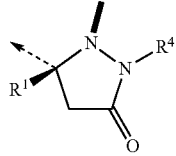 A7
(p)
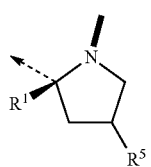 A8

-continued
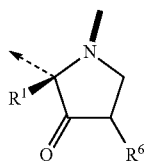 A9
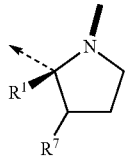 A10
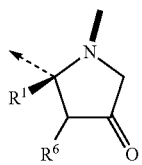 A11
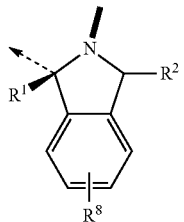 A12
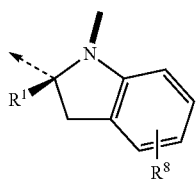 A13
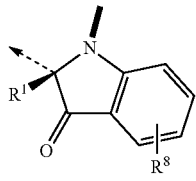 A14
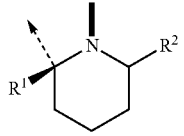 A15
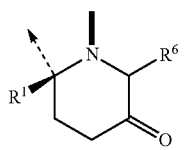 A16
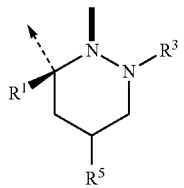 A17
-continued
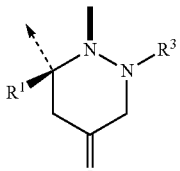 A18
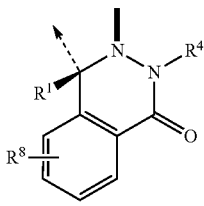 A19
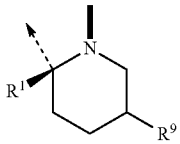 A20
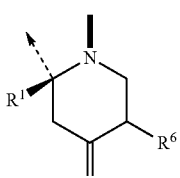 A21
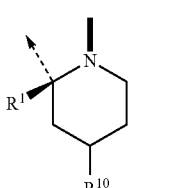 A22
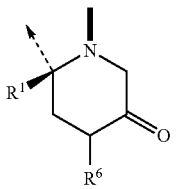 A23
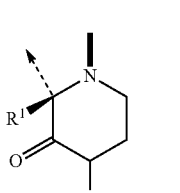 A24
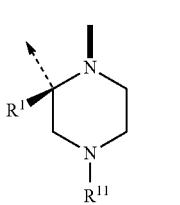 A25

-continued
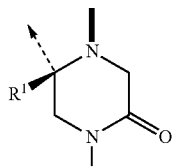
A26
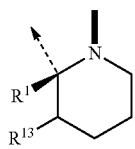
A27
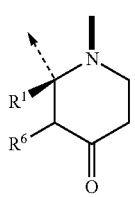
A28
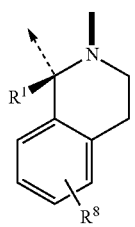
A29
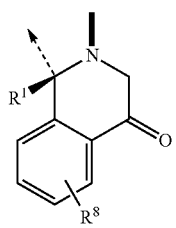
A30
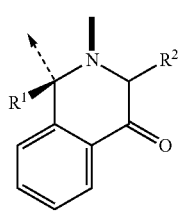
A31
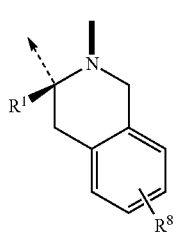
A32
-continued
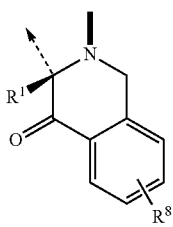
A33
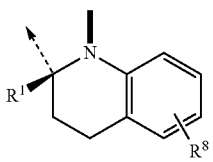
A34
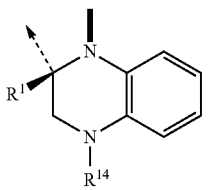
A35
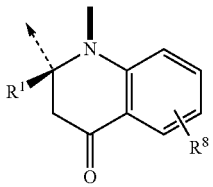
A36
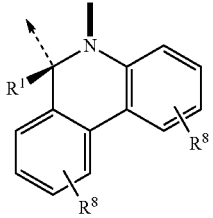
A37
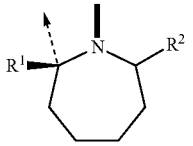
A38
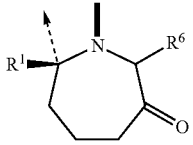
A39
A40

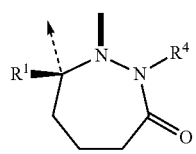 A41
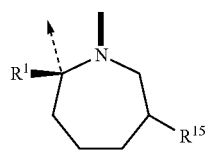 A42
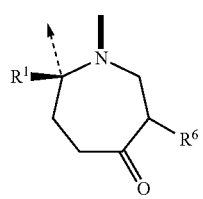 A43
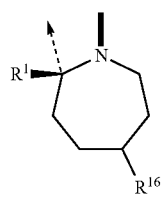 A44
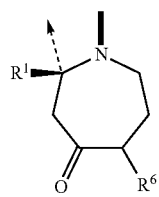 A45
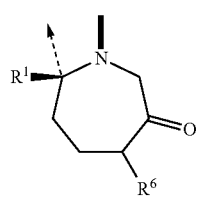 A46
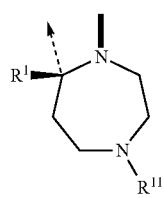 A47
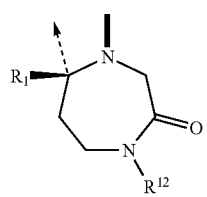 A48
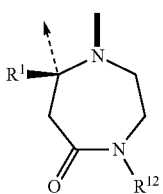 A49
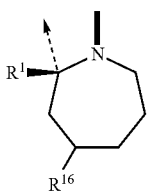 A50
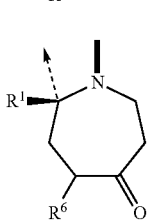 A51
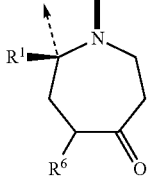 A52
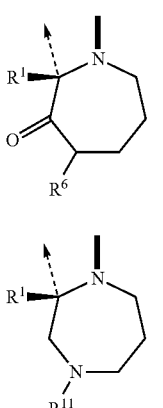 A53
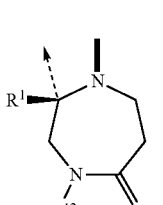 A54
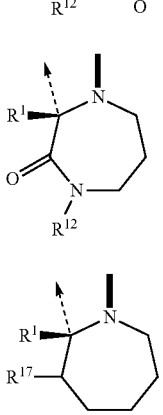 A55
A56

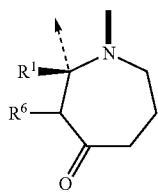
A57
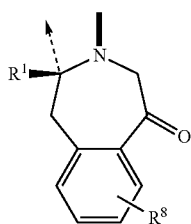
A64
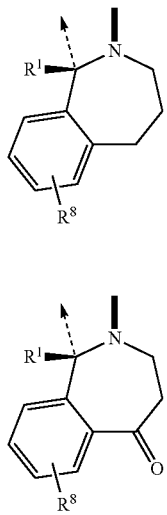
A58
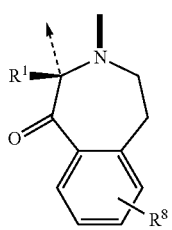
A65
A59
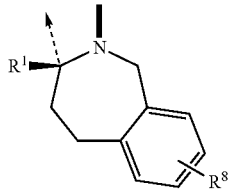
A66
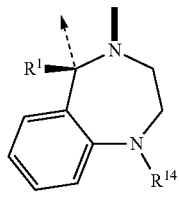
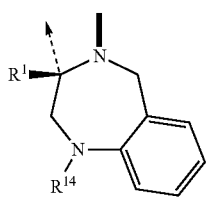
A67
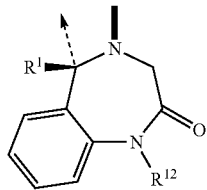
A60
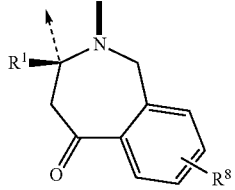
A68
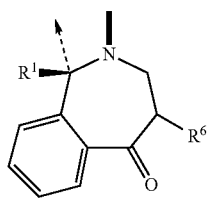
A61
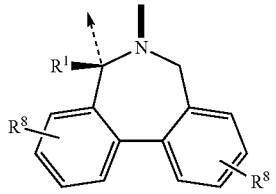
A69
A62
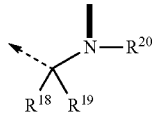
A70
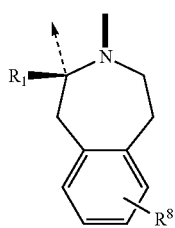
A63
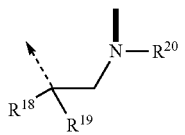
A71

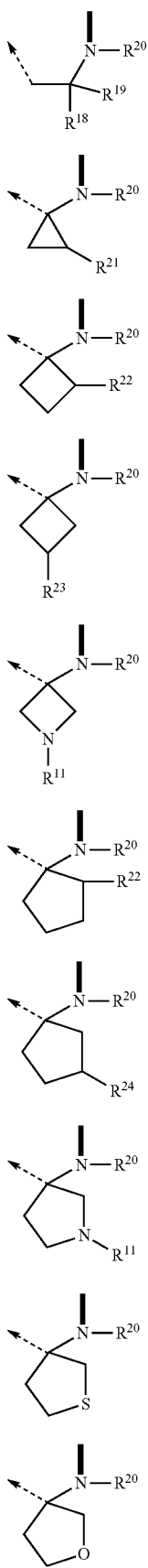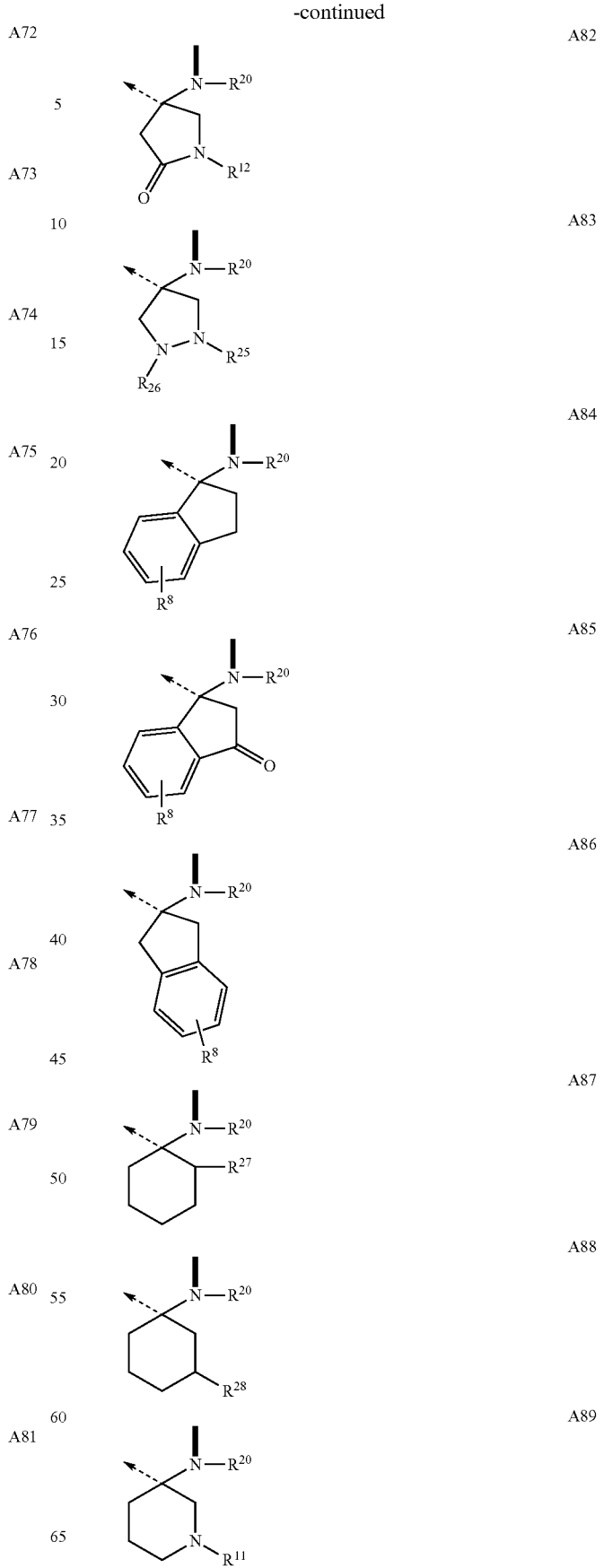

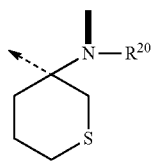
A90
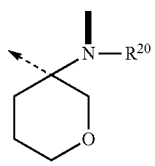
A91
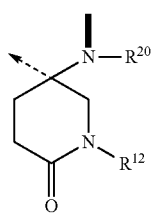
A92
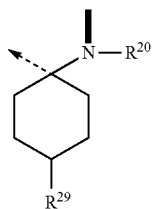
A93
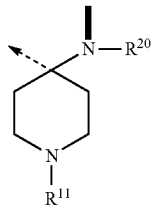
A94
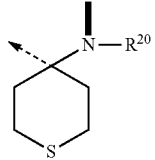
A95
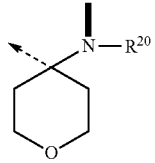
A96
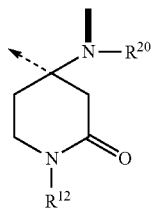
A97
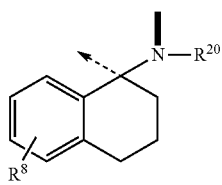
A98
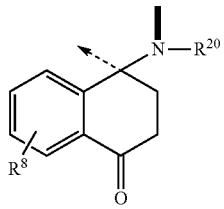
A99
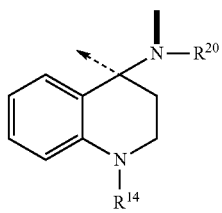
A100
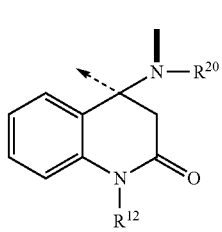
A101
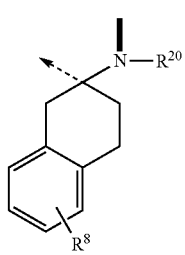
A102
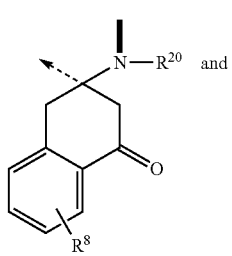 and
A103
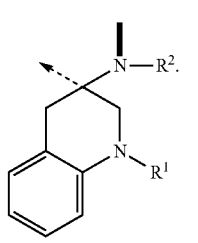
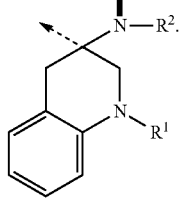
A104

$R^1$ is H; lower alkyl; or aryl-lower alkyl;

$R^2$ is H; alkyl; alkenyl; —$(CH_2)_m(CHR^{61})_sOR^{55}$; —$(CH_2)_m(CHR^{61})_sSR^{56}$;
—$(CH_2)_m(CHR^{61})_sNR^{33}R^{34}$;    —$(CH_2)_m(CHR^{61})_sOCONR^{33}R^{75}$;
—$(CH_2)_m(CHR^{61})_sNR^{20}CONR^{33}R^{82}$;    —$(CH_2)_o(CHR^{61})_sCOOR^{57}$;
—$(CH_2)_o(CHR^{61})_sCONR^{58}R^{59}$;    —$(CH_2)_o(CHR^{61})_sPO(OR^{60})_2$;
—$(CH_2)_o(CHR^{61})_sSO_2R^{62}$;    —$(CH_2)_o(CHR^{61})_sC_6H_4R^8$;
—$(CH_2)_m(CHR^{61})_sO$-L-Dye;
—$(CH_2)_m(CHR^{61})_sS$-L-Dye; —$(CH_2)_m(CHR^{61})_sNR^{34}$-L-Dye; —$(CH_2)_o(CHR^{61})_sCO$-L-Dye; or
-L-Dye;

$R^3$ is H; alkyl; alkenyl; —$(CH_2)_m(CHR^{61})_sOR^{55}$; —$(CH_2)_m(CHR^{61})_sSR^{56}$;
—$(CH_2)_m(CHR^{61})_sNR^{33}R^{34}$;    —$(CH_2)_m(CHR^{61})_sOCONR^{33}R^{75}$;
—$(CH_2)_m(CHR^{61})_sNR^{20}CONR^{33}R^{82}$; —$(CH_2)_o(CHR^{61})_sCOOR^{57}$;
—$(CH_2)_o(CHR^{61})_sCONR^{58}R^{59}$;    —$(CH_2)_o(CHR^{61})_sPO(OR^{60})_2$;
—$(CH_2)_o(CHR^{61})_sSO_2R^{62}$;    —$(CH_2)_o(CHR^{61})_sC_6H_4R^8$;
—$(CH_2)_m(CHR^{61})_sO$-L-Dye;
—$(CH_2)_m(CHR^{61})_sS$-L-Dye;—$(CH_2)_m(CHR^{61})_sNR^{34}$-L-Dye; —$(CH_2)_o(CHR^{61})_sCO$-L-Dye; or
-L-Dye;

$R^4$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$;
—$(CH_2)_m(CHR^{61})_sOCONR^{33}R^{75}$;    —$(CH_2)_m(CHR^{61})_sNR^{20}CONR^{33}R^{82}$;
—$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$;
—$(CH_2)_p(CHR^{61})_sSO_2R^{62}$; —$(CH_2)_m(CHR^{61})_sC_6H_4R^8$;
—$(CH_2)_m(CHR^{61})_sO$-L-Dye;
—$(CH_2)_o(CHR^{61})_sS$-L-Dye; —$(CH_2)_m(CHR^{61})_sNR^{34}$-L-Dye; —$(CH_2)_p(CHR^{61})_sCO$-L-Dye; or
-L-Dye;

$R^5$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$;    —$(CH_2)_o(CHR^{61})_sNR^{20}CONR^{33}R^{82}$;
—$(CH_2)_o(CHR^{61})_sCOOR^{57}$;    —$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$;    —$(CH_2)_o(CHR^{61})_sC_6H_4R^8$;
—$(CH_2)_o(CHR^{61})_sO$-L-Dye;
—$(CH_2)_m(CHR^{61})_sS$-L-Dye; —$(CH_2)_o(CHR^{61})_sNR^{34}$-L-Dye; —$(CH_2)_o(CHR^{61})_sCO$-L-Dye; or
-L-Dye;

$R^6$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$;    —$(CH_2)_o(CHR^{61})_sNR^{20}CONR^{33}R^{82}$;
—$(CH_2)_o(CHR^{61})_sCOOR^{57}$;    —$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$;    —$(CH_2)_o(CHR^{61})_sC_6H_4R^8$;
—$(CH_2)_o(CHR^{61})_sO$-L-Dye;
—$(CH_2)_o(CHR^{61})_sS$-L-Dye; —$(CH_2)_o(CHR^{61})_sNR^{34}$-L-Dye; —$(CH_2)_o(CHR^{61})_sCO$-L-Dye; or
-L-Dye;

$R^7$ is alkyl; alkenyl; —$(CH_2)_q(CHR^{61})_sOR^{55}$; —$(CH_2)_q(CHR^{61})_sNR^{33}R^{34}$;
—$(CH_2)_q(CHR^{61})_sOCONR^{33}R^{75}$;    —$(CH_2)_q(CHR^{61})_sNR^{20}CONR^{33}R^{82}$;
—$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$;
—$(CH_2)_r(CHR^{61})_sSO_2R^{62}$; —$(CH_2)_r(CHR^{61})_sC_6H_4R^8$;
—$(CH_2)_q(CHR^{61})_sO$-L-Dye;
—$(CH_2)_q(CHR^{61})_sNR^{34}$-L-Dye; —$(CH_2)_r(CHR^{61})_sCO-L$-Dye; or -L-Dye;

$R^8$ is H; Cl; F; $CF_3$; $NO_2$; lower alkyl; lower alkenyl; aryl; aryl-lower alkyl;
—$(CH_2)_o(CHR^{61})_sOR^{55}$;    —$(CH_2)_o(CHR^{61})_sSR^{56}$;
—$(CH_2)_o(CHR^{61})_sNR^{33}R^{34}$;
—$(CH_2)_o(CHR^{61})_sOCONR^{33}R^{75}$;    —$(CH_2)_o(CHR^{61})_sNR^{20}CONR^{33}R^{82}$;
—$(CH_2)_o(CHR^{61})_sCOOR^{57}$;    —$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$;    —$(CH_2)_o(CHR^{61})_sCOR^{64}$;
—$(CH_2)_o(CHR^{61})_sO$-L-Dye;
—$(CH_2)_o(CHR^{61})_sS$-L-Dye; —$(CH_2)_o(CHR^{61})_sNR^{34}$-L-Dye; —$(CH_2)_o(CHR^{61})_sCO$-L-Dye; or
-L-Dye;

$R^9$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$;    —$(CH_2)_o(CHR^{61})_sNR^{20}CONR^{33}R^{82}$;
—$(CH_2)_o(are)_sCOOR^{57}$; —$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$;    —$(CH_2)_o(CHR^{61})_sC_6H_4R^8$;
—$(CH_2)_o(CHR^{61})_sO$-L-Dye;
—$(CH_2)_o(CHR^{61})_sS$-L-Dye; —$(CH_2)_o(CHR^{61})$, $NR^{34}$-L-Dye; —$(CH_2)_o(CHR^{61})_sCO$-L-Dye; or
-L-Dye;

$R^{10}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$;
—$(CH_2)_o(CHR^{61})_sOCONR^{33}R^{75}$;    —$(CH_2)_o(CHR^{61})_sNR^{20}CONR^{33}R^{82}$;
—$(CH_2)_o(CHR^{61})_sCOOR^{57}$;    —$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$;    —$(CH_2)_o(CHR^{61})_sC_6H_4R^8$;
—$(CH_2)_o(CHR^{61})_sO$-L-Dye;
—$(CH_2)_o(CHR^{61})_sS$-L-Dye; —$(CH_2)_o(CHR^{61})_sNR^{34}$-L-Dye; —$(CH_2)_o(CHR^{61})_sCO$-L-Dye; or
-L-Dye;

$R^{11}$ is H; alkyl; alkenyl; —$(CH_2)_m(CHR^{61})_sOR^{55}$; —$(CH_2)_m(CHR^{61})_sNR^{33}R^{34}$;
—$(CH_2)_m(CHR^{61})_sOCONR^{33}R^{75}$;    —$(CH_2)_m(CHR^{61})_sNR^{20}CONR^{33}R^{82}$;
—$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$;
—$(CH_2)_o(CHR^{61})_sSO_2R^{62}$; —$(CH_2)_o(CHR^{61})_sC_6H_4R^8$;
—$(CH_2)_m(CHR^{61})_sO$-L-Dye;
—$(CH_2)_m(CHR^{61})_sNR^{34}$-L-Dye; —$(CH_2)_o(CHR^{61})_sCO$-L-Dye; or -L-Dye;

$R^{12}$ is H; alkyl; alkenyl; —$(CH_2)_m(CHR^{61})_sOR^{55}$; —$(CH_2)_m(CHR^{61})_sSR^{56}$;
—$(CH_2)_m(CHR^{61})_sNR^{33}R^{34}$;    —$(CH_2)_m(CHR^{61})_sOCONR^{33}R^{75}$;
—$(CH_2)_m(CHR^{61})_sNR^{20}CONR^{33}R^{82}$;    —$(CH_2)_r(CHR^{61})_sCOOR^{57}$; —$(CH_2)_r(CHR^{61})_sCONR^{58}R^{59}$;
—$(CH_2)_r(CHR^{61})_sPO(OR^{60})_2$;    —$(CH_2)_r(CHR^{61})_sSO_2R^{62}$; —$(CH_2)_r(CHR^{61})_sC_6H_4R^8$; —$(CH_2)_m(CHR^{61})_sO$-L-Dye;    —$(CH_2)_m(CHR^{61})_sNR^{34}$-L-Dye;    —$(CH_2)_r(CHR^{61})_sCO$-L-Dye; or
-L-Dye;

$R^{13}$ is alkyl; alkenyl; —$(CH_2)_q(CHR^{61})_sOR^{55}$; —$(CH_2)_q(CHR^{61})_sSR^{56}$; —$(CH_2)_q(CHR^{61})_sNR^{33}R^{34}$;
—$(CH_2)_q(CHR^{61})_sOCONR^{33}R^{75}$;    —$(CH_2)_q(CHR^{61})_sNR^{20}CONR^{33}R^{82}$;
—$(CH_2)_q(CHR^{61})_sCOOR^{57}$; —$(CH_2)_q(CHR^{61})_sCONR^{58}R^{59}$; —$(CH_2)_q(CHR^{61})_sPO(OR^{60})_2$;
—$(CH_2)_q(CHR^{61})_sSO_2R^{62}$;    —$(CH_2)_q(CHR^{61})_sC_6H_4R^8$;
—$(CH_2)_q(CHR^{61})_sO$-L-Dye;

—$(CH_2)_q(CHR^{61})_s$S-L-Dye; —$(CH_2)_q(CHR^{61})_s$NR$^{34}$-L-Dye; —$(CH_2)_q(CHR^{61})_s$CO-L-Dye; or
-L-Dye;

R$^{14}$ is H; alkyl; alkenyl; —$(CH_2)_m(CHR^{61})_s$OR$^{55}$; —$(CH_2)_m(CHR^{61})_s$NR$^{33}$R$^{34}$;
—$(CH_2)_m(CHR^{61})_s$OCONR$^{33}$R$^{76}$; —$(CH_2)_m(CHR^{61})_s$NR$^{20}$CONR$^{33}$R$^{82}$;
—$(CH_2)_q(CHR^{61})_s$COOR$^{57}$; —$(CH_2)_q(CHR^{61})_s$CONR$^{58}$R$^{59}$; —$(CH_2)_q(CHR^{61})_s$PO(OR$^{60}$)$_2$;
—$(CH_2)_q(CHR^{61})_s$SOR$^{62}$; —$(CH_2)_q(CHR^{61})_s$C$_6$H$_4$R$^8$;
—$(CH_2)_m(CHR^{61})_s$O-L-Dye;
—$(CH_2)_m(CHR^{61})_s$NR$^{34}$-L-Dye; —$(CH_2)_q(CHR^{61})_s$CO-L-Dye; or -L-Dye;

R$^{15}$ is alkyl; alkenyl; —$(CH_2)_o(CHR^{61})_s$OR$^{55}$; —$(CH_2)_o(CHR^{61})_s$SR$^{56}$; —$(CH_2)_o(CHR^{61})_s$NR$^{33}$R$^{34}$;
—$(CH_2)_o(CHR^{61})_s$OCONR$^{33}$R$^{75}$; —$(CH_2)_o(CHR^{61})_s$NR$^{20}$CONR$^{38}$R$^{82}$;
—$(CH_2)_o(CHR^{61})_s$COOR$^{57}$; —$(CH_2)_o(CHR^{61})_s$CONR$^{58}$R$^{59}$; —$(CH_2)_o(CHR^{61})_s$PO(OR$^{60}$)$_2$;
—$(CH_2)_o(CHR^{61})_s$SO$_2$R$^{62}$; —$(CH_2)_o(CHR^{61})_s$C$_6$H$_4$R$^8$;
—$(CH_2)_o(CHR^{61})_s$O-L-Dye;
—$(CH_2)_o(CHR^{61})_s$S-L-Dye; —$(CH_2)_o(CHR^{61})_s$NR$^{34}$-L-Dye; —$(CH_2)_q(CHR^{61})_s$CO-L-Dye; or -L-Dye R$^{16}$ is alkyl; alkenyl; —$(CH_2)_o(CHR^{61})_s$OR$^{55}$; —$(CH_2)_o(CHR^{61})_s$SR$^{56}$; —$(CH_2)_o(CHR^{61})_s$NR$^{33}$R$^{34}$;
—$(CH_2)_o(CHR^{61})_s$OCONR$^{33}$R$^{75}$; —$(CH_2)_o(CHR^{61})_s$NR$^{20}$CONR$^{33}$R$^{82}$;
—$(CH_2)_o(CHR^{61})_s$COOR$^{57}$; —$(CH_2)_o(CHR^{61})_s$CONR$^{58}$R$^{59}$; —$(CH_2)_o(CHR^{61})_s$PO(OR$^{60}$)$_2$;
—$(CH_2)_o(CHR^{61})_s$SO$_2$R$^{62}$; —$(CH_2)_o(CHR^{61})_s$C$_6$H$_4$R$^8$;
—$(CH_2)_o(CHR^{61})_s$O-L-Dye;
—$(CH_2)_o(CHR^{61})_s$S-L-Dye; —$(CH_2)_o(CHR^{61})_s$NR$^{34}$-L-Dye; —$(CH_2)_o(CHR^{61})_s$CO-L-Dye; or
-L-Dye;

R$^{17}$ is alkyl; alkenyl; —$(CH_2)_q(CHR^{61})_s$OR$^{55}$; —$(CH_2)_q(CHR^{61})_s$SR$^{56}$; —$(CH_2)_q(CHR^{61})_s$NR$^{33}$R$^{34}$;
—$(CH_2)_q(CHR^{61})_s$OCONR$^{33}$R$^{75}$; —$(CH_2)_q(CHR^{61})_s$NR$^{20}$CONR$^{33}$R$^{82}$;
—$(CH_2)_q(CHR^{61})_s$COOR$^{57}$; —$(CH_2)_q(CHR^{61})_s$CONR$^{58}$R$^{59}$; —$(CH_2)_q(CHR^{61})_s$PO(OR$^{60}$)$_2$;
—$(CH_2)_q(CHR^{61})_s$SO$_2$R$^{62}$; —$(CH_2)_q(CHR^{61})_s$C$_6$H$_4$R$^8$;
—$(CH_2)_q(CHR^{61})_s$O-L-Dye;
—$(CH_2)_q(CHR^{61})_s$S-L-Dye; —$(CH_2)_q(CHR^{61})_s$NR$^{34}$-L-Dye; —$(CH_2)_q(CHR^{61})_s$CO-L-Dye; or
-L-Dye;

R$^{18}$ is alkyl; alkenyl; —$(CH_2)_p(CHR^{61})_s$OR$^{55}$; —$(CH_2)_p(CHR^{61})_s$SR$^{56}$; —$(CH_2)_p(CHR^{61})_s$NR$^{33}$R$^{34}$;
—$(CH_2)_p(CHR^{61})_s$OCONR$^{33}$R$^{75}$; —$(CH_2)_p(CHR^{61})_s$NR$^{20}$CONR$^{33}$R$^{82}$;
—$(CH_2)_p(CHR^{61})_s$COOR$^{57}$; —$(CH_2)_p(CHR^{61})_s$CONR$^{58}$R$^{59}$; —$(CH_2)_p(CHR^{61})_s$PO(OR$^{60}$)$_2$;
—$(CH_2)_p(CHR^{61})_s$SO$_2$R$^{62}$; —$(CH_2)_o(CHR^{61})_s$C$_6$H$_4$R$^8$;
—$(CH_2)_p(CHR^{61})_s$O-L-Dye;
—$(CH_2)_p(CHR^{61})_s$S-L-Dye; —$(CH_2)_p(CHR^{61})_s$NR$^{34}$-L-Dye; —$(CH_2)_p(CHR^{61})_s$CO-L-Dye; or
-L-Dye;

R$^{19}$ is lower alkyl; —$(CH_2)_p(CHR^{61})_s$OR$^{55}$; —$(CH_2)_p(CHR^{61})_s$SR$^{56}$; —$(CH_2)_p(CHR^{61})_s$NR$^{33}$R$^{34}$;
—$(CH_2)_p(CHR^{61})_s$OCONR$^{33}$R$^{75}$; —$(CH_2)_p(CHR^{61})_s$NR$^{20}$CONR$^{33}$R$^{82}$;
—$(CH_2)_p(CHR^{61})_s$COOR$^{57}$; —$(CH_2)_p(CHR^{61})_s$CONR$^{58}$R$^{59}$; —$(CH_2)_p(CHR^{61})_s$PO(OR$^{60}$)$_2$;
—$(CH_2)_p(CHR^{61})_s$SO$_2$R$^{62}$; —$(CH_2)_p(CHR^{61})_s$C$_6$H$_4$R$^8$;
or —$(CH_2)_p(CHR^{61})_s$O-L-Dye;
—$(CH_2)_p(CHR^{61})_s$S-L-Dye; —$(CH_2)_p(CHR^{61})_s$NR$^{34}$-L-Dye; —$(CH_2)_p(CHR^{61})_s$CO-L-Dye; or
-L-Dye-; or R$^{18}$ and R$^{19}$ taken together can form: —$(CH_2)_{2-6}$—; —$(CH_2)_2$O$(CH_2)_2$—; —$(CH_2)_2$S$(CH_2)_2$—; or
—$(CH_2)_2$NR$^{57}$$(CH_2)_2$—;

R$^{20}$ is H; alkyl; alkenyl; or aryl-lower alkyl;

R$^{21}$ is H; alkyl; alkenyl; —$(CH_2)_o(CHR^{61})_s$OR$^{55}$; —$(CH_2)_o(CHR^{61})_s$SR$^{56}$; —$(CH_2)_o(CHR^{61})_s$NR$^{33}$R$^{34}$;
—$(CH_2)_o(CHR^{61})_s$OCONR$^{33}$R$^{75}$; —$(CH_2)_o(CHR^{61})_s$NR$^{20}$CONR$^{33}$R$^{82}$;
—$(CH_2)_o(CHR^{61})_s$COOR$^{57}$; —$(CH_2)_o(CHR^{61})_s$CONR$^{58}$R$^{59}$; —$(CH_2)_m(CHR^{61})_s$PO(OR$^{60}$)$_2$;
—$(CH_2)_o(CHR^{61})_s$SO$_2$R$^{62}$; —$(CH_2)_o(CHR^{61})_s$C$_6$H$_4$R$^8$;
—$(CH_2)_m(CHR^{61})_s$O-L-Dye;
—$(CH_2)_o(CHR^{61})_s$S-L-Dye; —$(CH_2)_o(CHR^{61})_s$NR$^{34}$-L-Dye; —$(CH_2)_o(CHR^{61})_s$CO-L-Dye or -L-Dye;

R$^{22}$ is H; alkyl; alkenyl; —$(CH_2)_o(CHR^{61})_s$OR$^{55}$; —$(CH_2)_o(CHR^{61})_s$SR$^{56}$; —$(CH_2)_o(CHR^{61})_s$NR$^{33}$R$^{34}$;
—$(CH_2)_o(CHR^{61})_s$OCONR$^{33}$R$^{75}$; —$(CH_2)_o(CHR^{61})_s$NR$^{20}$CONR$^{33}$R$^{82}$;
—$(CH_2)_m(CHR^{61})_s$COOR$^{57}$; —$(CH_2)_o(CHR^{61})_s$CONR$^{58}$R$^{59}$; —$(CH_2)_o(CHR^{61})_s$PO(OR$^{60}$)$_2$;
—$(CH_2)_o(CHR^{61})_s$SO$_2$R$^{62}$; —$(CH_2)_m(CHR^{61})_s$C$_6$H$_4$R$^8$;
—$(CH_2)_o(CHR^{61})_s$O-L-Dye;
—$(CH_2)_o(CHR^{61})_s$S-L-Dye; —$(CH_2)_o(CHR^{61})_s$NR$^{34}$-L-Dye; —$(CH_2)_o(CHR^{61})_s$CO-L-Dye; or
-L-Dye;

R$^{23}$ is alkyl; alkenyl; —$(CH_2)_o(CHR^{61})_s$OR$^{55}$; —$(CH_2)_o(CHR^{61})_s$SR$^{56}$; —$(CH_2)_o(CHR^{61})_s$NR$^{33}$R$^{34}$;
—$(CH_2)_o(CHR^{61})_s$OCONR$^{33}$R$^{75}$; —$(CH_2)_o(CHR^{61})_s$NR$^{20}$CONR$^{33}$R$^{82}$;
—$(CH_2)_o(CHR^{61})_s$COOR$^{57}$; —$(CH_2)_o(CHR^{61})_s$CONR$^{58}$R$^{59}$; —$(CH_2)_o(CHR^{61})_s$PO(OR$^{60}$)$_2$;
—$(CH_2)_o(CHR^{61})_s$SO$_2$R$^{62}$; —$(CH_2)_o(CHR^{61})_s$C$_6$H$_4$R$^8$;
—$(CH_2)_o(CHR^{61})_s$O-L-Dye;
—$(CH_2)_o(CHR^{61})_s$S-L-Dye; —$(CH_2)_o(CHR^{61})_s$NR$^{34}$-L-Dye; —$(CH_2)_o(CHR^{61})_s$CO-L-Dye; or
-L-Dye;

R$^{24}$ is alkyl; alkenyl; —$(CH_2)_o(CHR^{61})_s$OR$^{55}$; —$(CH_2)_o(CHR^{61})_s$SR$^{56}$; —$(CH_2)_o(CHR^{61})_s$NR$^{33}$R$^{34}$;
—$(CH_2)_o(CHR^{61})_s$OCONR$^{33}$R$^{75}$; —$(CH_2)_o(CHR^{61})_s$NR$^{20}$CONR$^{33}$R$^{82}$;
—$(CH_2)_o(CHR^{61})_s$COOR$^{57}$; —$(CH_2)_o(CHR^{61})_s$CONR$^{58}$R$^{59}$; —$(CH_2)_o(CHR^{61})_s$PO(OR$^{60}$)$_2$;
—$(CH_2)_o(CHR^{61})_s$SO$_2$R$^{62}$; —$(CH_2)_o(CHR^{61})_s$C$_6$H$_4$R$^8$;
—$(CH_2)_o(CHR^{61})_s$O-L-Dye;
—$(CH_2)_o(CHR^{61})_s$S-L-Dye; —$(CH_2)_o(CHR^{61})_s$NR$^{34}$-L-Dye; —$(CH_2)_o(CHR^{61})_s$CO-L-Dye; or
-L-Dye;

R$^{25}$ is H; alkyl; alkenyl; —$(CH_2)_m(CHR^{61})_s$OR$^{55}$; —$(CH_2)_m(CHR^{61})_s$SR$^{56}$;
—$(CH_2)_m(CHR^{61})_s$NR$^{33}$R$^{34}$; —$(CH_2)_m(CHR^{61})_s$OCONR$^{33}$R$^{75}$;
—$(CH_2)_m(CHR^{61})_s$NR$^{20}$CONR$^{33}$R$^{82}$; —$(CH_2)_o(CHR^{61})_s$COOR$^{57}$;
—$(CH_2)_o(CHR^{61})_s$CONR$^{58}$R$^{59}$; —$(CH_2)_o(CHR^{61})_s$PO(OR$^{60}$)$_2$;
—$(CH_2)_o(CHR^{61})_s$SO$_2$R$^{62}$; —$(CH_2)_o(CHR^{61})_s$C$_6$H$_4$R$^8$;
—$(CH_2)_m(CHR^{61})_s$O-L-Dye;
—$(CH_2)_m(CHR^{61})_s$S-L-Dye; —$(CH_2)_m(CHR^{61})_s$NR$^{34}$-L-Dye; —$(CH_2)_o(CHR^{61})_s$CO-L-Dye; or
-L-Dye;

R$^{26}$ is H; alkyl; alkenyl; —$(CH_2)_m(CHR^{61})_s$OR$^{55}$; —$(CH_2)_m(CHR^{61})_s$SR$^{56}$;
—$(CH_2)_m(CHR^{61})_s$NR$^{33}$R$^{34}$; —$(CH_2)_m(CHR^{61})_s$OCONR$^{33}$R$^{75}$;
—$(CH_2)_m(CHR^{61})_s$NR$^{20}$CONR$^{33}$R$^{82}$; —$(CH_2)_o(CHR^{61})_s$COOR$^{57}$; —$(CH_2)_o(CHR^{61})_s$CONR$^{58}$R$^{59}$;

—$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;
—$(CH_2)_o(CHR^{61})_sO$-L-Dye; —$(CH_2)_o(CHR^{61})_sS$-L-Dye; —$(CH_2)_o(CHR^{61})_sNR^{34}$-L-Dye;
—$(CH_2)_o(CHR^{61})_sCO$-L-Dye or -L-Dye; or $R^{25}$ and $R^{26}$ taken together can form: —$(CH_2)_{2-6}$—; —$(CH_2)_rO(CH_2)_r$—; —$(CH_2)_rS(CH_2)_r$—; or —$(CH_2)_rNR^{57}(CH_2)_r$—;

$R^{27}$ is H; alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sCOOR^{57}$; —$(CH_2)_m(CHR^{61})_sCONR^{58}R^{59}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sPO(OR^{60})_2$; —$(CH_2)_o(CHR^{61})_sSO_2R^{62}$; —$(CH_2)_o(CHR^{61})_sC_6H_4R^8$; —$(CH_2)_o(CHR^{61})_sO$-L-Dye; —$(CH_2)_o(CHR^{61})_sS$-L-Dye; —$(CH_2)_o(CHR^{61})_sNR^{34}$-L-Dye; —$(CH_2)_o(CHR^{61})_sCO$-L-Dye; or -L-Dye;

$R^{28}$ is alkyl; alkenyl; —$(CH_2)_o(CHR^{61})_s$—$OR^{55}$; —$(CH_2)_m(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; —$(CH_2)_o(CHR^{61})_sC_6H_4R^8$; —$(CH_2)_o(CHR^{61})_sO$-L-Dye; —$(CH_2)_o(CHR^{61})_sS$-L-Dye; —$(CH_2)_o(CHR^{61})_sNR^{34}$-L-Dye; —$(CH_2)_o(CHR^{61})_sCO$-L-Dye; or -L-Dye;

$R^{20}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; —$(CH_2)_o(CHR^{61})_sC_6H_4R^8$; —$(CH_2)_o(CHR^{61})_sO$-L-Dye; —$(CH_2)_o(CHR^{61})_sS$-L-Dye; —$(CH_2)_o(CHR^{61})_sNR^{34}$L-Dye-; —$(CH_2)_o(CHR^{61})_sCO$-L-Dye; or -L-Dye;

$R^{30}$ is H; alkyl; alkenyl; or aryl-lower alkyl;

$R^{31}$ is H; alkyl; alkenyl; —$(CH_2)_p(CHR^{61})_sOR^{55}$; —$(CH_2)_p(CHR^{61})NR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; —$(CH_2)_o(CHR^{61})_sC_6H_4R^8$; —$(CH_2)_p(CHR^{61})_sO$-L-Dye; —$(CH_2)_p(CHR^{61})_sS$-L-Dye; —$(CH_2)_p(CHR^{61})NR^{34}$-L-Dye; —$(CH_2)_o(CHR^{61})_sCO$-L-Dye; or -L-Dye;

$R^{32}$ is H; lower alkyl; or aryl-lower alkyl;

$R^{33}$ is H; alkyl, alkenyl; —$(CH_2)_o(CHR^{61})_sOR^{55}$; —$(CH_2)_m(CHR^{61})_sNR^{34}R^{63}$; —$(CH_2)_m(CHR^{61})_sOCONR^{75}R^{82}$; —$(CH_2)_m(CHR^{61})_sNR^{20}CONR^{78}R^{82}$; —$(CH_2)_o(CHR^{61})_sCOR^{64}$; —$(CH_2)_o(CHR^{61})_s$—$CONR^{58}R^{59}$, —$(CH_2)_o(CHR^{61})_sPO(OR^{60})_2$; —$(CH_2)_o(CHR^{61})_sSO_2R^{62}$; —$(CH_2)_o(CHR^{61})_sC_6H_4R^8$; —$(CH_2)_m(CHR^{61})_sO$-L-Dye; —$(CH_2)_m(CHR^{61})_sNR^{34}$-L-Dye; —$(CH_2)_o(CHR^{61})_sCO$-L-Dye; or -L-Dye;

$R^{34}$ is H; lower alkyl; aryl, or aryl-lower alkyl; or $R^{33}$ and $R^{34}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{35}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_p(CHR^{61})_sCOOR^{57}$ —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_p(CHR^{61})_sC_6H_4R^8$;

$R^{36}$ is H, alkyl; alkenyl; —$(CH_2)_o(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^{37}$ is H; F; Br; Cl; $NO_2$; $CF_3$; lower alkyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; —$(CH_2)_o(CHR^{61})_sC_6H_4R^8$; —$(CH_2)_p(CHR^{61})_sO$-L-Dye; —$(CH_2)_p(CHR^{61})_sS$-L-Dye; —$(CH_2)_p(CHR^{61})_sNR^{34}$-L-Dye; —$(CH_2)_o(CHR^{61})_sCO$-L-Dye; or -L-Dye;

$R^{38}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; —$(CH_2)_o(CHR^{61})_sC_6H_4R^8$; —$(CH_2)_p(CHR^{61})_sO$-L-Dye; —$(CH_2)_p(CHR^{61})_sS$-L-Dye; —$(CH_2)_p(CHR^{61})_sNR^{34}$-L-Dye; —$(CH_2)_o(CHR^{61})_sCO$-L-Dye; or -L-Dye;

$R^{39}$ is H; alkyl; alkenyl; or aryl-lower alkyl;

$R^{40}$ is H; alkyl; alkenyl; or aryl-lower alkyl;

$R^{41}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; —$(CH_2)_o(CHR^{61})_sC_6H_4R^8$; —$(CH_2)_p(CHR^{61})_sO$-L-Dye; —$(CH_2)_p(CHR^{61})_sS$-L-Dye; —$(CH_2)_p(CHR^{61})_sNR^{34}$-L-Dye; —$(CH_2)_o(CHR^{61})_sCO$-L-Dye; or -L-Dye;

$R^{42}$ is H; F; Br; Cl; $NO_2$; $CF_3$; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; —$(CH_2)_o(CHR^{61})_sC_6H_4R^8$; —$(CH_2)_p(CHR^{61})_sO$-L-Dye; —$(CH_2)_p(CHR^{61})_sS$-L-Dye; —$(CH_2)_p(CHR^{61})_sNR^{34}$-L-Dye-; —$(CH_2)_o(CHR^{61})_sCO$-L-Dye; or -L-Dye;

$R^{43}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$;

—(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$;
—(CH$_2$)$_o$(CHR$^{61}$)$_s$SO$_2$R$^{62}$; —(CH$_2$)$_o$(CHR$^{61}$)$_s$C$_6$H$_4$R$^8$;
—(CH$_2$)$_m$(CHR$^{61}$)$_s$O-L-Dye;
—(CH$_2$)$_m$(CHR$^{61}$)$_s$NR$^{34}$-L-Dye; —(CH$_2$)$_o$(CHR$^{61}$)$_s$CO-L-Dye; or -L-Dye;

R$^{44}$ is alkyl; alkenyl; —(CH$_2$)$_r$(CHR$^{61}$)$_s$OR$^{55}$; —(CH$_2$)$_o$(CHR$^{61}$)$_s$SR$^{56}$; —(CH$_2$)$_r$(CHR$^{61}$)$_s$NR$^{33}$R$^{34}$;
—(CH$_2$)$_r$(CHR$^{61}$)$_s$OCONR$^{33}$R$^{75}$; —(CH$_2$)$_r$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_r$(CHR$^{61}$)$_s$CONR$^{58}$R$^{59}$; —(CH$_2$)$_r$(CHR$^{61}$)$_s$PO(OR$^{60}$)$_2$;
—(CH$_2$)$_r$(CHR$^{61}$)$_s$SO$_2$R$^{62}$; or —(CH$_2$)$_r$(CHR$^{61}$)$_s$C$_6$H$_4$R$^8$;

R$^{45}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$;
—(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_s$(CHR$^{61}$)$_s$CONR$^{58}$R$^{59}$; —(CH$_2$)$_o$(CHR$^{61}$)$_s$PO(OR$^{60}$)$_2$;
—(CH$_2$)$_s$(CHR$^{61}$)$_s$SO$_2$R$^{62}$; —(CH$_2$)$_o$(CHR$^{61}$)$_s$C$_6$H$_4$R$^8$;
—(CH$_2$)$_o$(CHR$^{61}$)$_s$O—; L-Dye
—(CH$_2$)$_o$(CHR$^{61}$)$_s$S-L-Dye; —(CH$_2$)$_o$(CHR$^{61}$)$_s$NR$^{34}$-L-Dye; —(CH$_2$)$_s$(CHR$^{61}$)$_s$CO-L-Dye; or
-L-Dye;

R$^{46}$ is H; alkyl; alkenyl; or —(CH$_2$)$_o$(CHR$^{61}$)$_p$C$_6$H$_4$R$^8$;
R$^{47}$ is H; alkyl; alkenyl; —(CH$_2$)$_o$(CHR$^{61}$)$_s$OR$^{55}$; —(CH$_2$)$_o$(CHR$^{61}$)$_s$O-L-Dye; or -L-Dye;
R$^{48}$ is H; lower alkyl; lower alkenyl; or aryl-lower alkyl;
R$^{49}$ is H; alkyl; alkenyl; —(CHR$^{61}$)$_s$COOR$^{57}$; (CHR$^{61}$)$_s$CONR$^{58}$R$^{59}$; (CHR$^{61}$)$_s$PO(OR$^{60}$)$_2$; —(CHR$^{61}$)$_s$SOR$^{62}$; r-(CHR$^{61}$)$_s$C$_6$H$_4$R$^8$; —(CHR$^{61}$)$_s$O-L-Dye; —(CHR$^{61}$)$_s$S—; —(CHR$^{61}$)$_s$NR$^{34}$-L-Dye; —(CHR$^{61}$)$_s$CO-L-Dye; or -L-Dye;

R$^{50}$ is H; lower alkyl; or aryl-lower alkyl;
R$^{51}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CHR$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;
—(CH$_2$)$_o$(CHR$^{61}$)$_s$CONR$^{58}$R$^{59}$; —(CH$_2$)$_o$(CHR$^{61}$)$_p$PO(OR$^{60}$)$_2$;
—(CH$_2$)$_p$(CHR$^{61}$)$_s$SO$_2$R$^{62}$; —(CH$_2$)$_p$(CHR$^{61}$)$_s$C$_6$H$_4$R$^8$;
—(CH$_2$)$_m$(CHR$^{61}$)$_s$O-L-Dye;
—(CH$_2$)$_m$(CHR$^{61}$)$_s$S-L-Dye; —(CH$_2$)$_m$(CHR$^{61}$)$_s$NR$^{34}$-L-Dye; —(CH$_2$)$_o$(CHR$^{61}$)$_s$CO-L-Dye; or
-L-Dye;

R$^{52}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$;
—(CH$_2$)$_m$(CHR$^{61}$)$_s$NR$^{33}$R$^{34}$; —(CH$_2$)$_m$(CH—R$^{61}$)$_s$OCONR$^{33}$R$^{75}$;
—(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;
—(CH$_2$)$_o$(CHR$^{61}$)$_s$CONR$^{58}$R$^{59}$; —(CH$_2$)$_o$(CHR$^{61}$)$_p$PO(OR$^{60}$)$_2$;
—(CH$_2$)$_p$(CHR$^{61}$)$_s$SO$_2$R$^{62}$; —(CH$_2$)$_p$(CHR$^{61}$)$_s$C$_6$H$_4$R$^8$;
—(CH$_2$)$_m$(CHR$^{61}$)$_s$O-L-Dye;
—(CH$_2$)$_m$(CHR$^{61}$)$_s$S-L-Dye; —(CH$_2$)$_m$(CHR$^{61}$)$_s$NR$^{34}$-L-Dye; —(CH$_2$)$_o$(CHR$^{61}$)$_s$CO-L-Dye; or
-L-Dye;

R$^{53}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$;
—(CH$_2$)$_o$(CHR$^{61}$)$_s$CONR$^{58}$R$^{59}$; —(CH$_2$)$_o$(CHR$^{61}$)$_p$PO(OR$^{60}$)$_2$;
—(CH$_2$)$_p$(CHR$^{61}$)$_s$SO$_2$R$^{62}$; —(CH$_2$)$_p$(CHR$^{61}$)$_s$C$_6$H$_4$R$^8$;
—(CH$_2$)$_m$(CHR$^{61}$)$_s$O-L-Dye;
—(CH$_2$)$_m$(CHR$^{61}$)$_s$S-L-Dye; —(CH$_2$)$_m$(CHR$^{61}$)$_s$NR$^{34}$-L-Dye; —(CH$_2$)$_o$(CHR$^{61}$)$_s$CO-L-Dye; or
-L-Dye;

R$^{54}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$;
—(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$;
—(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$C$_6$H$_4$R$^8$;

R$^{55}$ is H; lower alkyl; lower alkenyl; aryl-lower alkyl;
—(CH$_2$)$_m$(CHR$^{61}$)$_s$NR$^{34}$R$^{63}$; —(CH$_2$)$_m$(CHR$^{61}$)$_s$OCONR$^{75}$R$^{82}$;
—(CH$_2$)$_m$(CHR$^{61}$)$_s$NR$^{20}$CONR$^{78}$R$^{82}$; —(CH$_2$)$_o$(CHR$^{61}$)$_s$COR$^{64}$; —(CH$_2$)$_o$(CHR$^{61}$)COOR$^{57}$;
—(CH$_2$)$_o$(CHR$^{61}$)$_s$CONR$^{58}$R$^{59}$; —(CH$_2$)$_m$(CHR$^{61}$)$_s$OR$^{57}$; —(CH$_2$)$_m$(CHR$^{61}$)$_s$O-L-Dye;
—(CH$_2$)$_m$(CHR$^{61}$)$_s$NR$^{34}$-L-Dye; —(CH$_2$)$_o$(CHR$^{61}$)$_s$CO-L-Dye; or -L-Dye;

R$^{56}$ is H; lower alkyl; lower alkenyl; aryl-lower alkyl;
—(CH$_2$)$_m$(CHR$^{61}$)$_s$OR$^{57}$;
—(CH$_2$)$_m$(CHR$^{61}$)$_s$NR$^{34}$R$^{63}$; —(CH$_2$)$_m$(CHR$^{61}$)$_s$OCONR$^{75}$R$^{82}$;
—(CH$_2$)$_m$(CHR$^{61}$)$_s$NR$^{20}$CONR$^{78}$R$^{82}$; —(CH$_2$)$_o$(CHR$^{61}$)$_s$—COR$^{64}$;
—(CH$_2$)$_o$(CHR$^{61}$)$_s$CONR$^{58}$R$^{59}$; —(CH$_2$)$_m$(CHR$^{61}$)$_s$O-L-Dye; —(CH$_2$)$_m$(CHR$^{61}$)$_s$NR$^{34}$-L-Dye;
—(CH$_2$)$_m$(CHR$^{61}$)$_s$CO-L-Dye; or -L-Dye;

R$^{57}$ is H; lower alkyl; lower alkenyl; aryl lower alkyl; or heteroaryl lower alkyl;
R$^{58}$ is H; lower alkyl; lower alkenyl; aryl; heteroaryl; aryl-lower alkyl; or heteroaryl-lower alkyl;
R$^{59}$ is H; lower alkyl; lower alkenyl; aryl; heteroaryl; aryl-lower alkyl; or heteroaryl-lower alkyl; or
R$^{58}$ and R$^{59}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;
R$^{60}$ is H; lower alkyl; lower alkenyl; aryl; or aryl-lower alkyl;
R$^{61}$ is alkyl; alkenyl; aryl; heteroaryl; aryl-lower alkyl; heteroaryl-lower alkyl; —(CH$_2$)$_m$OR$^{55}$;
—(CH$_2$)$_m$NR$^{33}$R$^{34}$; —(CH$_2$)$_m$OCONR$^{75}$R$^{82}$; —(CH$_2$)$_m$NR$^{20}$CONR$^{78}$R$^{82}$; —(CH$_2$)$_o$COOR$^{37}$;
—(CH$_2$)$_o$NR$^{58}$R$^{59}$; or —(CH$_2$)$_o$PO(COR$^{60}$)$_2$;
R$^{62}$ is lower alkyl; lower alkenyl; aryl, heteroaryl; or aryl-lower alkyl;
R$^{63}$ is H; lower alkyl; lower alkenyl; aryl, heteroaryl; aryl-lower alkyl; heteroaryl-lower alkyl;
—COR$^{64}$; —COOR$^{57}$; —CONR$^{58}$R$^{59}$; —SO$_2$R$^{62}$; or —PO(OR$^{60}$)$_2$; or
R$^{34}$ and R$^{63}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;
R$^{64}$ is H; lower alkyl; lower alkenyl; aryl; heteroaryl; aryl-lower alkyl; heteroaryl-lower alkyl;
—(CH$_2$)$_p$(CHR$^{61}$)$_s$OR$^{65}$; —(CH$_2$)$_p$(CHR$^{61}$)$_s$SR$^{66}$; —(CH$_2$)$_p$(CUR$^{61}$)$_s$NR$^{34}$R$^{63}$;
—(CH$_2$)$_p$(CHR$^{61}$)$_s$OCONR$^{75}$R$^{82}$; —(CH$_2$)$_p$(CHR$^{61}$)$_s$NR$^{20}$CONR$^{78}$R$^{82}$; —(CHD$_p$(CHR$^{61}$)$_s$O-L-Dye;
—(CH$_2$)$_p$(CHR$^{61}$)$_s$S-L-Dye; —(CH$_2$)$_p$(CHR$^{61}$)$_s$NR$^{34}$-L-Dye; or -L-Dye;

R$^{65}$ is H; lower alkyl; lower alkenyl; aryl, aryl-lower alkyl; heteroaryl-lower alkyl; —COR$^{57}$; —COOR$^{57}$; or —CONR$^{58}$R$^{59}$;
R$^{66}$ is H; lower alkyl; lower alkenyl; aryl; aryl-lower alkyl; heteroaryl-lower alkyl; or —CONR$^{58}$R$^{59}$;
m is 2-4; o is 0-4; p is 1-4; q is 0-2; r is 1 or 2; s is 0 or 1;

L is a direct bond or one of the linkers

—$(CH_2)_u$—; —$(CH_2)_u CONR^{20}$—; —$N(R^{20})CO(CH_2)_u$—; —$OCO(CH_2)_u$—; —$(CH_2)u\text{-}CO_2$—; —$OCONH$—;
—$OCO_2$—; —$HNCONH$—; —$HNCSNH$—;
—$HNNHCO$—; —$OSO_2$—; —$NR(CH_2)_u CONR$—;
—$O(CH_2)_u O$—;
—$CONR^{20}(CH_2)_u NR^{20}CO$—; —$NR^{20}CO(CH_2)_u CONR^{20}$—; —$S(CH_2)_u$—; —$[(CH_2)_u$—$X]_t$—$CH_2$—;
—$[(CH_2)_u$—$X]_t$—$CH_2 CONR^{20}$—, —$N(R^{20})CO$—$[(CH_2)_u$—$X]_t$—$CH_2$—; —$NR[(CH_2)_u$—$X]_t$—$CH_2 CONR$—; —$CONR^{20}[(CH_2)_u$—$X]_t$—$CH_2 NR^{20}CO$—; and —$NR^{20}CO[(CH_2)_u$—$X]_t$—$CH_2 CONR^{20}$— where X is absent or —O—; —$NR^{20}$—; —S—; or —$SO_2$—; u is 1-10, and t is 1-8;

the residue designated as "Dye" is an aromatic or an homoaromatic radical derived from a dyestuff selected from the group consisting of cyanines, indoyanines, phtalocyanines, rhodamines phenoxazines, phenothiazines, phenoselenazins, fluoresceins, porpyrins, squaraines, corrins, croconiums, azo dyes, methane dyes, indolenium dyes, chlorophyll derivatives, chlorin derivatives, and bacteriochlorin derivatives, all having a wavelength between 300 and 1200 nm; and Z is a chain of 14 α-amino acid residues, the positions of said amino acid residues in said chain being counted starting from the N-terminal amino acid, whereby these amino acid residues are, depending on their position in the chain, Gly, or Pro, or of formula -A-CO—, or of formula —B—CO—, or of one of the types C: —$NR^{20}CH(R^{72})CO$—;
D: —$NR^{20}CH(R^{73})CO$—;
E: —$NR^{20}CH(R^{74})CO$—;
F: —$NR^{20}CH(R^{84})CO$—;
LD: —$NR^{20}CH(R^{86})CO$—; and
H: —$NR^{20}$—$CH(CO$—$)$—$(CH_2)_{4\text{-}7}$—$CH(CO$—$)$—$NR^{20}$—;
—$NR^{20}$—$CH(CO$—$)$—$(CH_2)_p SS(CH_2)_p$—$CH(CO$—$)$—$NR^{20}$—; —$NR^{20}$—$CH(CO$—$)$—$(CH_2)_p NR^{20}CO(CH_2)_p$—$CH(CO$—$)$—$NR^{20}$—; or —$NR^{20}$—$CH(CO$—$)$—$(CH_2)_p NR^{20}CONR^{20}(CH_2)_p$—$CH(CO$—$)$—$NR^{20}$—;

$R^{71}$ is lower alkyl; lower alkenyl; —$(CH_2)_p(CHR^{61})_s OR^{75}$; —$(CH_2)_p(CHR^{61})_s SR^{75}$;
—$(CH_2)_p(CHR^{61})_s NR^{33}R^{34}$; —$(CH_2)_p(CHR^{61})_s OCONR^{33}R^{75}$; —$(CH_2)_p(CHR^{61})_s NR^{20}CONR^{33}R^{82}$;
—$(CH_2)_o(CHR^{61})_s COOR^{75}$; —$(CH_2)_p CONR^{58}R^{59}$;
—$(CH_2)_p PO(OR^{62})_2$; —$(CH_2)_p SO_2 R^{62}$; or
—$(CH_2)_o$—$C_6 R^{67}R^{68}R^{69}R^{70}R^{76}$;

$R^{72}$ is H, lower alkyl; lower alkenyl; —$(CH_2)_p(CHR^{61})_s OR^{85}$; or —$(CH_2)_p(CHR^{61})_s SR^{85}$;

$R^{73}$ is —$(CH_2)_o R^{77}$; —$(CH_2)_r O(CH_2)_o R^{77}$; —$(CH_2)_r S(CH_2)_o R^{77}$; or —$(CH_2)_r NR^{20}(CH_2)_o R^{77}$;

$R^{74}$ is —$(CH_2)_p NR^{78}R^{79}$; —$(CH_2)_p NR^{77}R^{80}$; —$(CH_2)_p C(=NR^{80})NR^{78}R^{79}$; —$(CH_2)_p C(=NOR^{50})NR^{78}R^{79}$;
—$(CH_2)_p C(=NNR^{78}R^{79})NR^{78}R^{79}$; —$(CH_2)_p NR^{80}C(=NR^{80})NR^{78}R^{79}$;
—$(CH_2)_p N=C(NR^{78}R^{80})NR^{79}R^{80}$; —$(CH_2)_p C_6H_4 NR^{78}R^{79}$; —$(CH_2)_p C_6H_4 NR^{77}R^{80}$;
—$(CH_2)_p C_6H_4 C(=NR^{80})NR^{78}R^{79}$; —$(CH_2)_p C_6H_4 C(=NOR^{50})NR^{78}R^{79}$;
—$(CH_2)_p C_6H_4 C(=NNR^{78}R^{79})NR^{78}R^{79}$; —$(CH_2)_p C_6H_4 NR^{80}C(=NR^{80})NR^{78}R^{79}$;
—$(CH_2)_p C_6H_4 N=C(NR^{78}R^{80})NR^{79}R^{80}$; —$(CH_2)_r O(CH_2)_m NR^{78}R^{79}$; —$(CH_2)_r O(CH_2)_m NR^{77}R^{80}$;
—$(CH_2)_r O(CH_2)_p C(=NR^{80})NR^{78}R^{79}$; —$(CH_2)_r O(CH_2)_p C(=NOR^{50})NR^{78}R^{79}$;
—$(CH_2)_r O(CH_2)_p C(=NNR^{78}R^{79})NR^{78}R^{79}$; —$(CH_2)_r O(CH_2)_m N=C(=NR^{80})NR^{78}R^{79}$;
—$(CH_2)_r O(CH_2)_m N=C(NR^{78}R^{80})NR^{79}R^{80}$; —$(CH_2)_r O(CH_2)_p C_6H_4 CNR^{78}R^{79}$;
—$(CH_2)_r O(CH_2)_p C_6H_4 C(=NR^{80})NR^{78}R^{79}$; —$(CH_2)_r O(CH_2)_p C_6H_4 C(=NOR^{50})NR^{78}R^{79}$;
—$(CH_2)_r O(CH_2)_p C_6H_4 C(=NNR^{78}R^{79})NR^{78}R^{79}$;
—$(CH_2)_r O(CH_2)_p C_6H_4 NR^{80}C(=NR^{80})NR^{78}R^{79}$;
—$(CH_2)_r S(CH_2)_m NR^{78}R^{79}$;
—$(CH_2)_r S(CH_2)_m NR^{77}R^{80}$; —$(CH_2)_r S(CH_2)_p C(=NR^{80})NR^{78}R^{79}$;
—$(CH_2)_r S(CH_2)_p C(=NOR^{50})NR^{78}R^{79}$; —$(CH_2)_r S(CH_2)_p C(=NNR^{78}R^{79})NR^{78}R^{79}$;
—$(CH_2)_r S(CH_2)_m NR^{80}C(=NR^{80})NR^{78}R^{79}$; —$(CH_2)_r S(CH_2)_m N=C(NR^{78}R^{80})NR^{79}R^{80}$;
—$(CH_2)_r S(CH_2)_p C_6H_4 CNR^{78}R^{79}$; —$(CH_2)_r S(CH_2)_p C_6H_4 C(=NR^{80})NR^{78}R^{79}$;
—$(CH_2)_r S(CH_2)_p C_6H_4 C(=NOR^{50})NR^{78}R^{79}$; —$(CH_2)_r S(CH_2)_p C_6H_4 C(=NNR^{78}R^{79})NR^{78}R^{79}$;
—$(CH_2)_r S(CH_2)_p C_6H_4 NR^{80}C(=NR^{80})NR^{78}R^{79}$;
—$(CH_2)_p NR^{80}COR^{64}$; —$(CH_2)_p NR^{80}COR^{77}$;
—$(CH_2)_p NR^{80}CONR^{78}R^{79}$; —$(CH_2)_p C_6H_4 NR^{80}CONR^{78}R^{79}$; or
—$(CH_2)_p NR^{20}CO$—$[(CH_2)_u$—$X]_t$—$CH_3$ where X is —O—; —$NR^{20}$—, or —S—; u is 1-3, and t is 1-6;

$R^{75}$ is lower alkyl; lower alkenyl; or aryl-lower alkyl; or $R^{33}$ and $R^{75}$ taken together can form: —$(CH_2)_{2\text{-}6}$—; —$(CH_2)_2 O(CH_2)_2$—; —$(CH_2)_2 S(CH_2)_2$—; or —$(CH_2)_2 NR^{57}(CH_2)_2$—; or $R^{75}$ and $R^{82}$ taken together can form: —$(CH_2)_{2\text{-}6}$—; —$(CH_2)_2 O(CH_2)_2$—; —$(CH_2)_2 S(CH_2)_2$—; or —$(CH_2)_2 NR^{57}(CH_2)_2$—;

$R^{76}$ is H; lower alkyl; lower alkenyl; aryl-lower alkyl; —$(CH_2)_o OR^{72}$; —$(CH_2)_o SR^{72}$;
—$(CH_2)_o NR^{33}R^{34}$; —$(CH_2)_o OCONR^{33}R^{75}$; —$(CH_2)_o NR^{20}CONR^{33}R^{82}$;
—$(CH_2)_o COOR^{75}$; —$(CH_2)_o CONR^{58}R^{59}$; —$(CH_2)_p PO(OR^{60})_2$; —$(CH_2)_p SO_2 R^{62}$; or
—$(CH_2)_o COR^{64}$;

$R^{77}$ is —$C_6 R^{67}R^{68}R^{69}R^{70}R^{76}$; or a heteroaryl group of one of the formulae

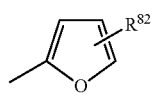

H1

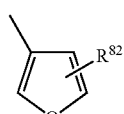

H2

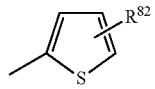

H3

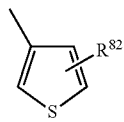

H4

-continued
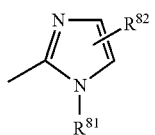
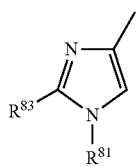
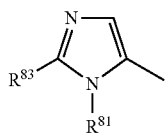
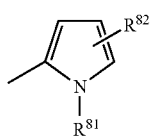
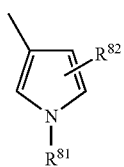
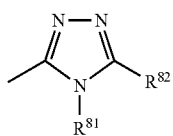
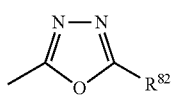
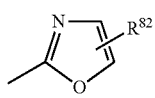
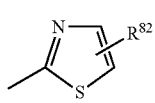
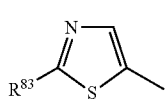
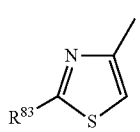
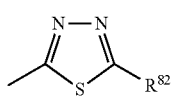
-continued
H5
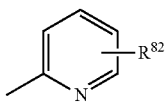 H17
H6
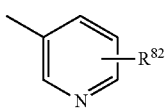 H18
H7
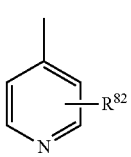 H19
H8
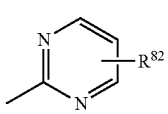 H20
H9
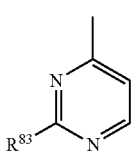 H21
H10
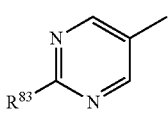 H22
H11
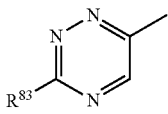 H23
H12
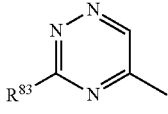 H24
H13
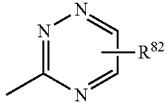 H25
H14
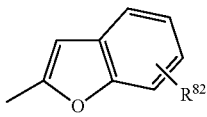 H26
H15
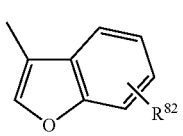 H27
H16
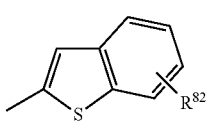 H28

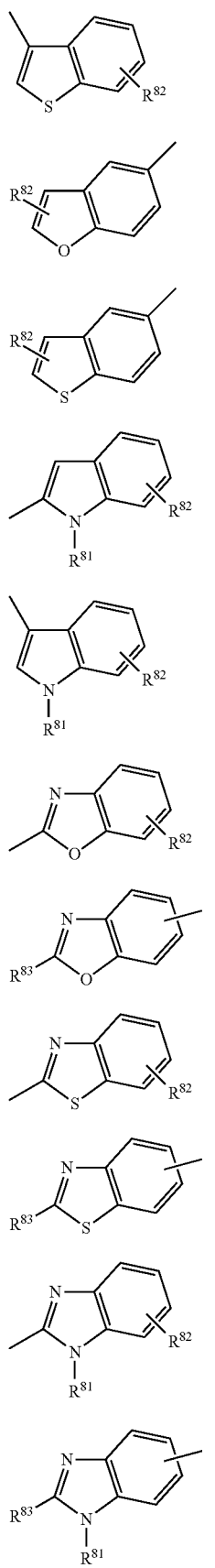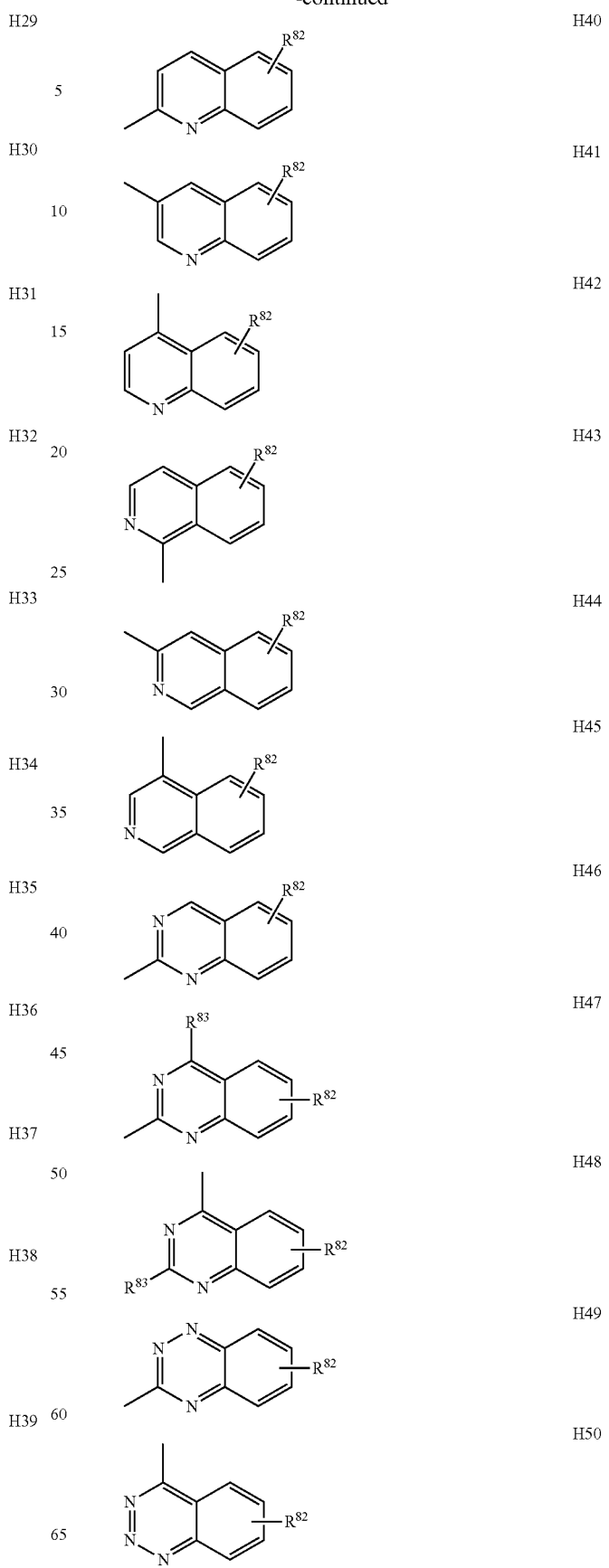

-continued

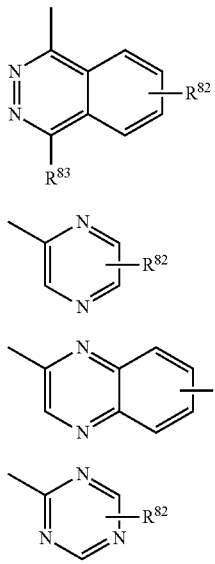

R$^{78}$ is H; lower alkyl; aryl; or aryl-lower alkyl;
R$^{78}$ and R$^{82}$ taken together can form: —(CH$_2$)$_{2-6}$—;
 —(CH$_2$)$_2$O(CH$_2$)$_2$—; —(CH$_2$)$_2$S(CH$_2$)$_2$—; or
 —(CH$_2$)$_2$NR$^{57}$(CH$_2$)$_2$—;
R$^{79}$ is H; lower alkyl; aryl; or aryl-lower alkyl; or
R$^{78}$ and R$^{79}$, taken together, can be —(CH$_2$)$_{2-7}$—;
 —(CH$_2$)$_2$O(CH$_2$)$_2$—; or —(CH$_2$)$_2$NR$^{57}$(CH$_2$)$_2$—;
R$^{80}$ is H; or lower alkyl;
R$^{81}$ is H; lower alkyl; or aryl-lower alkyl;
R$^{82}$ is H; lower alkyl; aryl; heteroaryl; or aryl-lower alkyl; or
R$^{33}$ and R$^{82}$ taken together can form: —(CH$_2$)$_{2-6}$—;
 —(CH$_2$)$_2$O(CH$_2$)$_2$—; —(CH$_2$)$_2$S(CH$_2$)$_2$—; or
 —(CH$_2$)$_2$NR$^{57}$(CH$_2$)$_2$—;
R$^{83}$ is H; lower alkyl; aryl; or —NR$^{78}$R$^{79}$;
R$^{84}$ is —(CH$_2$)$_m$(CHR$^{61}$)$_s$OH; —(CH$_2$)$_p$COOR$_{80}$;
 —(CH$_2$)$_m$(CBR$_{61}$)$_s$SH; —(CH$_2$)$_p$CONR$^{78}$R$^{79}$; —(CH$_2$)$_p$NR$^{80}$CONR$^{78}$R$^{79}$; —(CH$_2$)$_p$C$_6$H$_4$CONR$^{78}$R$^{79}$; or
 —(CH$_2$)$_p$C$_6$H$_4$NR$^{80}$CONR$^{78}$R$^{79}$;
R$^{85}$ is lower alkyl; or lower alkenyl;
R$^{86}$ is —(CH$_2$)$_p$(CHR$^{61}$)$_s$O-L-Dye; or —(CH$_2$)$_p$(CHR$^{61}$)$_s$S-L-Dye;
 —(CH$_2$)$_o$-L-Dye; —(CH$_2$)$_r$O(CH$_2$)$_o$-L-Dye; —(CH$_2$)$_r$S(CH$_2$)$_o$-L-Dye; —(CH$_2$)$_r$NR$^{20}$(CH$_2$)$_o$-L-Dye;
 —(CH$_2$)$_p$NR$^{78}$-L-Dye; —(CH$_2$)$_p$NR$^{77}$-L-Dye; —(CH$_2$)$_p$C(=NR$^{80}$)NR$^{78}$-L-Dye;
 —(CH$_2$)$_p$C(=NOR$^{50}$)NR$^{78}$-L-Dye; —(CH$_2$)$_p$C(=NNR$^{78}$R$^{79}$)NR$^{78}$-L-Dye;
 —(CH$_2$)$_p$NR$^{80}$C(=NR$^{80}$)NR$^{78}$-L-Dye; —(CH$_2$)$_p$N=C(NR$^{78}$R$^{80}$)NR$^{79}$-L-Dye;
 —(CH$_2$)$_p$C$_6$H$_4$NR$^{78}$-L-Dye; —(CH$_2$)$_p$C$_6$H$_4$C(=NR$^{80}$)N-L-Dye;
 —(CH$_2$)$_p$C$_6$H$_4$C(=NOR$^{50}$)NR$^{78}$-L-Dye; —(CH$_2$)$_p$C$_6$H$_4$C(=NNR$^{78}$R$^{79}$)NR$^{78}$-L-Dye;
 —(CH$_2$)$_p$C$_6$H$_4$NR$^{80}$C(=NR$^{80}$)NR$^{78}$-L-Dye; —(CH$_2$)$_p$C$_6$H$_4$N=C(NR$^{78}$R$^{80}$)NR$^{79}$-L-Dye;
 —(CH$_2$)$_r$O(CH$_2$)$_m$NR$^{78}$-L-Dye; —(CH$_2$)$_r$O(CH$_2$)$_m$NR$^{77}$-L-Dye;
 —(CH$_2$)$_r$O(CH$_2$)$_p$C(=NR$^{80}$)NR$^{78}$-L-Dye; —(CH$_2$)$_r$O(CH$_2$)$_p$C(=NOR$^{50}$)NR$^{78}$-L-Dye;
 —(CH$_2$)$_r$O(CH$_2$)$_p$C(=NNR$^{78}$R$^{79}$)NR$^{78}$-L-Dye;
 —(CH$_2$)$_r$O(CH$_2$)$_m$NR$^{80}$C(=NR$^{80}$)NR$^{78}$-L-Dye;
 —(CH$_2$)$_r$O(CH$_2$)$_m$N=C(NR$^{78}$R$^{80}$)NR$^{79}$-L-Dye;
 —(CH$_2$)$_r$O(CH$_2$)$_p$C$_6$H$_4$CNR$^{78}$-L-Dye;
 —(CH$_2$)$_r$O(CH$_2$)$_p$C$_6$H$_4$C(=NR$^{80}$)NR$^{78}$-L-Dye;
 —(CH$_2$)$_r$O(CH$_2$)$_p$C$_6$H$_4$C(=NOR$^{50}$)NR$^{78}$-L-Dye;
 —(CH$_2$)$_r$O(CH$_2$)$_p$C$_6$H$_4$C(=NNR$^{78}$R$^{79}$)NR$^{78}$-L-Dye;
 —(CH$_2$)$_r$O(CH$_2$)$_p$C$_6$H$_4$NR$^{80}$C(=NR$^{80}$)NR$^{78}$-L-Dye;
 —(CH$_2$)$_r$S(CH$_2$)$_m$NR$^{78}$-L-Dye;
 —(CH$_2$)$_r$S(CH$_2$)$_m$NR$^{77}$-L-Dye; —(CH$_2$)$_r$S(CH$_2$)$_p$C(=NR$^{80}$)NR$^{78}$-L-Dye;
 —(CH$_2$)$_r$S(CH$_2$)$_p$C(=NOR$^{50}$)NR$^{78}$-L-Dye; —(CH$_2$)$_r$S(CH$_2$)$_p$C(=NNR$^{78}$R$^{79}$)NR$^{78}$-L-Dye;
 —(CH$_2$)$_r$S(CH$_2$)$_m$NR$^{80}$C(=NR$^{80}$)NR$^{78}$-L-Dye;
 —(CH$_2$)$_r$S(CH$_2$)$_m$N=C(NR$^{78}$R$^{80}$)NR$^{79}$-L-Dye;
 —(CH$_2$)$_r$S(CH$_2$)$_p$C$_6$H$_4$CNR$^{78}$-L-Dye; —(CH$_2$)$_r$S(CH$_2$)$_p$C$_6$H$_4$C(=NR$^{80}$)NR$^{78}$-L-Dye;
 —(CH$_2$)$_r$S(CH$_2$)$_p$C$_6$H$_4$C(=NOR$^{50}$)NR$^{78}$-L-Dye;
 —(CH$_2$)$_r$S(CH$_2$)$_p$C$_6$H$_4$C(=NNR$^{78}$R$^{79}$)NR$^{78}$-L-Dye;
 —(CH$_2$)$_r$S(CH$_2$)$_p$C$_6$H$_4$NR$^{80}$C(=NR$^{80}$)NR$^{78}$-L-Dye;
 —(CH$_2$)$_p$NR$^{80}$CO-L-Dye;
 —(CH$_2$)$_p$NR$^{80}$CO-L-Dye; —(CH$_2$)$_p$NR$^{80}$CONR$^{78}$-L-Dye;
 —(CH$_2$)$_p$C$_6$H$_4$NR$^{80}$CONR$^{78}$-L-Dye; —(CH$_2$)$_m$(CHR$_{61}$)$_s$O-L-Dye; —(CH$_2$)$_p$COO-L-Dye;
 —(CH$_2$)$_m$(CHR$_{61}$)$_s$S-L-Dye; —(CH$_2$)$_p$CONR$^{78}$-L-Dye;
 —(CH$_2$)$_p$NR$^{80}$CONR$^{78}$-L-Dye;
 —(CH$_2$)$_p$C$_6$H$_4$CONR$^{78}$-L-Dye; or —(CH$_2$)$_p$C$_6$H$_4$NR$^{80}$CONR$^{78}$-L-Dye;

with the proviso that in said chain of 14 amino acid residues Z, the amino acid residues in positions 1 to 14 are:
 P1: of type C, or of type D, or of type E, or of type F, or of type LD, or the residue is Gly;
 P2: of type E, or of type F, or of type I, or of type D, or of type LD;
 P3: of type E, or of type F; or of type D, or of type C, or type LD, or the residue is Gly or Pro;
 P4: of type D, or of type C or of type F, or of type E, or of type LD;
 P5: of type E, or of type F, or of type C, or of type LD;
 P6: of type C, or of type D, or of type F, or of type LD, or the residue is Gly or Pro;
 P7: of type C, or of type D, or of Type LD, or of formula -A-CO—, or the residue is Gly or Pro;
 P8: of type E, or of Type F, or of type D, or of Type LD, or of formula B-CO—, or the residue is Pro;
 P9: of type F, or of type E, or of type D, or of Type LD, or the residue is Pro;
 P10: of type F, or of type D, or of type C or of type LD;
 P11: of type D, or of type C, or of type F, or of type E, or of type LD, or the residue is Pro;
 P12: of type C, or of type D, or of type E, or of type F, or of type LD;
 P13: of type F, or of type E, or of type LD, or the residue is Gly or Pro;
 P14: or of type F, or of type E, or of type LD; or
 P2 and P13 and/or P4 and P11, taken together, can form a group of type H; at P4, P7, P8 and P11 D-isomers being possible;
with the further proviso that the molecule contains at least one "Dye" moiety;
and pharmaceutically acceptable salts thereof.

In accordance with the present invention these dye-conjugates of O-hairpin peptidomimetics can be prepared by a process which comprises
(a) coupling an appropriately functionalized solid support with an appropriately N-protected derivative of that amino acid which in the desired end-product is in position 6, 7 or 8, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d) removing the N-protecting group from the product thus obtained;

(e) repeating steps (c) and (d) until the N-terminal amino acid residue has been introduced;

(f) coupling the product thus obtained with a compound of the general formula

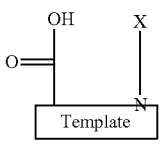

II wherein

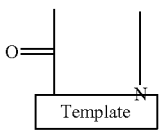

is as defined above and X is an N-protecting group or, alternatively, if

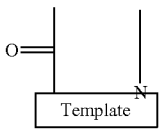

is to be group (a1) or (a2), above, (fa) coupling the product obtained in step (e) with an appropriately N-protected derivative of an amino acid of the general formula

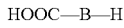   HOOC—B—H   III or

   HOOC-A-H   IV wherein B and A are as defined above, any functional group which may be present in said N-protected amino acid derivative being likewise appropriately protected;

(fb) removing the N-protecting group from the product thus obtained; and (fc) coupling the product thus obtained with an appropriately N-protected derivative of an amino acid of the above general formula IV and, respectively, III, any functional group which may be present in said N-protected amino acid derivative being likewise appropriately protected;

(g) removing the N-protecting group from the product obtained in step (f) or (fc);

(h) coupling the product thus obtained with an appropriately N-protected derivative of that amino acid which in the desired end-product is in position 14, any functional group which may be present in said N-protected amino acid derivative being likewise appropriately protected;

(i) removing the N-protecting group from the product thus obtained;

(j) coupling the product thus obtained with an appropriately N-protected derivative of that amino acid which in the desired end-product is one position farther away from position 14, any functional group which may be present in said N-protected amino acid derivative being likewise appropriately protected;

(k) removing the N-protecting group from the product thus obtained;

(l) repeating steps (j) and (k) until all amino acid residues have been introduced;

(m) if desired, selectively deprotecting one or several protected functional group(s) present in the molecule and appropriately substituting the reactive group(s) thus liberated, if required by attaching one or several residues of formula -L-Dye;

(n) if desired, forming one or two interstrand linkages between side-chains of appropriate amino acid residues at opposite positions of the β-strand region;

(o) detaching the product thus obtained from the solid support;

(p) cyclizing the product cleaved from the solid support;

(q) removing any protecting groups present on functional groups of any members of the chain of amino acid residues and, if desired, any protecting group(s) which may in addition be present in the molecule; and (r) if required, attaching one or several residues of formula -L-Dye; and (s) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

Alternatively, the peptidomimetics of the present invention can be prepared by (a') coupling an appropriately functionalized solid support with a compound of the general formula

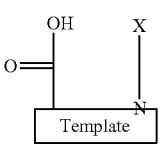

II wherein

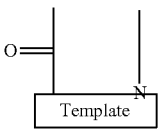

is as defined above and X is an N-protecting group or, alternatively, if

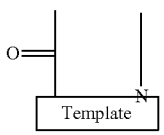

is to be group (a1) or (a2), above,
(a'a) coupling said appropriately functionalized solid support with an appropriately N-protected derivative of an amino acid of the general formula

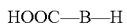          III or

          IV wherein B and A are as defined above, any functional group which may be present in said N-protected amino acid derivative being likewise appropriately protected;
(a'b) removing the N-protecting group from the product thus obtained; and
(a'c) coupling the product thus obtained with an appropriately N-protected derivative of an amino acid of the above general formula IV and, respectively, III, any functional group which may be present in said N-protected amino acid derivative being likewise appropriately protected;
(b') removing the N-protecting group from the product obtained in step (a'), or (a'c);
(c') coupling the product thus obtained with an appropriately N-protected derivative of that amino acid which in the desired end-product is in position 14, any functional group which may be present in said N-protected amino acid derivative being likewise appropriately protected;
(d') removing the N-protecting group from the product thus obtained;
(e') coupling the product thus obtained with an appropriately N-protected derivative of that amino acid which in the desired end-product is one position farther away from position 14, any functional group which may be present in said N-protected amino acid derivative being likewise appropriately protected;
(f') removing the N-protecting group from the product thus obtained;
(g') repeating steps (e') and (f) until all amino acid residues have been introduced;
(h') if desired, selectively deprotecting one or several protected functional group(s) present in the molecule and appropriately substituting the reactive group(s) thus liberated, if required by attaching one or several residues of formula -L-Dye;
(i') if desired, forming one or two interstrand linkages between side-chains of appropriate amino acid residues at opposite positions of the β-strand region;
(j') detaching the product thus obtained from the solid support;
(k') cyclizing the product cleaved from the solid support;
(l') removing any protecting groups present on functional groups of any members of the chain of amino acid residues and, if desired, any protecting group(s) which may in addition be present in the molecule; and
(m') if required, attaching one or several residues of formula -L-Dye; and
(n') if desired, converting the product thus obtained into a pharmaceutically acceptable salt or pharmaceutically acceptable salt or converting a pharmaceutically acceptable, or unacceptable, salt thus obtained into the corresponding free compound of formula I or into a different, pharmaceutically acceptable, salt.

The dye-conjugates of the peptidomimetics of the present invention can also be enantiomers of the compounds of formula I. These enantiomers can be prepared by a modification of the above processes in which enantiomers of all chiral starting materials are used.

As used in this description, the term "alkyl", taken alone or in combinations, designates saturated, straight-chain or branched hydrocarbon radicals having up to 24 preferably up to 12, carbon atoms wherein the hydrogens may be substituted by Br, Cl, F. Similarly, the term "alkenyl" designates straight chain or branched hydrocarbon radicals having up to 24, preferably up to 12, carbon atoms and containing at least one or, depending on the chain length, up to four olefinic double bonds wherein the hydrogens may be substituted by Br, Cl, F. The term "lower" designates radicals and compounds having up to 6 carbon atoms. Thus, for example, the term "lower alkyl" designates saturated, straight-chain or branched hydrocarbon radicals having up to 6 carbon atoms, such as methyl, ethyl, n-propyl, isopropyl, n-butyl, sec.-butyl, isobutyl, tert.-butyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

The structural element -A-CO— designates amino acid building blocks which in combination with the structural element —B—CO— form templates (a1) and (a2). Templates (a) through (p) constitute building blocks which have an N-terminus and a C-terminus oriented in space in such a way that the distance between those two groups may lie between 4.0-5.5A. A peptide chain Z is linked to the C-terminus and the N-terminus of the templates (a) through (p) via the corresponding N- and C-termini so that the template and the chain form a cyclic structure such as that depicted in formula I. In a case as here where the distance between the N. and C-termini of the template lies between 4.0-5.5A the template will induce the H-bond network necessary for the formation of a β-hairpin conformation in the peptide chain Z. Thus template and peptide chain form a β-hairpin mimetic.

The β-hairpin conformation is highly relevant for the CXCR4 antagonizing activity of the β-hairpin mimetics of the present invention. The β-hairpin stabilizing conformational properties of the templates (a) through (p) play a key role not only for the selective CXCR4 antagonizing activity but also for the synthetic processes defined hereinabove, as incorporation of the templates at the beginning or near the middle of the linear protected peptide precursors enhances cyclization yields significantly.

Building blocks A1-A69 belong to a class of amino acids wherein the N-terminus is a secondary amine forming part of a ring. Among the genetically encoded amino acids only proline falls into this class. The configuration of building block A1 through A69 is (D), and they are combined with a building block —B—CO— of (L)-configuration. Preferred combinations for templates (a1) are -$^D$A1-CO—$^L$B—CO— to $^D$A69-CO—$^L$B—CO—. Thus, for example, $^D$Pro-$^L$Pro constitutes the prototype of templates (a1). Less preferred, but possible are combinations -$^L$A1-CO—$^D$B—CO— to $^L$A69-CO—$^D$B—CO— forming templates (a2). Thus, for example, $^L$Pro-$^D$Pro constitutes the prototype of template (a2).

It will be appreciated that building blocks -A1-CO— to -A69-CO— in which A has (D)-configuration, are carrying a group $R^1$ at the α-position to the N-terminus. The preferred values for $R^1$ are H and lower alkyl with the most preferred values for $R^1$ being H and methyl. It will be recognized by those skilled in the art, that A1-A69 are shown in (D)-configuration which, for $R^1$ being H and methyl, corresponds to the (R)-configuration. Depending on the priority of other values for $R^1$ according to the Cahn, Ingold and Prelog-rules, this configuration may also have to be expressed as (S).

In addition to $R^1$, building blocks -A1-CO— to -A69-CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^{17}$ are:

$R^2$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl; —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; $CF_3$; lower alkyl; lower alkenyl; or lower alkoxy).

$R^3$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^4$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_mN(R^{20})COR^{64}$(where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^5$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: where H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$(where: $R^{20}$: H; or lower alkyl; $R^{64}$: alkyl; alkenyl; aryl; and aryl-lower alkyl; heteroaryl-lower alkyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where R$^{57}$: H; or lower alkyl); —$(CH_2)_o$PO(OR$^{60}$)$_2$ (where R$^{60}$: lower alkyl; or lower alkenyl); —$(CH_2)_o$SO$_2$R$^{62}$ (where R$^{62}$: lower alkyl; or lower alkenyl); or —$(CH_2)_q$C$_6$H$_4$R$^8$ (where R$^8$: H; F; Cl; CF$_3$; lower alkyl; lower alkenyl; or lower alkoxy).

R$^6$: H; lower alkyl; lower alkenyl; —$(CH_2)_o$OR$^{55}$ (where R$^{55}$: lower alkyl; or lower alkenyl); —$(CH_2)_o$SR$^{56}$ (where R$^{56}$: lower alkyl; or lower alkenyl); —$(CH_2)_o$NR$^{33}$R$^{34}$ (where R$^{33}$: lower alkyl; or lower alkenyl; R$^{34}$: H; or lower alkyl; or R$^{33}$ and R$^{34}$ taken together form:
—$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where R$^{57}$: H; or lower alkyl); —$(CH_2)_o$OCONR$^{33}$R$^{75}$ (where R$^{33}$: H; or lower alkyl; or lower alkenyl; R$^{75}$: lower alkyl; or R$^{33}$ and R$^{75}$ taken together form: —$(CH_2)_{2-6}$—; —$(CH_2)_2$O$(CH_2)_2$—; —$(CH_2)_2$S$(CH_2)_2$—; or
—$(CH_2)_2$NR$^{57}$$(CH_2)_2$—; where R$^{57}$: H; or lower alkyl); —$(CH_2)_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —$(CH_2)_{2-6}$—; —$(CH_2)_2$O$(CH_2)_2$—; —$(CH_2)_2$S$(CH_2)_2$—; or
—$(CH_2)_2$NR$^{57}$$(CH_2)_2$—; where R$^{57}$: H; or lower alkyl); —$(CH_2)_o$N(R$^{20}$)COR$^{64}$ (where: R$^{20}$: H; or lower alkyl; R$^{64}$: lower alkyl; or lower alkenyl); —$(CH_2)_o$COOR$^{57}$ (where R$^{57}$: lower alkyl; or lower alkenyl); —$(CH_2)_o$CONR$^{58}$R$^{59}$ (where R$^{58}$: lower alkyl; or lower alkenyl; and R$^{59}$: H; or lower alkyl; or R$^{58}$ and R$^{59}$ taken together form: —$(CH_2)_{2-6}$—; —$(CH_2)_2$O$(CH_2)_2$—;
—$(CH_2)_2$S$(CH_2)_2$—; or —$(CH_2)_2$NR$^{57}$$(CH_2)_2$—; where R$^{57}$: H; or lower alkyl); —$(CH_2)_o$PO(OR$^{60}$)$_2$ (where R$^{60}$: lower alkyl; or lower alkenyl); —$(CH_2)_o$SO$_2$R$^{62}$ (where R$^{62}$: lower alkyl; or lower alkenyl); or —$(CH_2)_q$C$_6$H$_4$R$^8$ (where R$^8$: H; F; Cl; CF$_3$; lower alkyl; lower alkenyl; or lower alkoxy).

R$^7$: lower alkyl; lower alkenyl; —$(CH_2)_q$OR$^{55}$ (where R$^{55}$: lower alkyl; or lower alkenyl); —$(CH_2)_q$SR$^{56}$ (where R$^{56}$: lower alkyl; or lower alkenyl); —$(CH_2)_q$NR$^{33}$R$^{34}$ (where R$^{33}$: lower alkyl; or lower alkenyl; R$^{34}$: H; or lower alkyl; or R$^{33}$ and R$^{34}$ taken together form:
—$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where R$^{57}$: H; or lower alkyl); —$(CH_2)_q$CONR$^{33}$R$^{75}$ (where R$^{33}$: H; or lower alkyl; or lower alkenyl; R$^{75}$: lower alkyl; or R$^{33}$ and R$^{75}$ taken together form: —$(CH_2)_{2-6}$—; —$(CH_2)_2$O$(CH_2)_2$—; —$(CH_2)_2$S$(CH_2)_2$—; or
—$(CH_2)_2$NR$^{57}$$(CH_2)_2$—; where R$^{57}$: H; or lower alkyl); —$(CH_2)_q$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —$(CH_2)_{2-6}$—; —$(CH_2)_2$O$(CH_2)_2$—; —$(CH_2)_2$S$(CH_2)_2$—; or
—$(CH_2)_2$NR$^{57}$$(CH_2)_2$—; where R$^{57}$: H; or lower alkyl); —$(CH_2)_q$N(R$^{20}$)COR$^{64}$ (where: R$^{20}$: H; or lower alkyl; R$^{64}$: lower alkyl; or lower alkenyl); —$(CH_2)_r$COOR$^{57}$ (where R$^{57}$: lower alkyl; or lower alkenyl); —$(CH_2)_q$CONR$^{58}$R$^{59}$ (where R$^{58}$: lower alkyl; or lower alkenyl; and R$^{59}$: H; or lower alkyl; or R$^{58}$ and R$^{59}$ taken together form: —$(CH_2)_{2-6}$—; —$(CH_2)_2$O$(CH_2)_2$—;
—$(CH_2)_2$S$(CH_2)_2$—; or —$(CH_2)_2$NR$^{57}$$(CH_2)_2$—; where R$^{57}$: H; or lower alkyl); —$(CH_2)_r$PO(OR$^{60}$)$_2$ (where R$^{60}$: lower alkyl; or lower alkenyl); —$(CH_2)_r$SO$_2$R$^{62}$ (where R$^{62}$: lower alkyl; or lower alkenyl); or —$(CH_2)_q$C$_6$H$_4$R$^8$ (where R$^8$: H; F; Cl; CF$_3$; lower alkyl; lower alkenyl; or lower alkoxy).

R$^8$: H; F; Cl; CF$_3$; lower alkyl; lower alkenyl; —$(CH_2)_o$OR$^{55}$ (where R$^{55}$: lower alkyl; or lower alkenyl); —$(CH_2)_o$SR$^{56}$ (where R$^{56}$: lower alkyl; or lower alkenyl); —$(CH_2)_o$NR$^{33}$R$^{34}$ (where R$^{33}$: lower alkyl; or lower alkenyl; R$^{34}$: H; or lower alkyl; or R$^{33}$ and R$^{34}$ taken together form:
—$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where R$^{57}$: H; or lower alkyl); —$(CH_2)_o$OCONR$^{33}$R$^{75}$ (where R$^{33}$: H; or lower alkyl; or lower alkenyl; R$^{75}$: lower alkyl; or R$^{33}$ and R$^{75}$ taken together form: —$(CH_2)_{2-6}$—; —$(CH_2)_2$O$(CH_2)_2$—;
—$(CH_2)_2$S$(CH_2)_2$—; or —$(CH_2)_2$NR$^{57}$$(CH_2)_2$—; where R$^{57}$: H; or lower alkyl);
—$(CH_2)_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form:
—$(CH_2)_{2-6}$—;
—$(CH_2)_2$O$(CH_2)_2$—; —$(CH_2)_2$S$(CH_2)_2$—; or —$(CH_2)_2$NR$^{57}$$(CH_2)_2$—; where R$^{57}$: H; or lower alkyl);
—$(CH_2)_o$N(R$^{20}$)COR$^{64}$ (where: R$^{20}$: H; or lower alkyl; R$^{64}$: lower alkyl; or lower alkenyl);
—$(CH_2)_o$COOR$^{57}$ (where R$^{57}$: lower alkyl; or lower alkenyl); —$(CH_2)_o$CONR$^{58}$R$^{59}$ (where R$^{58}$: lower alkyl; or lower alkenyl; and R$^{59}$: H; or lower alkyl; or R$^{58}$ and R$^{59}$ taken together form:
—$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where R$^{57}$: H; or lower alkyl); —$(CH_2)_o$PO(OR$^{60}$)$_2$ (where R$^{60}$: lower alkyl; or lower alkenyl); —$(CH_2)_o$SO$_2$R$^{62}$ (where R$^{62}$: lower alkyl; or lower alkenyl); or —$(CH_2)_q$C$_6$H$_4$R$^8$ (where R$^8$: H; F; Cl; CF$_3$; lower alkyl; lower alkenyl; or lower alkoxy).

R$^9$: lower alkyl; lower alkenyl; —$(CH_2)_o$OR$^{55}$ (where R$^{55}$: lower alkyl; or lower alkenyl); —$(CH_2)_o$SR$^{56}$ (where R$^{56}$: lower alkyl; or lower alkenyl); —$(CH_2)_o$NR$^{33}$R$^{34}$ (where R$^{33}$: lower alkyl; or lower alkenyl; R$^{34}$: H; or lower alkyl; or R$^{33}$ and R$^{34}$ taken together form:
—$(CH_2)_{2-6}$—; —$(CH_2)_2$O$(CH_2)_2$—; —$(CH_2)_2$S$(CH_2)_2$—; or —$(CH_2)_2$NR$^{57}$$(CH_2)_2$—; where R$^{57}$: H; or lower alkyl); —$(CH_2)_o$OCONR$^{33}$R$^{75}$ (where R$^{33}$: H; or lower alkyl; or lower alkenyl; R$^{75}$: lower alkyl; or R$^{33}$ and R$^{75}$ taken together form: —$(CH_2)_{2-6}$—; —$(CH_2)_2$O$(CH_2)_2$—; —$(CH_2)_2$S$(CH_2)_2$—; or
—$(CH_2)_2$NR$^{57}$$(CH_2)_2$—; where R$^{57}$: H; or lower alkyl); —$(CH_2)_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —$(CH_2)_{2-6}$—; —$(CH_2)_2$O$(CH_2)_2$—; —$(CH_2)_2$S$(CH_2)_2$—; or
—$(CH_2)_2$NR$^{57}$$(CH_2)_2$—; where R$^{57}$: H; or lower alkyl); —$(CH_2)_o$N(R$^{20}$)COR$^{64}$ (where: R$^{20}$: H; or lower alkyl; R$^{64}$: lower alkyl; or lower alkenyl); —$(CH_2)_o$COOR$^{57}$ (where R$^{57}$: lower alkyl; or lower alkenyl); —$(CH_2)_o$CONR$^{58}$R$^{59}$ (where R$^{58}$: lower alkyl; or lower alkenyl; and R$^{59}$: H; or lower alkyl; or R$^{58}$ and R$^{59}$ taken together form: —$(CH_2)_{2-6}$—; —$(CH_2)_2$O$(CH_2)_2$—;
—$(CH_2)_2$S$(CH_2)_2$—; or —$(CH_2)_2$NR$^{57}$$(CH_2)_2$—; where R$^{57}$: H; or lower alkyl); —$(CH_2)_o$PO(OR$^{60}$)$_2$ (where R$^{60}$: lower alkyl; or lower alkenyl); —$(CH_2)_o$SO$_2$R$^{62}$ (where R$^{62}$: lower alkyl; or lower alkenyl); or —$(CH_2)_q$C$_6$H$_4$R$^8$ (where R$^8$: H; F; Cl; CF$_3$; lower alkyl; lower alkenyl; or lower alkoxy).

R$^{10}$: lower alkyl; lower alkenyl; —$(CH_2)_o$OR$^{55}$ (where R$^{55}$: lower alkyl; or lower alkenyl); —$(CH_2)_o$SR$^{56}$ (where R$^{56}$: lower alkyl; or lower alkenyl); —$(CH_2)_o$NR$^{33}$R$^{34}$ (where R$^{33}$: lower alkyl; or lower alkenyl; R$^{34}$: H; or lower alkyl; or R$^{33}$ and R$^{34}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$(where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{11}$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{12}$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_r$COOR$^{57}$ (where R$^{57}$: lower alkyl; or lower alkenyl); —(CH$_2$)$_r$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{66}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{13}$: lower alkyl; lower alkenyl; —(CH$_2$)$_q$OR$^{55}$ (where R$^{55}$: lower alkyl; or lower alkenyl); —(CH$_2$)$_q$SR$^{56}$ (where R$^{56}$: lower alkyl; or lower alkenyl); —(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$N(R$^{20}$)COR$^{64}$ (where: R$^{20}$: H; or lower alkyl; R$^{64}$: lower alkyl; or lower alkenyl); —(CH$_2$)$_r$COO$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{14}$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); —(CH$_2$)$_q$C$_6$H$_4$R$^8$ (where R$^8$: H; F; Cl; CF$_3$; lower alkyl; lower alkenyl; or lower alkoxy).

R$^{15}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); particularly favoured are NR$^{20}$COlower alkyl (R$^{20}$=H; or lower alkyl); —(CH$_2$)$_o$COOR$^{57}$ (where R$^{57}$: lower alkyl; or lower alkenyl);
—(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or
—(CH$_2$)$_4$C$_6$H$_4$R$^8$ (where R$^8$: H; F; Cl; CF$_3$; lower alkyl; lower alkenyl; or lower alkoxy).

R$^{16}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl);
—(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form: —(CH$_2$)$_{2-6}$—; —(CH$_2$)$_2$O(CH$_2$)$_2$—;
—(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{17}$: lower alkyl; lower alkenyl; —(CH$_2$)$_q$OR$^{55}$ (where R$^{55}$: lower alkyl; or lower alkenyl); —(CH$_2$)$_q$SR$^{56}$ (where R$^{56}$: lower alkyl; or lower alkenyl); —(CH$_2$)$_q$NR$^{33}$R$^{34}$ (where R$^{33}$: lower alkyl; or lower alkenyl; R$^{34}$: H; or lower alkyl; or R$^{33}$ and R$^{34}$ taken together form:
—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_q$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_q$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or
—(CH$_2$)$_2$NR$^{57}$(CH$_2$)$_2$—; where R$^{57}$: H; or lower alkyl); —(CH$_2$)$_q$N(R$^{20}$)COR$^{64}$(where: R$^{20}$: H; or lower alkyl; R$^{64}$: lower alkyl; or lower alkenyl); —(CH$_2$)$_r$COOR$^{57}$ (where R$^{57}$: lower alkyl; or lower alkenyl); —(CH$_2$)$_q$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—;
—(CH$_2$)$_2$S(CH$_2$)$_2$—; or —(CH$_2$)$_2$NR$^{57}$(CH$_2$)$_2$—; where R$^{57}$: H; or lower alkyl; —(CH$_2$)$_r$PO(OR$^{60}$)$_2$ (where R$^{60}$: lower alkyl; or lower alkenyl); —(CH$_2$)$_r$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

Among the building blocks A1 to A69 the following are preferred: A5 with R$^2$ being H, A8, A22, A25, A38 with R$^2$ being H, A42, A47, and A50. Most preferred are building blocks of type A8':

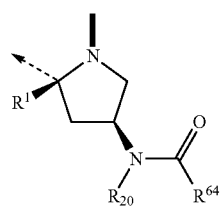

A8' wherein R$^{20}$ is H or lower alkyl; and R$^{64}$ is alkyl; alkenyl; aryl; aryl-lower alkyl; or heteroaryl-lower alkyl; especially those wherein R$^{64}$ is n-hexyl (A8'-1); n-heptyl (A8'-2); 4-(phenyl)benzyl (A8'-3); diphenylmethyl (A8'-4); 3-amino-propyl (A8'-5); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); and n-nonyl (A8'-20).

Additional preferred values for $R^{64}$ are —[($CH_2$)$_u$—X]$_t$—$CH_3$, wherein X is —O—; —$NR^{20}$—; or —S—; u is 1-3 and t is 1-6, such as $CH_3$—$OCH_2CH_2$—$OCH_2$— and $CH_3$—($OCH_2CH_2$)$_2$—$OCH_2$—.

Building block A70 belongs to the class of open-chain α-substituted α-amino acids, building blocks A71 and A72 to the corresponding β-amino acid analogues and building blocks A73-A104 to the cyclic analogues of A70. Such amino acid derivatives have been shown to constrain small peptides in well defined reverse turn or U-shaped conformations (C. M. Venkatachalam, *Biopolymers*, 1968, 6, 1425-1434; W. Kabsch, C Sander, *Biopolymers* 1983, 22, 2577). Such building blocks or templates are ideally suited for the stabilization of O-hairpin conformations in peptide loops (D. Obrecht, M. Altorfer, J. A. Robinson, "Novel Peptide Mimetic Building Blocks and Strategies for Efficient Lead Finding", *Adv. Med Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A70-CO— to A104-CO— in combination with a building block —B—CO— of L-configuration can efficiently stabilize and induce O-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Miller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Thus, for the purposes of the present invention templates (a1) can also consist of -A70-CO— to A104-CO— where building block A70 to A104 is of either (D)- or (L)-configuration, in combination with a building block —B—CO— of (L)-configuration.

Preferred values for $R^{20}$ in A70 to A104 are H or lower alkyl with methyl being most preferred. Preferred values for $R^{18}$, $R^{19}$ and $R^{21}$-$R^{29}$ in building blocks A70 to A104 are the following:

$R^{18}$: lower alkyl.

$R^{19}$: lower alkyl; lower alkenyl; —($CH_2$)$_p$$OR^{55}$ (where $R^{55}$: lower alkyl; or lower alkenyl); —($CH_2$)$_p$$SR^{56}$ (where $R^{56}$: lower alkyl; or lower alkenyl); —($CH_2$)$_p$$NR^{33}R^{34}$ (where $R^{33}$: lower alkyl; or lower alkenyl; $R^{34}$: H; or lower alkyl; or $R^{33}$ and $R^{34}$ taken together form:
—($CH_2$)$_{2-6}$—; —($CH_2$)$_2$O($CH_2$)$_2$—; —($CH_2$)$_2$S($CH_2$)$_2$—; or —($CH_2$)$_2$$NR^{57}$($CH_2$)$_2$—; where $R^{57}$: H; or lower alkyl); —($CH_2$)$_p$$OCONR^{33}R^{75}$ (where $R^{33}$: H; or lower alkyl; or lower alkenyl; $R^{75}$: lower alkyl; or $R^{33}$ and $R^{75}$ taken together form: —($CH_2$)$_{2-6}$—; —($CH_2$)$_2$O($CH_2$)$_2$—; —($CH_2$)$_2$S($CH_2$)$_2$—; or
—($CH_2$)$_2$$NR^{57}$($CH_2$)$_2$—; where $R^{57}$: H; or lower alkyl); —($CH_2$)$_p$$NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —($CH_2$)$_{2-6}$—; —($CH_2$)$_2$O($CH_2$)$_2$—; —($CH_2$)$_2$S($CH_2$)$_2$—; or
—($CH_2$)$_2$$NR^{57}$($CH_2$)$_2$—; where $R^{57}$: H; or lower alkyl); —($CH_2$)$_p$$N(R^{20})COR^{64}$ (where: $R^{20}$: H; or lower alkyl; $R^{64}$: lower alkyl; or lower alkenyl); —($CH_2$)$_p$$COOR^{57}$ (where $R^{57}$: lower alkyl; or lower alkenyl); —($CH_2$)$_p$$CONR^{58}R^{59}$ (where $R^{58}$: lower alkyl; or lower alkenyl; and $R^{59}$: H; or lower alkyl; or $R^{58}$ and $R^{59}$ taken together form: —($CH_2$)$_{2-6}$—; —($CH_2$)$_2$O($CH_2$)$_2$—;
—($CH_2$)$_2$S($CH_2$)$_2$—; or —($CH_2$)$_2$$NR^{57}$($CH_2$)$_2$—; where $R^{57}$: H; or lower alkyl); —($CH_2$)$_o$$PO(OR^{60})_2$ (where $R^{60}$: lower alkyl; or lower alkenyl); —($CH_2$)$_p$$SO_2R^{62}$ (where $R^{62}$: lower alkyl; or lower alkenyl); or —($CH_2$)$_o$$C_6H_4R^8$ (where $R^8$: H; F; Cl; $CF_3$; lower alkyl; lower alkenyl; or lower alkoxy).

$R^{21}$: H; lower alkyl; lower alkenyl; —($CH_2$)$_o$$OR^{55}$ (where $R^{55}$: lower alkyl; or lower alkenyl); —($CH_2$)$_o$$SR^{56}$ (where $R^{56}$: lower alkyl; or lower alkenyl); —($CH_2$)$_o$$NR^{33}R^{34}$ (where $R^{33}$: lower alkyl; or lower alkenyl; $R^{34}$: H; or lower alkyl; or $R^{33}$ and $R^{34}$ taken together form:
—($CH_2$)$_{2-6}$—; —($CH_2$)$_2$O($CH_2$)$_2$—; —($CH_2$)$_2$S($CH_2$)$_2$—; or —($CH_2$)$_2$$NR^{57}$($CH_2$)$_2$—; where $R^{57}$: H; or lower alkyl); —($CH_2$)$_o$$OCONR^{33}R^{75}$ (where $R^{33}$: H; or lower alkyl; or lower alkenyl; $R^{75}$: lower alkyl; or $R^{33}$ and $R^{75}$ taken together form: —($CH_2$)$_{2-6}$—; —($CH_2$)$_2$O($CH_2$)$_2$—; —($CH_2$)$_2$S($CH_2$)$_2$—; or
—($CH_2$)$_2$$NR^{57}$($CH_2$)$_2$—; where $R^{57}$: H; or lower alkyl); —($CH_2$)$_o$$NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —($CH_2$)$_{2-6}$—; —($CH_2$)$_2$O($CH_2$)$_2$—; —($CH_2$)$_2$S($CH_2$)$_2$—; or
—($CH_2$)$_2$$NR^{57}$($CH_2$)$_2$—; where $R^{57}$: H; or lower alkyl); —($CH_2$)$_o$$N(R^{20})COR^{64}$ (where: $R^{20}$: H; or lower alkyl; $R^{64}$: lower alkyl; or lower alkenyl); —($CH_2$)$_o$$COOR^{57}$ (where $R^{57}$: lower alkyl; or lower alkenyl); —($CH_2$)$_o$$CONR^{58}R^{59}$ (where $R^{58}$: lower alkyl, or lower alkenyl; and $R^{59}$: H; lower alkyl; or $R^{58}$ and $R^{59}$ taken together form: —($CH_2$)$_{2-6}$—; —($CH_2$)$_2$O($CH_2$)$_2$—;
—($CH_2$)$_2$S($CH_2$)$_2$—; or —($CH_2$)$_2$$NR^{57}$($CH_2$)$_2$—; where $R^{57}$: H; or lower alkyl); —($CH_2$)$_o$$PO(OR^{60})_2$ (where $R^{60}$: lower alkyl; or lower alkenyl); —($CH_2$)$_o$$SO_2R^{62}$ (where $R^{62}$: lower alkyl; or lower alkenyl); or ($CH_2$)$_q$$C_6H_4R^8$ (where $R^8$: H; F; Cl; $CF_3$; lower alkyl; lower alkenyl; or lower alkoxy).

$R^{22}$: lower alkyl; lower alkenyl; —($CH_2$)$_o$$OR^{55}$ (where $R^{55}$: lower alkyl; or lower alkenyl); —($CH_2$)$_o$$SR^{56}$ (where $R^{56}$: lower alkyl; or lower alkenyl); —($CH_2$)$_o$$NR^{33}R^{34}$ (where $R^{33}$: lower alkyl; or lower alkenyl; $R^{34}$: H; or lower alkyl; or $R^{33}$ and $R^{34}$ taken together form:
—($CH_2$)$_{2-6}$—; —($CH_2$)$_2$O($CH_2$)$_2$—; —($CH_2$)$_2$S($CH_2$)$_2$—; or —($CH_2$)$_2$$NR^{57}$($CH_2$)$_2$—; where $R^{57}$: H; or lower alkyl); —($CH_2$)$_o$$OCONR^{33}R^{75}$ (where $R^{33}$: H; or lower alkyl; or lower alkenyl; $R^{75}$: lower alkyl; or $R^{33}$ and $R^{75}$ taken together form: —($CH_2$)$_{2-6}$—; —($CH_2$)$_2$O($CH_2$)$_2$—; —($CH_2$)$_2$S($CH_2$)$_2$—; or
—($CH_2$)$_2$$NR^{57}$($CH_2$)$_2$—; where $R^{57}$: H; or lower alkyl); —($CH_2$)$_o$$NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —($CH_2$)$_{2-6}$—; —($CH_2$)$_2$O($CH_2$)$_2$—; —($CH_2$)$_2$S($CH_2$)$_2$—; or
—($CH_2$)$_2$$NR^{57}$($CH_2$)$_2$—; where $R^{57}$: H; or lower alkyl); —($CH_2$)$_o$$N(R^{20})COR^{64}$(where: $R^{20}$: H; or lower alkyl; $R^{64}$: lower alkyl; or lower alkenyl); —($CH_2$)$_o$$COOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{69})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{23}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are $NR^{20}CO$lower alkyl ($R^{20}$=H; or lower alkyl); —$(CH_2)_oCOOR^{57}$ (where $R^{57}$: lower alkyl; or lower alkenyl);
—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or
—$(CH_2)_qC_6H_4R^8$ (where $R^8$: H; F; $CF_3$; lower alkyl; lower alkenyl; or lower alkoxy);

$R^{24}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are $NR^{20}CO$lower alkyl ($R^{20}$=H; or lower alkyl); —$(CH_2)_oCOOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy);

$R^{25}$: H; lower alkyl; lower alkenyl; —$(CH_2)_mOR^{55}$ (where $R^{55}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mN(R^{20})COR^{64}$ (where: $R^{20}$: H; or lower alkyl; $R^{64}$: lower alkyl; or lower alkenyl);
—$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{26}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mNR^{20}CONR^{33}R^{82}$ (where H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mN(R^{20})COR^{64}$ (where: $R^{20}$: H; or lower alkyl; $R^{64}$: lower alkyl; or lower alkenyl);
—$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{69})_2$ (where $R^{60}$: lower alkyl; or lower alkenyl); —$(CH_2)_oSO_2R^{62}$ (where $R^{62}$:

lower alkyl; or lower alkenyl); or —$(CH_2)_qC_6H_4R^8$ (where $R^8$: H; F; Cl; $CF_3$; lower alkyl; lower alkenyl; or lower alkoxy).

Alternatively, $R^{25}$ and $R^{26}$ taken together can be —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{27}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$"; or
—$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{28}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$(where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{20}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$(where: $R^{20}$: H; or lower alkyl; $R^{64}$: lower alkyl; or lower alkenyl); particularly favored are $NR^{20}COlower$-alkyl ($R^{20}$=H; or lower alkyl); —$(CH_2)_oCOOR^{57}$ (where $R^{57}$: lower alkyl; or lower alkenyl);
—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or
—$(CH_2)_qC_6H_4R^8$ (where $R^8$: H; F; Cl; $CF_3$; lower alkyl; lower alkenyl; or lower alkoxy).

For templates (b) to (p), such as (b1) and (c1), the preferred values for the various symbols are the following:

$R^8$: H; F; Cl; $CF_3$; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;
—$(CH_2)_2S(CH_2)_2$—; or —$(CH_2)_2NR^{57}(CH_2)_2$—; where $R^{57}$: H; or lower alkyl);
—$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form:
—$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_oN(R^{20})COR^{64}$ (where: $R^{20}$: H; or lower alkyl; $R^{64}$: lower alkyl; or lower alkenyl);
—$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{20}$: H; or lower alkyl.

$R^{30}$: H, methyl.

$R^{31}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_rC_6H_4R^8$ (where $R^8$: H; F; Cl; $CF_3$; lower alkyl; lower alkenyl; or lower alkoxy); most preferred is —$CH_2CONR^{58}R^{59}$ ($R^{58}$: H; or lower alkyl; $R^{59}$: lower alkyl; or lower alkenyl).

$R^{32}$: H, methyl.

$R^{33}$: lower alkyl; lower alkenyl; —$(CH_2)_mOR^{55}$ (where $R^{55}$: lower alkyl; or lower alkenyl); —$(CH_2)_mNR^{34}R^{63}$ (where $R^{34}$: lower alkyl; or lower alkenyl; $R^{63}$: H; or lower alkyl; or $R^{34}$ and $R^{63}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{75}R^{82}$ (where $R^{75}$: lower alkyl; or lower alkenyl; $R^{82}$: H; or lower alkyl; or $R^{75}$ and $R^{82}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{78}R^{82}$ (where $R^{20}$: H; or lower lower alkyl; $R^{78}$: H; or lower alkyl; or lower alkenyl; $R^{82}$: H; or lower alkyl; or $R^{78}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{34}$: H; or lower alkyl.

$R^{35}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{36}$: lower alkyl; lower alkenyl; or aryl-lower alkyl.

$R^{37}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{38}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_p$N(R$^{20}$)COR$^{64}$ (where: R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{39}$: H; lower alkyl; lower alkenyl; —(CH$_2$)$_m$OR$^{55}$ (where R$^{55}$: lower alkyl; or lower alkenyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl).

R$^{40}$: lower alkyl; lower alkenyl; or aryl-lower alkyl.

R$^{41}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_p$N(R$^{20}$)COR$^{64}$ (where: R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alley; or R$^{58}$ and R$^{59}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{69}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{42}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl;

or lower alkenyl; R$^{75}$: lower alkyl; or R$^{33}$ and R$^{75}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_p$N(R$^{20}$)COR$^{64}$ (where: R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{69}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{43}$: H; lower alkyl; lower alkenyl; —(CH$_2$)$_m$OR$^{55}$ (where R$^{55}$: lower alkyl; or lower alkenyl); —(CH$_2$)$_m$SR$^{56}$ (where R$^{56}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—;

—(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{44}$: lower alkyl; lower alkenyl; —(CH$_2$)$_p$OR$^{55}$ (where R$^{55}$: lower alkyl; or lower alkenyl); —(CH$_2$)$_p$SR$^{56}$ (where R$^{56}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{78}$ taken together form: —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower lower alkyl; R$^{33}$: H; or lower alkyl; or lower alkenyl;

$R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_oC_6H_4R^8$ (where $R^8$: H; F; Cl; $CF_3$; lower alkyl; lower alkenyl; or lower alkoxy).

$R^{45}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_zNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_zN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{46}$: H; lower alkyl; lower alkenyl; —$(CH_2)_sOR^{55}$ (where $R^{55}$: lower alkyl; or lower alkenyl); —$(CH_2)_sSR^{56}$ (where $R^{56}$: lower alkyl; or lower alkenyl); —$(CH_2)_sNR^{33}R^{34}$ (where $R^{33}$: lower alkyl; or lower alkenyl; $R^{34}$: H; or lower alkyl; or $R^{33}$ and $R^{34}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_sNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{47}$: H; or $OR^{55}$ (where $R^{55}$: lower alkyl; or lower alkenyl).

$R^{48}$: H; or lower alkyl.

$R^{49}$: H; lower alkyl; —$(CH_2)_oCOOR^{57}$ (where $R^{57}$: lower alkyl; or lower alkenyl);
—$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); or $(CH_2)_sC_6H_4R^8$ (where $R^8$: H; F; Cl; $CF_3$; lower alkyl; lower alkenyl; or lower alkoxy).

$R^{50}$: H; methyl.

$R^{51}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mN(R^{20})COR^{64}$ (where: $R^{20}$: H; or lower alkyl; $R^{64}$: lower alkyl; or lower alkenyl);
—$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form:
—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{52}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or
—$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—;
—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);
—$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form:
—$(CH_2)_{2-6}$—;
—$(CH_2)_2O(CH_2)_2$—; —$(CH_2)_2S(CH_2)_2$—; or —$(CH_2)_2NR^{57}(CH_2)_2$—; $R^{57}$: H; or lower alkyl);
—$(CH_2)_mN(R^{20})COR^{64}$ (where: $R^{20}$: H; or lower alkyl; $R^{64}$: lower alkyl; or lower alkenyl);
—$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_sC_6H_4R^8$ (where $R^8$: H; F; Cl; $CF_3$; lower alkyl; lower alkenyl; or lower alkoxy).

$R^{53}$: H; lower alkyl; lower alkenyl; —$(CH_2)_mOR^{55}$ (where $R^{55}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{54}$: lower alkyl; lower alkenyl; or aryl-lower alkyl.

Among the building blocks A70 to A104 the following are preferred: A74 with $R^{22}$ being H, A75, A76, A77 with $R^{22}$ being H, A78 and A79.

The building block —B—CO— within templates (a1) and (a2) designates an L-amino acid residue. Preferred values for B are: —$NR^{20}CH(R^{71})$— and enantiomers of groups A5 with $R^2$ being H, A8, A22, A25, A38 with $R^2$ being H, A42, A47, and A50. Most preferred are

| | |
|---|---|
| Ala | L-Alanine |
| Arg | L-Arginine |
| Asn | L-Asparagine |
| Cys | L-Cysteine |
| Gln | L-Glutamine |
| Gly | Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |
| Trp | L-Tryptophan |
| Tyr | L-Tyrosine |
| Val | L-Valine |
| Cit | L-Citrulline |
| Orn | L-Ornithine |
| tBuA | L-t-Butylalanine |
| Sar | Sarcosine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | L-1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | L-N-Acetyllysine |
| Dpr | L-2,3-Diaminopropionic acid |
| A$_2$Bu | L-2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| Pip | L-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methvaline |
| MeLeu | L-N-Methylleucine |
| AmPro | (2S-4R)-4-Amino-pyrrolidine-2-carboxylic acid |
| AmPRO(FHS) | (2S,4R)-4-[6-(5(6)Fluorescein-carboxamido)-hexanamido]-pyrrolidine-2-carboxylic acid |

In addition, the most preferred values for B also include groups of type A8″ of (L)-configuration:

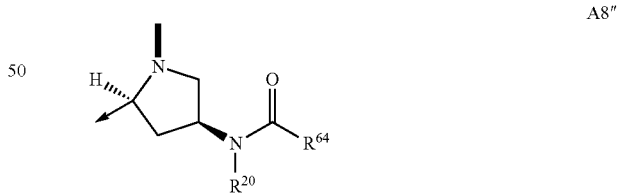

A8″ wherein $R^{20}$ is H or lower alkyl and $R^{64}$ is alkyl; alkenyl; aryl; aryl-lower alkyl; heteroaryl-lower alkyl; or —$[(CH_2)_u—X]_t$—$CH_3$ (where X is —O—; —$NR^{20}$—, or —S—; u is 1-3, and t is 1-6); especially those wherein $R^{64}$ is n-hexyl (A8″-21); n-heptyl (A8″-22); 4-(phenyl)benzyl (A8″-23); diphenylmethyl (A8″-24); 3-aminopropyl (A8″-25); 5-amino-pentyl (A8″-26); methyl (A8″-27); ethyl (A8″-28); isopropyl (A8″-29); isobutyl (A8″-30); n-propyl (A8″-31); cyclohexyl (A8″-32); cyclohexylmethyl (A8″-33); n-butyl (A8″-34); phenyl (A8″-35); benzyl (A8″-36); (3-indolyl)methyl (A8″-

37); 2-(3-indolyl)ethyl (A8"-38); (4-phenyl)phenyl (A8"-39); n-nonyl (A8"-40); $CH_3$—$OCH_2CH_2$—$OCH_2$— (A8"-41) and $CH_3$—$(OCH_2CH_2)_2$—$OCH_2$— (A8"-42).

The peptidic chain Z of the β-hairpin mimetics described herein is generally defined in terms of amino acid residues belonging to one of the following groups:

Group C —$NR^{20}CH(R^{72})CO$—; "hydrophobic: small to medium-sized"

Group D —$NR^{20}CH(R^{73})CO$—; "hydrophobic: large aromatic or heteroaromatic"

Group E —$NR^{20}CH(R^{74})CO$—; "polar-cationic" and "urea-derived"

Group F —$NR^{20}CH(R^{84})CO$—; "polar-non-charged or anionic"

Group LD —$NR^{20}(R^{86})$ "amino acid residue linked to a dye through a direct bond or a linker"

Group H —$NR^{20}$—$CH(CO$—$)$—$(CH_2)_{4-7}$—$CH(CO$—$)$—$NR^{20}$—;
—$NR^{20}$—$CH(CO$—$)$—$(CH_2)_pSS(CH_2)_p$—$CH(CO$—$)$—$NR$—;
—$NR^{20}$—$CH(CO$—$)$—$(—(CH_2)_pNR^{20}CO(CH_2)_p$—$CH(CO$—$)$—$NR^{20}$—; and
—$NR^{20}$—$CH(CO$—$)$—$(—(CH_2)_pNR^{20}CONR^{20}$ $(CH_2)_p$—$CH(CO$—$)$—$NR^{20}$—; "interstrand linkage"

Furthermore, the amino acid residues in chain Z can also be of formula -A-CO— or of formula —B—CO— wherein A and B are as defined above. Finally, Gly can also be an amino acid residue in chain Z, and Pro can be an amino acid residue in chain. Z, too, with the exception of positions where interstrand linkages (H) are possible.

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tetriary amides, alkyl- or aryl phosphonates- and phosphates or tertiary amines. Genetically encoded heteroaromatic amino acids include tryptophan and histidine.

Group E comprises amino acids containing side chains with polar-cationic, acylamino- and urea-derived residues according to the general definition for substituen $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged or anionic residues according to the general definition for substituent $R^{84}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxyclic acids and esters, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tetriary amides, carboxylic acids and carboxylates, alkyl- or aryl phosphonates- and phosphates or tertiary amines. Genetically encoded polar-non-charged amino acids include asparagine, cysteine, glutamine, serine and threonine, but also aspartic acid and glutamic acid.

Group LD comprises amino acids containing side chains linked to a dye through a direct bond or a linker L according to the general definition for substituent $R^{86}$. Dyes useful for the present invention are described e.g. by Spikes et al. in Photosensitizing Compounds Their Chemistry, Biology and Clinical Use (Ciba Foundation Symposium 146, J. Wiley &Sons 189, 17-32; Jori et al, *J. Photochem. Photobiol. A: Chem.*, 1992, 62, 371-378; Patonay et al, *Anal. Chem.* 1991, 63:6, 321A-327A; Joni et al, *Light in Biology and Medicine*, Volume 2 Plenum Press, New York, 1991, 253-266; J. R. Lakowicz, Principles of Fluorescence Microscopy, Plenum, N.Y., 1998, X. F. Wang, B. Herman, Fluorescence Imaging Spectroscopy and Microscopy, W. T. Mason, Fluorescent Probes for Biological Activity, Academic Press, New York, 1993; O. S. Wolfbeis, Fluorescence Spectroscopy: New Methods and Applications, Springer, Heidelberg, 1993.

Dyes containing optionally a linker L useful for the present invention include but are not limited to:

Alexa Fluor® 647, Cascade Blue® ethylenediamine, Lissamine™, Rhodamine B ethylenediamine, Oregon Green® 488 cadaverine-5-isomer, Texas Red® cadaverine, 1-pyrenebutanoic acid, 1-pyreneacetic acid, N-(1-pyrenebutanoyl)cysteic acid, 7-methoxycoumarin-3-carboxylic acid, 4,4'-diisothiocyanatostilbene-2,2'-disulfonic acid, 7-hydroxycoumarin-3-carboxylic acid, 6-((7-amino-4-methylcoumarin-3-acetyl)amino)hexanoic acid, 7-diethylaminocoumarin-3-carboxylic acid, 5-(4,6-dichlorotriazinyl) aminofluorescein, 6-carboxyfluorescein, 5-carboxyfluorescein, 6-(fluorescein-5-carboxamido)hexanoic acid, 5-dimethylaminonaphthalene-1-sulfonyl [Dansyl], 6((5-dimethylaminonaphthalene-1-sulfonyl)amino) hexanoic acid, 2',7'-dichloro-6-carboxy-4,7- dichlorofluorescein, 5-(and-6)-carboxyeosin, Fluorescein-5 (6)-carboxamidocaproic acid, 6-carboxyrhodamine, Cascade Yellow, 6-(tetramethylrhodamine-5-(and-6)-carboxamido) hexanoic acid, Texas Red, 4-dimethylaminoazobenzene-4'-sulfonyl, 2-dimethylaminonaphthalene-5-sulfonyl, 2-dimethylaminonaphthalene-6-sulfonyl, 4-((4-(dimethylamino) phenyl)azo)benzoic acid, Oregon Green 488-5-isomer, Oregon Green 488 cadaverine -5-isomer, Oregon Green 514, Rhodamine Green, Texas Red cadaverine, 5(6)-Carboxy-X-rhodamine, 6-Carboxy-X-rhodamine, 5-Carboxy-X-rhodamine, 5(6)-Carboxy-tetramethylrhodamine, 5-Carboxy-tetramethylrhodamine, 6-Carboxy-tetramethylrhodamine, Fluorescent Red 646, Fluorescence orange 548, Fluorescent-Red NIR 782, Fluorescent-Red NIR 730, Fluorescent-Red NIR 700, Fluorescent-Red NIR 680, Fluorescent-Red 610, Atto 520, Atto 532, Atto 550, Atto 565, Atto 590, Atto 610, Atto 620, Atto 635, Atto 647, Atto 655, Alto 680, 2-Methoxy-2,4-diphenyl-3(2H)-furanone, chlorophyll, bacteriochlorophyll, Cy3, Cy5, Cy5.5, Cy7, protoporphyrin, hematoporphyrin, tetra(m-hydroxyphenyl)chlorine, chlorine e6, mesochlorin e6 and luthetium texaphyrin zinc phthalocyanine.

Group H comprises side chains of preferably (L)-amino acids at opposite positions of the β-strand region that can form an interstrand linkage. The most widely known linkage is the disulfide bridge formed by cysteines and homo-cysteines positioned at opposite positions of the β-strand. Various methods are known to form disulfide linkages including those described by: J. P. Tam et al. *Synthesis* 1979, 955-957; Stewart et al., *Solid Phase Peptide Synthesis*, 2d Ed., Pierce Chemical Company, III., 1984; Ahmed et al. *J. Biol. Chem.* 1975, 250, 8477-8482; and Pennington et al., *Peptides*, pages 164-166, Giralt and Andreu, Eds., ESCOM Leiden, The Netherlands, 1990. Most advantageously, for the scope of the present invention, disulfide linkages can be prepared using acetamidomethyl (Acm)-protective groups for cysteine. A well established interstrand linkage consists in linking ornithines and lysines, respectively, with glutamic and aspartic acid residues located at opposite O-strand positions by means of an amide bond formation. Preferred protective groups for the side chain amino-groups of ornithine and lysine are allyloxycarbonyl (Alloc) and allylesters for aspartic and glutamic acid. Finally, interstrand linkages can also be established by linking the amino groups of lysine and ornithine located at opposite β-strand positions with reagents such as N,N-carbonylimidazole to form cyclic ureas.

As mentioned earlier, positions for interstrand linkages are in positions P2 and P13 and/or P4 and P11 taken together. Such interstrand linkages are known to stabilize the β-hairpin conformations and thus constitute an important structural element for the design of β-hairpin mimetics.

Most preferred amino acid residues in chain Z are those derived from natural α-amino acids. Hereinafter follows a list of amino acids which, or the residues of which, are suitable for the purposes of the present invention, the abbreviations corresponding to generally adopted usual practice:

| three letter code | | one letter code |
|---|---|---|
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |
| Pro | L-Proline | P |
| $^D$Pro | D-Proline | $^D$P |
| Ser | L-Serine | S |
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:

| | |
|---|---|
| Cit | L-Citrulline |
| Orn | L-Ornithine |
| tBuA | L-t-Butylalanine |
| Sar | Sarcosine |
| Pen | L-Penicillamine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | 1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | N-Acetyllysine |
| Dpr | 2,3-Diaminopropionic acid |
| A$_2$Bu | 2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-(4-phenyl)phenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| 4-AmPyrr1 | (2S,4S)-4-Amino-pyrrolidine-L-carboxylic acid |
| 4-AmPyrr2 | (2S,4R)-4-Amino-pyrrolidine-L-carboxylic acid |
| 4-PhePyrr1 | (2S,5R)-4-Phenyl-pyrrolidine-L-carboxylic acid |
| 4-PhePyrr2 | (2S,5S)-4-Phenyl-pyrrolidine-L-carboxylic acid |
| 5-PhePyrr1 | (2S,5R)-5-Phenyl-pyrrolidine-L-carboxylic acid |
| 5-PhePyrr2 | (2S,5S)-5-Phenyl-pyrrolidine-L-carboxylic acid |
| Pro(4-OH)1 | (4S)-L-Hydroxyproline |

-continued

| | |
|---|---|
| Pro(4-OH)2 | (4R)-L-Hydroxyproline |
| Pip | L-Pipecolic acid |
| DPip | D-Pipecolic acid |
| OctG | L-Octylglycine |
| NGly | N-Methylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |
| DimK | L-(N',N'Dimethyl)-lysine |
| Lpzp | L-Piperazinic acid |
| Dpzp | D-Piperazinic acid |
| Isorn | L-(N',N'-diisobutyl)-ornithine |
| PipAla | L-2-(4'-piperidinyl)-alanine |
| PirrAla | L-2-(3'-pyrrolidinyl)-alanine |
| Ampc | 4-Amino-piperidine-4-carboxylic acid |
| NMeR | L-N-Methylarginine |
| NMeK | L-N-Methyllysine |
| NMePhe | L-N-Methylphenylalanine |
| IPegK | L-2-Amino-6-{2-[2-(2-methoxy-ethoxy)ethoxy]acetylamino}-hexanoic acid |
| SPegK | L-2-Amino-6-[2-(2methoxy-ethoxy)-acetylamino]-hexanoic acid |
| Dab | L-2,4-Diamino-butyric acid |
| IPegDab | L-2-Amino-4{2-[2-(2-methoxy-ethoxy)-ethoxy]-acetylamino}-butyric acid |
| SPegDab | L-2-Amino-4[2-(2-methoxy-ethoxy)-acetylamino] butyric acid |
| 4-PyrAla | L-2-(4'Pyridyl)-alanine |
| OrnPyr | L-2-Amino-5[(2'carbonylpyrazine)]aminopentanoic acid |

Particularly preferred residues for group C are:

| | |
|---|---|
| Ala | L-Alanine |
| Ile | L-Isoleucine |
| Leu | L-Leucine |
| Met | L-Methionine |
| Val | L-Valine |
| tBuA | L-t-Butylalanine |
| t-BuG | L-tert.-Butylglycine |
| Cha | L-Cyclohexylalanine |
| C4al | L-3-Cyclobutylalanine |
| C5al | L-3-Cyclopentylalanine |
| Nle | L-Norleucine |
| hCha | L-Homo-cyclohexylalanine |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |

Particularly preferred residues for group D are:

| | |
|---|---|
| His | L-Histidine |
| Phe | L-Phenylalanine |
| Trp | L-Tryptophan |
| Tyr | L-Tyrosine |
| Phg | L-Phenylglycine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl2-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Thi | L-β-2-Thienylalanine |
| Tza | L-2-Thiazolylalanine |

-continued

| | |
|---|---|
| Y(Bzl) | L-O-Benzyltyrosine |
| Bip | L-Biphenylalanine |
| S(Bzl) | L-O-Benzylserine |
| T(Bzl) | L-O-Benzylthreonine |
| hPhe | L-Homo-phenylalanine |
| Bpa | L-4-Benzoylphenylalanine |
| PirrAla | L-2-(3'-pyrrolidinyl)-alanine |
| NMePhe | L-N-Methylphenylalanine |
| 4-PyrAla | L-2-(4'Pyridyl)-alanine |

Particularly preferred residues for group E are

| | |
|---|---|
| Arg | L-Arginine |
| Lys | L-Lysine |
| Orn | L-Ornithine |
| Dpr | L-2,3-Diaminopropionic acid |
| A2Bu | L-2,4-Diaminobutyric acid |
| Dbu | (S)-2,3-Diaminobutyric acid |
| Phe(pNH2) | L-para-Aminophenylalanine |
| Phe(mNH2) | L-meta-Aminophenylalanine |
| Phe(oNH2) | L-ortho-Aminophenylalanine |
| hArg | L-Homo-arginine |
| Phe(mC(NH2)=NH) | L-meta-Amidinophenylalanine |
| Phe(pC(NH2)=NH) | L-para-Amidinophenylalanine |
| Phe(mNHC(NH2)=NH) | L-meta-Guanidinophenylalanine |
| Phe(pNHC(NH2)=NH) | L-para-Guanidinophenylalanine |
| DimK | L-(N',N'Dimethyl)-lysine |
| Isorn | L-(N',N'-diisobutyl)-ornithine |
| NMeR | L-N-Methylarginine |
| NMeK | L-N-Methyllysine |
| IPegK | L-2-Amino-6-{2-[2-(2-methoxy-ethoxy)ethoxy]acetylamino}-hexanoic acid |
| SPegK | L-2-Amino-6-[2-(2methoxy-ethoxy)-acetylamino]-hexanoic acid |
| Dab | L-2,4-Diamino-butyric acid |
| IPegDab | L-2-Amino-4{2-[2-(2-methoxy-ethoxy)-ethoxy]-acetylamino}-butyric acid |
| SPegDab | L-2-Amino-4[2-(2-methoxy-ethoxy)-acetylamino] butyric acid |
| OrnPyr | L-2-Amino-5-[(2'carbonylpyrazine)]aminopentanoic |
| PipAla | L-2-(4'-piperidinyl)-alanine |

Particularly preferred residues for group F are

| | |
|---|---|
| Asn | L-Asparagine |
| Asp | L-Aspartic acid |
| Cys | L-Cysteine |
| Gln | L-Glutamine |
| Glu | L-Glutamic acid |
| Ser | L-Serine |
| Thr | L-Threonine |
| Cit | L-Citrulline |
| Pen | L-Penicillamine |
| AcLys | L-N$^\epsilon$-Acetyllysine |
| hCys | L-Homo-cysteine |
| hSer | L-Homo-serine |

Particularly preferred residues for group LD are

| | |
|---|---|
| Lys(Dsl) | L-N$^\epsilon$-(Dansyl)-lysine |
| Dpr(Dsl) | L-N$^\alpha$-(Dansyl)-1,4-diaminobutyric acid |
| Lys(FHS) | L-N$^\epsilon$-[6-(5(6)-Fluorescin carboxamido)-hexanamido]-lysine |
| Lys(FITC) | L-N$^\epsilon$-[5(6)Fluorescinthioureido]-lysine |
| Lys(Alx) | L-N$^\epsilon$-(Alexa Fluor 647)-lysine |

Generally, the peptidic chain Z within the β-hairpin mimetics of the invention comprises 14 amino acid residues. The positions P1 to P14 of each amino acid residue in the chain Z are unequivocally defined as follows: P1 represents the first amino acid in the chain Z that is coupled with its N-terminus to the C-terminus of the templates (b)-(p), or of group —B—CO— in template (a1), or of group -A-CO— in template (a2); and P14 represents the last amino acid in the chain Z that is coupled with its C-terminus to the N-terminus of the templates (b)-(p), or of group -A-CO— in template (a1), or of group —B—CO— in template (a2). Each of the positions P1 to P14 will preferably contain an amino acid residue belonging to one of the above types C D, E, F, LD, H, or of formula -A-CO— or of formula —B—CO—, or being Gly, Pro as follows:

P1: of type C, or of type D, or of type E, or of type F, or of type LD, or the residue is Gly or Pro;
P2: of type E, or of type D, or of type F, or of type LD;
P3: of type E, or of type F, or of type D, or of type C, or of type LD, or the residue is Pro;
P4: of type D, or of type C, or of type F;
P5: of type E, or of type F,;
P6: of type C, or of type D, or of type F, or the residue is Gly or Pro;
P7: of type C, or of type D, or of formula -A-CO—, or the residue is Gly or Pro;
P8: of type E, or of Type F, or of type D, or of type LD, or the residue is Pro;
P9: of type F, or of type E, or of type D, or the residue is Pro;
P10: of type F, or of type D, or of type C;
P11: of type D, or of type C, or of type F, or of type E;
P12: of type C, or of type D, or of type F;
P13: of type F, or of type E, or of type D, or of type LD, or the residue is Gly; and
P14: of type F, or of type E, or of type C, or of type LD; or
P2 and P13 and/or P4 and P11, taken together, form a group of type H; at P4, P7, P8 or P11 D-isomers being possible; with the proviso that the molecule contains at least one "Dye" moiety.

The α-amino acid residues in positions 1 to 14 are most preferably:
P1: Tyr, His, Leu, Ser, or Lys (FHS);
P2: Arg, His, Lys, or —FHS;
P3: Cit; Thr, Tyr, Gln, or Lys (FHS);
P4: Cys;
P5: Arg, or Ser;
P6: Gly, or Ala;
P7: $^D$Pro, or Pro;
P8: Arg, Phe, or Dpr (Dsl);
P9: Arg;
P10: 2-Nal, Trp, Tyr, or Phe;
P11: Cys;
P12: Tyr;
P13: Cit, Gln, or Lys (FHS); and
P14: Lys, Lys (Dsl), Gln, Lys (FHS), Lys (FITC), or Lys (Alx);
with the proviso that Cys at P4 and P11 can form a disulfide bridge; and with the further proviso that that the molecule contains at least one "Dye" moiety.

Particularly preferred dye-conjugates of β-peptidomimetics of the invention include those described in Examples 4, 5, 7, 10 and 16.

The processes of the invention can advantageously be carried out as parallel array syntheses to yield libraries of dye conjugates of template-fixed β-hairpin peptidomimetics of the above general formula I. Such parallel syntheses allow one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (Rink H, *Tetrahedron Lett.* 1987, 28, 3783-3790). Linkers of this kind form amides of the carboxyl group of the amino acids; examples of resins functionalized by such linker structures include 4-[(((2,4-dimethoxyphenyl)Fmoc-aminomethyl)phenoxyacetamido)aminomethyl] PS resin, 4-[((((2,4-dimethoxyphenyl)Fmoc-aminomethyl)phenoxyacetamido)aminomethyl]-4-methylbenzydrylamine PS resin (Rink amide MBHA PS Resin), and 4-[(((2,4-dimethoxyphenyl)Fmoc-aminomethypphenoxyacetamido) aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl.

Preferably, the support is derived from polystyrene crosslinked with, most preferably 1-5%, divinylbenzene and functionalized by means of the 2-chlorotrityl linker.

When carried out as a parallel array syntheses the processes of the invention can be advantageously carried out as described herein below but it will be immediately apparent to those skilled in the art how these procedures will have to be modified in case it is desired to synthesize one single compound of the above formula I.

A number of reaction vessels (normally 24 to 192, typically 96) equal to the total number of compounds to be synthesized by the parallel method are loaded with 25 to 1000 mg, preferably 100 mg, of the appropriate functionalized solid support.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Florsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e.g. also in the side-chain of lysine)

| Cbz | benzyloxycarbonyl |
|---|---|
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Trt | triphenymethyl or trityl | for the carboxyl group (as is present e.g. also in the side-chain of aspartic and glutamic acid) by conversion into esters with the alcohol components

| tBu | tert.-butyl |
|---|---|
| Bn | benzyl |
| Me | methyl |
| Ph | phenyl |
| Pac | Phenacyl Allyl |
| Tse | trimethylsilylethyl |
| Tce | trichloroethyl; | for the guanidino group (as is present e.g. in the side-chain of arginine)

| Pmc | 2,2,5,7,8-pentamethylchroman-6-sulfonyl |
|---|---|
| Ts | tosyl (i.e. p-toluenesulfonyl) |
| Cbz | benzyloxycarbonyl |
| Pbf | pentamethyldihydrobenzofuran-5-sulfonyl | for the hydroxy group (as is present e.g. in the side-chain of threonine and serine)

| tBu | tert.-butyl |
|---|---|
| Bn | benzyl |
| Trt | trityl | and for the mercapto group (as is present e.g. in the side-chain of cysteine)

| Acm | acetamidomethyl |
|---|---|
| tBu | tert.-butyl |
| Bn | benzyl |
| Trt | trityl |
| Mtr | 4-methoxytrityl. |

The 9-fluorenylmethoxycarbonyl-(Fmoc)-protected amino acid derivatives are preferably used as the building blocks for the construction of the dye conjugates of template-fixed β-hairpin loop mimetics of formula I. For the deprotection, i.e. cleaving off of the Fmoc group, 20% piperidine in DMF or 2% DBU/2% piperidine in DMF can be used.

Dyes to be linked to amino acid derivatives directly or through a linker L to form an amino acid residue according to type LD, and -L-Dye moieties which may have to be linked to a template as contained in formula I are well known in the art. The procedure for introducing an L-Dye moiety can be accomplished in the following way: The Dye and the linker L can be coupled for example through an activation by conversion into an isocyanate or isothiocyanate, or by introducing halogen as a leaving group, or by activating reagents such as those described below depending on the type of linker. Procedures including, but not limited to, are as described in Hnatowich et al, *Science* 1983, 220, 613-615; Pelegrin et al, *Journal of Cellular Pharmacology*, 1992, 3, 141-145; Liche et al. in "Biomedical Imaging: Reporters, Dyes, and instrumentation"; D. J. Bornhop, *Proceedings of SPIE*, 1999, 3600, 29-25.

When building up the peptide chain, the quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combichem station and MultiSyn Tech's-Syro synthesizer.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, soluble in the solvents generally used. In a variation of the carbodiimide method 1-hydroxybenzotriazole (HOBt, Konig & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, Castro et al., *Tetrahedron Lett.* 1975, 14, 1219-1222; *Synthesis,* 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-)1,1,3,3-tetramethyluronium terafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s) by one of the two following methods:
1) The reaction wells are filled with solvent (preferably 5 ml), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent;
2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent, and by-product removal by methods such as TLC, GC, or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced. If required, a Dye through a linker L forming an amino acid residue of type LD can be attached and/or an -L-Dye moiety can be linked to a template as contained in formula I.

Before this fully protected linear peptide is detached from the solid support, it is also possible, if desired, to form (an) interstrand linkage(s) between side-chains of appropriate amino acid residues at opposite positions of the β-strand region.

Interstrand linkages and their formation have been discussed above, in connection with the explanations made regarding groups of the type H which can, for example, be disulfide bridges formed by cysteine and homocysteine residues at opposite positions of the β-strand; or lactam bridges formed by glutamic and aspartic acid residues linking ornithine and, respectively, lysine residues, or by glutamic acid residues linking 2,4-diaminobutyric acid residues located at opposite β-strand positions by amide bond formation. The formation of such interstrand linkages can be effected by methods well known in the art.

For the formation of disulfide bridges, preferably a solution of 10 equivalents of iodine solution is applied in DMF or in a mixture of $CH_2Cl_2$/MeOH for 1.5 h which is repeated for another 3 h with a fresh iodine solution after filtering of the iodine solution, or in a mixture of DMSO and acetic acid solution, buffered with 5% with $NaHCO_3$ to pH 5-6 for 4 h, or in water after adjusting to pH 8 with ammonium hydroxide solution by stirring for 24 h, or in a solution of NMP and tri-n-butylphosphine (preferably 50 eq.).

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control, agitation, and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible.

The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THY and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Alternatively the detachment and complete deprotection of the fully protected peptide from the solid support can be achieved manually in glass vessels.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected cyclic peptide derivative of formula I is obtained. If desired, a Dye, directly or through a linker L, forming an amino acid residue of type LD can be attached and/or an -L-Dye moiety can be linked to a template contained in formula I, so as to obtain the end-product.

Depending on its purity, this peptide derivative can be used directly for biological assays, or it has to be further purified, for example by preparative HPLC.

As mentioned earlier, it is thereafter possible, if desired, to convert a fully deprotected product of formula I thus obtained into a pharmaceutically acceptable salt or to convert a pharmaceutically acceptable, or unacceptable, salt thus obtained into the corresponding free compound of formula I or into a different, pharmaceutically acceptable, salt. Any of these operations can be carried out by methods well known in the art.

The template starting materials of formula II used in the processes of the invention, pre-starting materials therefor, and the preparation of these starting and pre-starting materials are described in International Application PCT/EP02/01711 of the same applicants, published as WO 02/070547 A1.

The dye-conjugates of β-hairpin peptidomimetics of the invention can be used in a wide range of therapeutic applications where cancer is mediated or resulting from the CXCR4 receptor activity, or they can be used for diagnostic imaging. In particular, they can be used for detection of tumors and other abnormalities; for photoacoustic tumor imaging, detection and therapy; for sonofluorescence tumor imaging, detection and therapy; or in laser assisted surgery of micro tumors; or in a diagnostic kit wherein the dye-conjugates of the invention can be used for labeling tumor tissues or cells expressing the CXCR4-receptor.

The dye-conjugates of β-hairpin peptidomimetics may be administered per se or may be applied as an appropriate formulation together with carriers, diluents or excipients well known in the art.

When used to treat or prevent cancer such as breast cancer, brain cancer, prostate cancer, lung cancer, kidney cancer, neuroblastoma, non-hodgkin's lymphoma, ovarian cancer, multiple myeloma, chronic lyphomphocytic leukemia, pancreatic cancer, melanoma, angiogenesis, haematopoetic tissues, or colorectal cancer, the dye-conjugates can be administered singly, as mixtures of several dye-conjugates, in combination with other therapeutic agents, such as antimicrobial agents or anti cancer agents or anti-inflammatory agents. The dye-conjugates can be administered per se or as pharmaceutical compositions.

The diagnostic compositions may be administered to a patient as described below to the organ or tissue to be imaged, and the patient then is subjected to the imaging procedure.

For imaging or therapy or diagnostic use, the dye-conjugates of the invention are allowed to accumulate in the region of interest, followed by illumination with the light of a wavelength 300 to 1200 nm at the site of the lesion. If the lesion is on the skin surface, the dye-conjugates can be directly illuminated, otherwise endoscopic catheters equipped with a light source may be employed to achieve e.g. phototherapeutic effects. The intensity, power duration of illumination and the wavelength of the light may vary widely depending on the location and site of the lesions.

The choice of any specific dye-conjugates of the present invention may vary widely depending on the contemplated application.

Pharmaceutical and/or diagnostic compositions comprising dye-conjugates of the invention may be manufactured by means of conventional mixing, dissolving, granulating, coated tablet-making, levigating, emulsifying, encapsulating, entrapping or lyophilizing processes. Such compositions may be formulated in conventional manner using one or more physiologically acceptable carriers, diluents, excipients or auxiliaries which facilitate processing of the active dye-conjugates into preparations which can be used pharmaceutically or for diagnostic purposes. Proper formulation depends upon the method of administration chosen.

For injections, the dye-conjugates of the invention may be formulated in adequate solutions, preferably in physiologically compatible buffers such as Hink's solution, Ringer's solution, or physiological saline buffer. The solutions may contain formulatory agents such as suspending, stabilizing and/or dispersing agents. Alternatively, the dye-conjugates of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active dye-conjugates of the invention with pharmaceutically acceptable carriers well known in the art. Such carriers enable the dye-conjugates of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as crosslinked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the dye-conjugates of the invention are conveniently delivered in form of an aeorosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the dye-conjugates of the invention and a suitable powder base such as lactose or starch.

The compounds may also be formulated in rectal or vaginal compositions such as suppositories together with appropriate suppository bases such as cocoa butter or other glycerides.

In addition to the formulations described previously, the dye-conjugates of the invention may also be formulated as depot preparations. Such long acting formulations may be administered by implantation (e.g. subcutaneously or intramuscularly) or by intramuscular injection. For the manufacture of such depot preparations the dye-conjugates of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the dye-conjugates of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the dye-conjugates of the invention may contain charged residues, they may be included in any of the above-described formulations as such or as pharmaceutically acceptable salts. Pharmaceutically acceptable salts tend to be more soluble in aqueous and other protic solvents than are the corresponding free forms.

The dye-conjugates of the invention, or compositions thereof, will generally be used in an amount effective to achieve the intended purpose. It is to be understood that the amount used will depend on a particular application.

For systemic administration, a therapeutically effective dose can be estimated initially from in vitro assays. For example, a dose can be formulated in animal models to achieve a circulating dye-conjugate concentration range that includes the $IC_{50}$ as determined in the cell culture (i.e. the concentration of a test compound that is lethal to 50% of a cell culture). Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as therapeutic agents may be adjusted individually to provide plasma levels of the dye-conjugates of the invention which are sufficient to maintain the therapeutic effect. Therapeutically effective serum levels may be achieved by administering multiple doses each day.

In cases of local administration or selective uptake, the effective local concentration of the dye-conjugates of the invention may not be related to plasma concentration. One having the ordinary skill in the art will be able to optimize therapeutically effective local dosages without undue experimentation.

The amount of dye-conjugates administered will, of course, be dependent on the subject being treated, on the subject's weight, the severity of the affliction, the manner of administration and the judgement of the prescribing physician.

Normally, a therapeutically effective dose of the dye-conjugates described herein will provide therapeutic benefit without causing substantial toxicity.

Toxicity of the dye-conjugates of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the dye-conjugates of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The following Examples illustrate the invention in more detail but are not intended to limit its scope in any way. The following abbreviations are used in these Examples:

HBTU: 1-benzotriazol-1-yl-tetramethylurounium hexafluorophosphate (Knorr et al. *Tetrahedron Lett.* 1989, 30, 1927-1930);

HOBt: 1-hydroxybenzotriazole;

DIEA: diisopropylethylamine;

HOAT: 7-aza-1-hydroxybenzotriazole;

HATU: O-(7-aza-benzotriazole-1-yl)-N,N,N',N'-tetramethyluronium hexafluorophosphate (Carpino et al. *Tetrahedron Lett.* 1994, 35, 2279-2281).

EXAMPLES

1. Peptide Synthesis

Coupling of the First Protected Amino Acid Residue to the Resin 0.5 g of 2-chlorotritylchloride resin (Barlos et al. *Tetrahedron Lett.* 1989, 30, 3943-3946) (0.83 mMol/g, 0.415 mmol) was filled into a dried flask. The resin was suspended in $CH_2Cl_2$ (2.5 ml) and allowed to swell at room temperature under constant stirring for 30 min. The resin was treated with 0.415 mMol (1 eq) of the first suitably protected amino acid residue (see below) and 284 µl (4 eq) of diisopropylethylamine (DIEA) in $CH_2Cl_2$ (2.5 ml), and the mixture was shaken at 25° C. for 4 hours. The resin colour changed to purple and the solution remained yellowish. The resin was shaken ($CH_2Cl_2$/MeOH/DIEA: 17/2/1), 30 ml for 30 min; then washed in the following order with $CH_2Cl_2$ (1×), DMF (1×), $CH_2Cl_2$ (1×), MeOH (1×), $CH_2Cl_2$(1×), MeOH (1×), $CH_2Cl_2$ (2×), $Et_2O$ (2×) and dried under vacuum for 6 hours.

Loading was typically 0.6-0.7 mMol/g.

The following preloaded resins were prepared: Fmoc-ProO-chlorotritylresin and Fmoc-(2S,-4R)-Boc-4-Amino-1-Fmoc-pyrrolidine-2 carboxy-chlorotritylresin.

Synthesis of the Fully Protected Peptide Fragment

The synthesis was carried out using a Syro-peptide synthesizer (Multisyntech) using 24 to 96 reaction vessels. In each vessel were placed 60 mg (weight of the resin before loading) of the above resin. The following reaction cycles were programmed and carried out:

| Step | Reagent | Time |
|---|---|---|
| 1 | $CH_2Cl_2$, wash and swell (manual) | 3 × 1 min. |
| 2 | DMF, wash and swell | 1 × 5 min |
| 3 | 40% piperidine/DMF | 1 × 5 min. |
| 4 | DMF, wash | 5 × 2 min. |
| 5 | 5 equiv. Fmoc amino acid/DMF + 5 eq. HBTU + 5 eq. HOBt + 5 eq. DIEA | 1 × 60 min. |
| 6 | DMF, wash | 4 × 2 min. |
| 7 | $CH_2Cl_2$, wash (at the end of the synthesis) | 3 × 2 min. |

Step 5 was repeated twice
Steps 3 to 6 are repeated to add each amino-acid.

Attachment of the Dye Label
Procedure A
Attachment of Dansyl Dye to the Selectively Deprotected Cyclized Peptide on the Resin:

The resin (0.040 mmol) containing the peptide was swollen in 5 ml of freshly distilled $CH_2Cl_2$ for 30 min and then the palladium catalyst $Pd(PPh_3)_4$, 14 mg, 0.3 eq, was added followed by $PhSiH_3$, 0.8 mmol, 20 eq. The resin was shaken for 2 h and the reaction solution was filtered off. The reaction was repeated again by employing the same amount of reagents, and after 2 h the resin was washed with $CH_2Cl_2$ and DMF and finally with $Et_2O$.

The resin was swollen again in freshly distilled $CH_2Cl_2$ (2 ml) for 30 min, the solvent was filtered off and the resin swollen in DMF for 1 h.

The resin (0.040 mmol) was swollen in freshly distilled DCM (2 ml) for 30 min and then the solvent was filtered off and the resin swollen in DMF (3 ml) for 1 h. Dansyl chloride 98% (Aldrich), 5 eq and DIPEA (dist.), 10 eq were dissolved in DMF (1.5 ml) and the resultant solution was added to the resin swollen in DMF (1.5 ml). The resin was shaken for 3 hours after which the coupling was completed as revealed by a Kaiser test and confirmed by LC MS analysis. Thereafter, the solution was filtered off and the resin was washed with DCM, DMF and finally with $Et_2O$.

Procedure B
Attachment of FITC Dye as Postmodification to the Final Deprotected Cyclized Peptide:

The peptide (1 µmol) was dissolved the in sodium tetraborate solution (0.2 ml), (pH=9) in a small vial wrapped in tin foil and then cooled down to ca. 4° C. in an ice bath. To the stirred solution the FITC dye (Fluorescein isothiocynate isomer IxHCl >99% 1.5 µmol) dissolved in DMF (0.03 ml) was added and the mixture was stirred for 5 hours at the same temperature. LC MS analysis revealed that the reaction was completed, and acetic acid 0.2 M (0.3 ml) was added. The solution was diluted with 0.5 ml of water/acetonitrile (90/10), filtered and was purified directly by HPLC.

After lyophilisation the products were obtained as white powders and analysed by ESI-MS. The analytical data comprising purity after preparative HPLC and ESI-MS are shown in Table 1.

Procedure C
Attachment of FHS Dye as Postmodification to the Final Deprotected Cyclised Peptide:

The peptide (1 µmol) was dissolved the in sodium tetraborate solution (0.2 ml) (pH=8) in a small vial wrapped in tin foil. To the stirred solution the FHS dye (Fluorescein-5(6)-carboxamidocaproic acid N-succinimidyl ester >75% purity, 2 µmol) dissolved in DMF (0.03 ml) was added and the mixture was stirred for 5 hours at room temperature. LC MS analysis revealed that the reaction was not completed after 5 hours (ca. 30% of unreacted peptide was found), but prolonged reaction time (>1 day) led to the formation of a more impure mixture and for this reason the reaction was quenched after 5 hours even if not complete. Acetic acid (0.2 M) (0.3 ml) was added and the solution was diluted with 0.5 ml of water/acetonitrile (90/10), filtered and was purified directly by HPLC.

After lyophilisation the products were obtained as white powders and analysed by ESI-MS. The analytical data comprising purity after preparative HPLC and ESI-MS are shown in Table 1.

Procedure D
Attachment of Alexa Fluor® 647 Dye as Postmodification to the Final Deprotected Cyclised Peptide:

The peptide (1.5 µmol) was dissolved in sodium tetraborate solution (0.36 ml) (pH=9) in a small vial wrapped in tin foil and then to the stirred solution the Alexa Fluor® 647 succinimid ester (0.75 mmol) dissolved in DMF (0.095 ml) was added and the mixture was stirred for 2 hours at room temperature. LC MS analysis revealed that the reaction was completed, and acetic acid (0.2 M) (0.5 ml) was added. The solution was diluted with 0.5 ml of water/acetonitrile (90/10), filtered and was purified directly by HPLC. After lyophilisation the products were obtained as white powders and analysed by ESI-MS. The analytical data comprising purity after preparative HPLC and ESI-MS are shown in Table 1.

Cyclization and Work Up of Backbone Cyclized Peptides
Cleavage of the Fully Protected Peptide Fragment After completion of the synthesis, the resin was suspended in 1 ml (0.39 mMol) of 1% TFA in $CH_2Cl_2$ (v/v) for 3 minutes, filtered and the filtrate was neutralized with 1 ml (1.17 mMol, 3 eq.) of 20% DIEA in $CH_2Cl_2$ (v/v). This procedure was repeated twice to ensure completion of the cleavage. The filtrate was evaporated to dryness and a sample of the product was fully deprotected [cleavage mixture containing 95% trifluoroacetic acid (TFA), 2.5% water and 2.5% triisopropylsilane (TIS)] to be analyzed by reverse phase-HPLC (column $C_{18}$) and ESI-MS to monitor the efficiency of the linear peptide synthesis.

Cyclization of the Linear Peptide 100 mg of the fully protected linear peptide were dissolved in DMF (9 ml, conc. 10 mg/ml). Then 41.8 mg (0.110 mMol, 3 eq.) of HATU, 14.9 mg (0.110 mMol, 3 eq) of HOAt and 1 ml (0.584 mMol) of 10% DIEA in DMF (v/v) were added, and the mixture was vortexed at 20° C. for 16 hours and subsequently concentrated under high vacuum.

The residue was partitioned between $CH_2Cl_2$ and $H_2O/CH_3CN$ (90/10: v/v). The $CH_2Cl_2$ phase was evaporated to yield the fully protected cyclic peptide.

Deprotection and Purification of the Cyclic Peptide

The cyclic peptide obtained was dissolved in 1 ml of the cleavage mixture containing 95% trifluoroacetic acid (TFA), 2.5% water and 2.5% triisopropylsilane (TIS). The mixture was left to stand at 20° C. for 2.5 hours and then concentrated under vacuum. The residue was dissolved in a solution of $H_2O$/acetic acid (75/25: v/v) and the mixture was extracted with di-isopropylether.

Formation of Disulfide β-Strand Linkage

After deprotection, the crude peptide was dissolved in 9.5 ml of 5% AcOH (buffered with $NaHCO_3$ to pH 5-6) and 0.5 ml of DMSO were added. The solution was shaken for 3.5 hours and then the solvent was evaporated and the residue was purified by preparative reverse phase HPLC.

After lyophilisation the products were obtained as white powders and analysed by ESI-MS. The analytical data comprising purity after preparative HPLC and ESI-MS are shown in Table 1.

Analytical Method 1:

Analytical HPLC retention times (RT, in minutes) were determined using a Jupiter Proteo 90A, 50×2.0 mm Phenomenex column with the following solvents A (H$_2$O+0.1% TFA) and B (CH$_3$CN) and the gradient: 0 min: 95% A, 5% B; 8 min: 30% A 70% B; 9-10 min: 0% A, 100% B; 10.1-12 min: 95% A, 5% B.

Analytical Method 2:

Analytical HPLC retention times (RT, in minutes) were determined using a Jupiter Proteo 90A, 50×2.0 mm Phenomenex column with the following solvents A (H$_2$O+0.1% TFA) and B (CH$_3$CN+0.1% TFA) and the gradient: 0 min: 95% A, 5% B; 20 min: 40% A 60% B; 21-23 min: 0% A, 100% B; 23.1-31 min: 95% A, 5% B.

Examples 1 and 2 are shown in Table 1. The peptides were synthesized starting with the amino acid Pro which was grafted to the resin. Starting resin was Fmoc-ProO-chlorotrityl resin, which was prepared as described above. The linear peptides were synthesized on solid support according to the procedure described above in the following sequence: Resin-Pro-$^D$Pro-P14-P13-P12-P11-P10-P9-P8-P7-P6-P5-P4-P3-P2-P1. Thereafter procedure A was applied for Ex. 1 to attach the dansyl dye to the side chain of Lys at position 14 and for Ex. 2 to the side chain of Dab at position 8. The peptides were cleaved from the resin, cyclized, deprotected and purified as indicated above.

HPLC-retention times (minutes) were determined using the gradient method 1 as described above:

Ex. 1 (4.98); Ex. 2 (4.62);

Examples 3, 5, 6, 8 and 9 are shown in Table 1. The peptides were synthesized starting with the amino acid Pro which was grafted to the resin. Starting resin was Fmoc-ProO-chlorotrityl resin, which was prepared as described above. The linear peptides were synthesized on solid support according to the procedure described above in the following sequence: Resin-Pro-$^D$Pro-P14-P13-P12-P11-P10-P9-P8-P7-P6-P5-P4-P3-P2-P1. Thereafter they were cleaved from the resin, cyclized, deprotected and purified as indicated above. Then procedure C was applied for Ex. 3 to attach the FHS dye to the side chain of Lys at Position 1, for Ex. 5 to the side chain of Lys at Position 3, for Ex. 6 to the side chain of Lys at position 14; for Ex. 8 to the side chain of Lys at Position 13, and for Ex 9 to the side chain of Lys at position 2.

HPLC-retention times (minutes) were determined using the gradient method 1 as described above:

Ex. 3 (3.84); Ex. 5 (3.94); Ex. 6 (4.24); Ex. 8 (4.02); Ex. 9 (4.01).

Example 4 is shown in Table 1. The peptide was synthesized starting with the amino acid AmPro which was grafted to the resin. Starting resin was Fmoc-(2S,-4R)-Boc-4-Amino-1-Fmoc-pyrrolidine-2 carboxy-chlorotritylresin, which was prepared as described above. The linear peptide was synthesized on solid support according to the procedure described above in the following sequence: Resin-(2S,-4R)-Boc-4-Amino-1-Fmoc-pyrrolidine-2 carboxy-$^D$Pro-P14-P13-P12-P11-P10-P9-P8-P7-P6-P5-P4-P3-P2-P1. Thereafter it was cleaved from the resin, cyclized, deprotected and purified as indicated above. Then procedure C was applied to attach the FHS dye to the amino function of (2S,-4R)-4-Amino-1-pyrrolidine-2 carboxylic acid HPLC-retention time (minutes) was determined using the gradient method 1 as described above:

Ex. 4 (3.81)

Example 10 is shown in Table 1. The peptide was synthesized starting with the amino acid Pro which was grafted to the resin. Starting resin was Fmoc-ProO-chlorotrityl resin, which was prepared as described above. The linear peptide was synthesized on solid support according to the procedure described above in the following sequence: Resin-Pro-$^D$Pro-P14-P13-P12-P11-P10-P9-P8-P7-P6-P5-P4-P3-P2-P1. Thereafter it was cleaved from the resin, cyclized, deprotected and purified as indicated above. Then procedure D was applied to attach the Alexa Fluor 647 dye to the side chain of Lys. HPLC-retention time (minutes) was determined using the gradient method 1 as described above:

Ex. 10 (3.63)

Examples 7 and 11-18 are shown in Table 1. The peptides were synthesized starting with the amino acid Pro which was grafted to the resin. Starting resin was Fmoc-ProO-chlorotrityl resin, which was prepared as described above. The linear peptides were synthesized on solid support according to the procedure described above in the following sequence: Resin-Pro-$^D$Pro-P14-P13-P12-P11-P10-P9-P8-P7-P6-P5-P4-P3-P2-P1. Thereafter they were cleaved from the resin, cyclized, deprotected and purified as described above. Then procedure B was applied to attach the FITC dye to the side chain of Lys at position 14.

HPLC-retention time (minutes) was determined using the gradient method 1 as described above: Ex. 7 (4.25)

HPLC-retention times (minutes) were determined using the gradient method 2 as described above:

Ex. 11 (12.58); Ex. 12 (13.17); Ex. 13 (12.28); Ex. 14 (13.11); Ex. 15 (12.50); Ex. 16 (14.43); Ex. 17 (12.55); Ex. 18 (13.70).

TABLE 1

| Example | Sequ. ID | P1 | P2 | P3 | P4 | P5 | P6 | P7 | P8 | P9 | P10 | P11 | P12 | P13 |
|---|---|---|---|---|---|---|---|---|---|---|---|---|---|---|
| 1 | SEQ ID NO: 1 | Tyr | Arg | Cit | Cys | Arg | Gly | $^D$Pro | Arg | Arg | Trp | Cys | Tyr | Cit |
| 2 | SEQ ID NO: 2 | Tyr | Arg | Cit | Cys | Arg | Gly | Pro | Dpr (Dsl) | Arg | Trp | Cys | Tyr | Cit |
| 3 | SEQ ID NO: 3 | Lys (FHS) | Arg | Cit | Cys | Arg | Gly | $^D$Pro | Arg | Arg | Trp | Cys | Tyr | Cit |
| 4 | SEQ ID NO: 4 | Tyr | Arg | Cit | Cys | Arg | Gly | $^D$Pro | Arg | Arg | Trp | Cys | Tyr | Cit |
| 5 | SEQ ID NO: 5 | Tyr | Arg | Lys (FHS) | Cys | Arg | Gly | $^D$Pro | Arg | Arg | Trp | Cys | Tyr | Cit |
| 6 | SEQ ID NO: 6 | Tyr | Arg | Thr | Cys | Arg | Gly | $^D$Pro | Arg | Arg | 2-Nal | Cys | Tyr | Cit |
| 7 | SEQ ID NO: 7 | Tyr | Arg | Thr | Cys | Arg | Gly | $^D$Pro | Arg | Arg | 2-Nal | Cys | Tyr | Cit |

TABLE 1-continued

Examples

| | | P1 | P2 | P3 | P4 | P5 | P6 | P7 | P8 | P9 | P10 | P11 | P12 | P13 |
|---|---|---|---|---|---|---|---|---|---|---|---|---|---|---|
| 8 | SEQ ID NO: 8 | Tyr | Arg | Cit | Cys | Arg | Gly | $^D$Pro | Arg | Arg | Trp | Cys | Tyr | Lys(FHS) |
| 9 | SEQ ID NO: 9 | Tyr | Lys(FHS) | Cit | Cys | Arg | Gly | $^D$Pro | Arg | Arg | Trp | Cys | Tyr | Cit |
| 10 | SEQ ID NO: 10 | Tyr | Arg | Thr | Cys | Arg | Gly | Pro | Arg | Arg | 2-Nal | Cys | Tyr | Cit |
| 11 | SEQ ID NO: 11 | His | His | Gln | Cys | Ser | Ala | $^D$Pro | Phe | Arg | Tyr | Cys | Tyr | Gln |
| 12 | SEQ ID NO: 12 | Leu | His | Thr | Cys | Arg | Ala | $^D$Pro | Arg | Arg | Tyr | Cys | Tyr | Gln |
| 13 | SEQ ID NO: 13 | His | His | Tyr | Cys | Arg | Ala | $^D$Pro | Phe | Arg | Phe | Cys | Tyr | Gln |
| 14 | SEQ ID NO: 14 | Ser | His | Tyr | Cys | Arg | Ala | $^D$Pro | Phe | Arg | Phe | Cys | Tyr | Gln |
| 15 | SEQ ID NO: 15 | Tyr | Arg | Thr | Cys | Arg | Gly | $^D$Pro | Arg | Arg | Tyr | Cys | Tyr | Gln |
| 16 | SEQ ID NO: 16 | Tyr | Arg | Thr | Cys | Arg | Ala | $^D$Pro | Arg | Arg | Tyr | Cys | Tyr | Gln |
| 17 | SEQ ID NO: 17 | Tyr | Arg | Tyr | Cys | Arg | Ala | $^D$Pro | Phe | Arg | Phe | Cys | Tyr | Gln |
| 18 | SEQ ID NO: 18 | Tyr | His | Tyr | Cys | Ser | Ala | $^D$Pro | Phe | Arg | Tyr | Cys | Tyr | Gln |

| Example | Sequ. ID | P14 | Template | Purity%[a] | [M + 2H]/2 |
|---|---|---|---|---|---|
| 1 | SEQ ID NO: 1 | Lys(Dsl) | $^D$Pro$^L$Pro | 95 | 1182.1 |
| 2 | SEQ ID NO: 2 | Lys | $^D$Pro$^L$Pro | 95 | 1154.0 |
| 3 | SEQ ID NO: 3 | Gln | $^D$Pro$^L$Pro | 95 | 1283.6 |
| 4 | SEQ ID NO: 4 | Gln | $^D$ProAmPRO (FHS) | 95 | 1308.6 |
| 5 | SEQ ID NO: 5 | Gln | $^D$Pro$^L$Pro | 99 | 1286.6 |
| 6 | SEQ ID NO: 6 | Lys(FHS) | $^D$Pro$^L$Pro | 95 | 1278.6 |
| 7 | SEQ ID NO: 7 | Lys(FITC) | $^D$Pro$^L$Pro | 95 | 1237.5 |
| 8 | SEQ ID NO: 8 | Gln | $^D$Pro$^L$Pro | 95 | 1287.1 |
| 9 | SEQ ID NO: 9 | Gln | $^D$Pro$^L$Pro | 95 | 1464.0 |
| 10 | SEQ ID NO: 10 | Lys(ALX) | $^D$Pro$^L$Pro | 84 | 1206.0 |
| 11 | SEQ ID NO: 11 | Lys(FITC) | $^D$Pro$^L$Pro | 83 | 1195.5 |
| 12 | SEQ ID NO: 12 | Lys(FITC) | $^D$Pro$^L$Pro | 50 | 1203.5 |
| 13 | SEQ ID NO: 13 | Lys(FITC) | $^D$Pro$^L$Pro | 92 | 1222.0 |
| 14 | SEQ ID NO: 14 | Lys(FITC) | $^D$Pro$^L$Pro | 48 | 1165.0 |
| 15 | SEQ ID NO: 15 | Lys(FITC) | $^D$Pro$^L$Pro | 83 | 1206.0 |
| 16 | SEQ ID NO: 16 | Lys(FITC) | $^D$Pro$^L$Pro | 95 | 1195.5 |
| 17 | SEQ ID NO: 17 | Lys(FITC) | $^D$Pro$^L$Pro | 83 | 1203.5 |
| 18 | SEQ ID NO: 18 | Lys(FITC) | $^D$Pro$^L$Pro | 85 | 1222.0 |

Cys in pos. 4 and 11 in Ex. 1-18 form a disulfide bridge,
[a] %-purity of compounds after prep. HPLC

2. Biological Methods

2.1. Preparation of the Peptides

Lyophilized peptides were weighed on a Microbalance (Mettler MT5) and dissolved in sterile water to a final concentration of 1 mM unless stated otherwise. Stock solutions were kept at +4° C., light protected.

2.2. Ca$^{2+-}$ Assay: CXCR4-Antagonizing Activity of the Peptides

Increases in intracellular calcium were monitored using a Flexstation 384 (Molecular Devices, Sunnyvale, Calif.) to assay the peptides for CXCR4 antagonism in a mouse pre-B cell line 300-19 stably transfected with human CXCR4. The cells were batch loaded with the Calcium 3 Assay kit (Molecular Devices) in assay buffer (Hanks Balanced salt solution, HBSS, 20 mM HEPES, pH 7.4, 0.1% BSA) for 1 h at room temperature and then 250,000 labeled cells were dispensed into black 96 well assays plates (Costar No. 3603). A 20-fold concentrated solution of peptide in assay buffer was added to the cells and the whole plate was centrifuged to settle the cells to the bottom of the wells. Calcium mobilization induced by 10 nM stromal-derived factor-1 (SDF-1) was measured in the Flexstation 384 (excitation, 485 nM; emission, 525 nM) for 90 seconds. A maximal change in fluorescence response above baseline was used to calculate antagonist activity. The data for dose response curves (antagonist concentration versus % maximum response) were fitted to a four parameter logistic equation using SoftmaxPro 4.6 (Molecular Devices), from which $IC_{50}$% values were calculated.

2.3. Cytotoxicity Assay

The cytotoxicity of the peptides to HELA cells (Acc57) and COS-7 cells (CRL-1651) was determined using the MTT reduction assay [see ref. 5 and 6, below]. Briefly the method was as follows: HELA cells and COS-7 cells were seeded at $7.0 \cdot 10^3$ and, respectively, $4.5 \cdot 10^3$ cells per well and grown in 96-well microtiter plates for 24 hours at 37° C. at 5% $CO_2$. At this point, time zero (Tz) was determined by MTT reduction (see below). The supernatant of the remaining wells was discarded, and fresh medium and the peptides in serial dilutions of 12.5, 25 and 50 μM were pipetted into the wells. Each peptide concentration was assayed in triplicate. Incubation of the cells was continued for 48 hours at 37° C. at 5% $CO_2$. Wells were then washed once with PBS, and subsequently 100 μl MTT reagent (0.5 mg/mL in medium RPMI1640 and, respectively, DMEM) was added to the wells. This was incubated at 37° C. for 2 hours and subsequently the medium was aspirated and 100 μl isopropanol was added to each well. The absorbance at 595 nm of the solubilized product was measured ($OD_{595}$peptide). For each concentration averages were calculated from triplicates. The percentage of growth was calculated as follows: ($OD_{595}$peptide-$OD_{595}$Tz-$OD_{595}$Empty well)/($OD_{595}$Tz-$OD_{595}$Empty well)×100% and was plotted for each peptide concentration.

The LC 50 values (Lethal Concentration, defined as the concentration that kills 50% of the cells) were determined for each peptide by using the trend line function of EXCEL (Microsoft Office 2000) for the concentrations (50, 25, 12.5 and 0 μM), the corresponding growth percentages and the value −50, (=TREND (C50:$CO_3$%50:%0,−50)). The GI 50 (Growth Inhibition) concentrations were calculated for each peptide by using a trend line function for the concentrations (50, 25, 12.5 and 0 μg/ml), the corresponding percentages and the value 50, (=TREND ($C_{50}$:$C_0$,%$_{50}$:%$_0$,50)).

2.4. Hemolysis

The peptides were tested for their hemolytic activity against human red blood cells (hRBC). Fresh hRBC were washed three times with phosphate buffered saline (PBS) by centrifugation for 10 min at 2000×g. Peptides at a concentration of 100 μM were incubated with 20% v/v hRBC for 1 hour at 37° C. The final erythrocyte concentration was approximately $0.9 \times 10^9$ cells per ml. A value of 0% resp. 100% cell lysis was determined by incubation of the hRBC in the presence of PBS alone and respectively 0.1% Triton X-100 in $H_2O$. The samples were centrifuged and the supernatant was 20-fold diluted in PBS buffer and the optical density (OD) of the sample at 540 nM was measured. The 100% lysis value ($OD_{540}H_2O$) gave an $OD_{540}$ of approximately 1.3-1.8. Percent hemolysis was calculated as follows: ($OD_{540}$peptide/$OD_{540}H_2O$)×100%.

2.5 FACS® Analysis

CXCR4 expressing cells ($5 \times 10^6$/ml) [see references 1, 2 and 3, below] were incubated for 1 hour at 4° C. in a buffer containing HBSS+1% BSA with or without peptidomimetic-dye conjugates at the appropriate concentrations. After this incubation, the cells were washed twice in the same buffer and resuspended at $4 \times 10^6$/ml in PBS and kept on ice until measurements were made. All measurements were made on a BD FACSCalibur™ instrument [see ref 4 below] at a wavelength of 530 nm and a total of 10,000 events were counted for each condition. Unlabeled CXCR4 cells and untransfected 300-19 cells were used to establish an appropriate gate for scoring positive and negative events. Four-parameter curve fitting was made from plots of % gated cells vs. concentration of fluorescent compound using Grafit (Erithacus Software).

2.6 In Vivo Metastasis Studies

CB-17 severe combined immunodeficient (SCID) mice (5 weeks old) are injected intravenously into the tail vein with MDA-MB-231 breast carcinoma cells (1 Mill cells)) and palpable masses are detected after 7-14 days of post implantant.

A non invasive in vivo fluorescence imaging apparatus is used to assess the efficacy of contrast agents of the present invention.

A laser matrix diode of a nominal wave length of 650 nm and a nominal power of 30 mW (RLT6530MG, Roithner Lasertechnik, Vienna, Austria) is used connected with a fiber optic bundle and a defocusing lens in position after the bundle. The detector is a CoolSNAP$_{HQ}$ Monochrome CCD camera (Roper Scientific) with a Rodenstock 10 mm F2 lens and a filter is mounted in of the CCD input lens (XF3030, Omega optical Inc. USA) such that only emitted fluorescent light from the fluorescent peptide is detected. An image is taken of the animal before injection of the agent. This image is subsequently subtracted from the postadministration images. The false color image of fluorescence image intensity is measured at 0.5, 1, 2, 5, 10, 20, 30, 45, 60 minutes after bolus injection of a 0.5 ml aqueous solution of the fluorescent peptide (0.5 mg/kg, 2 mg/kg). All experiments are performed with the mouse in a stationary position (mouse is anesthetisized and the skin area is shaved).

3.0. Results

The results of the experiments described under 2.2-2.4, above, are indicated in Table 2 herein below.

TABLE 2

| Ex. | $IC_{50}$ (nM) $Ca^{2+}$ assay | Cytotoxicity $LC_{50}/GI_{50}$ Hela cells | Hemolysis at 100 μM |
|---|---|---|---|
| 1 | 122.0 | 31 | 0 |
| 2 | 36.8 | n.d. | n.d. |
| 3 | 16.4 | n.d. | n.d. |
| 4 | 13.4 | n.d. | n.d. |
| 5 | 4.9 | n.d. | n.d. |
| 6 | 37.4 | n.d. | n.d. |
| 7 | 0.9 | n.d. | n.d. |
| 8 | 9.7 | n.d. | n.d. |
| 9 | 500 | n.d. | n.d. |
| 11 | 27.5 | n.d. | n.d. |
| 12 | 6.9 | n.d. | n.d. |
| 13 | 29.0 | n.d. | n.d. |
| 14 | 30.4 | n.d. | n.d. |
| 15 | 6.0 | n.d. | n.d. |
| 16 | 4.2 | n.d. | n.d. |
| 17 | 21.8 | n.d. | n.d. |
| 18 | >500 | n.d. | n.d. | n.d.: not determined

FACS Results

FIG. 1 shows histograms of untransfected cells (continuous line) or CXCR4 transfected cells (dotted line) labeled with peptidomimetic-dye conjugates and analyzed by FACS: 10,000 cells were analyzed for fluorescence intensity at 530 nm and plotted on a logarithmic scale on the X-axis vs. number of cells with a particular intensity on the Y-axis. The continuous line trace shows results from untransfected cells incubated with Ex. 4 and represents background fluorescence from any non-specific binding and cellular autofluorescence with 0.7% of cells binding compound. The dotted line plot is the histogram obtained from the CXCR4 expressing cells incubated with the compound. The shift to the right on the intensity scale indicates a ~5-fold increase in fluorescence with >80% of the cells being positive for peptidomimetic-dye conjugates.

Figure 2:
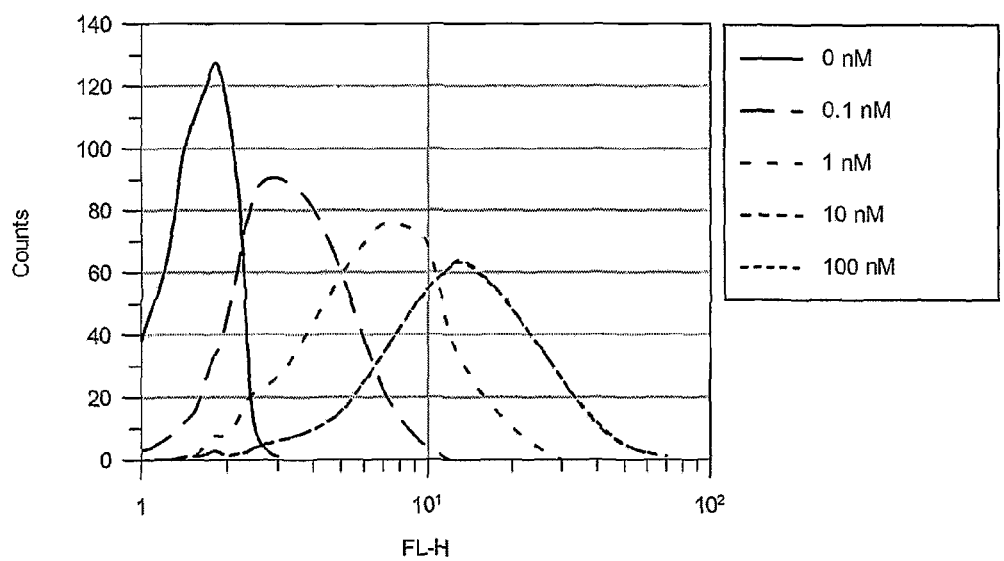
FIG. 2 shows histograms from FACS analysis with Ex. 4 using different concentrations of Ex. 4 (0.1 nM, 1 nM, 10 nM, 100 nM).

FIG. 2 shows the histograms from FACS analysis with Ex. 4 using different concentrations of Ex. 4 (0.1 nM, 1 nM, 10 nM, 100 nM). Ex. 4 was incubated with CXCR4 cells and 10,000 cells from each sample were counted and measured for fluorescence intensity. Left-ward shift of the peak is indicative of increasing fluorescence/compound binding.

The cells were counted by FACS and the % of gated cells was plotted against the concentration of compound using data from the above histogram.

REFERENCES

1. Oberlin E, Amara A, Bachelerie F, Bessia C, Virelizier J-L, Arenzana-Seisdedos F, Schwartz O, Heard J-M, Clark-Lewis I, Legler D F, Loetscher M, Baggiolini M, Moser B. *Nature*. 1996, 382:833-835
2. Loetscher M, Geiser T, O'Reilly T, Zwalen R, Baggiolini M, Moser B. *J. Biol. Chem*. 1994. 269:232-237
3. D'Apuuo M, Rolink A, Loetscher M, Hoxie J A, Clark-Lewis I, Melchors F, Baggiolini M, Moser B. *Eur. J. Immunol*. 1997. 27:1788-1793
4. Coligan John E, Kruisbeek Ada M., Margulies David H, Shevach Ethan M., Strober Warren *Current Protocols in Immunology* published by John Wiley & Sons 1999 Brooklyn, N.Y.
5. Mossman T. *J. Immunol. Meth*. 1983, 65:55-63
6. Berridge M V, Tan A S. *Arch. Biochem. Biophys*. 1993, 303:474-482

---

What is claimed is:

1. A compound of the general formula

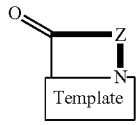

(I)

wherein

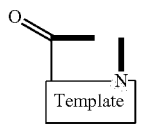

is $^D$Pro-$^L$Pro or $^L$Pro-$^D$Pro and Z is a chain of 14 alpha-amino acid residues, the positions of said amino acid residues in the chain being counted starting from the N-terminal amino acid, whereby a N terminus of P1 is attached a C-terminus of said template, and a C-terminus of P14 is attached to a N terminus of said template, whereby these amino acid residues in positions 1 to 14 are:

P1: Tyr;
P2: Arg;
P3: Cit;
P4: Cys;
P5: Arg;
P6: Gly;
P7: $^D$Pro;
P8: Arg;
P9: Arg;
P10: Trp;
P11: Cys;
P12: Tyr;
P13: Cit; and
P14: Lys(Ds1)

or

P1: Tyr;
P2: Arg;
P3: Cit;
P4: Cys;
P5: Arg;
P6: Gly;
P7: Pro;
P8: Dpr(Dsl);
P9: Arg;
P10: Trp;
P11: Cys;
P12: Tyr;
P13: Cit; and
P14: Lys;

or

P1: Lys(FHS);
P2: Arg;
P3: Cit;
P4: Cys;
P5: Arg;
P6: Gly;
P7: $^D$Pro;
P8: Arg;
P9: Arg;
P10: Trp;
P11: Cys;
P12: Tyr;
P13: Cit; and
P14: Gln;

or

P1: Tyr;
P2: Arg;
P3: Lys(FHS);
P4: Cys;
P5: Arg;
P6: Gly;
P7: $^D$Pro;
P8: Arg;
P9: Arg;
P10: Trp;
P11: Cys;
P12: Tyr;
P13: Cit; and
P14: Gln;

or

P1: Tyr;
P2: Arg;
P3: Thr;
P4: Cys;
P5: Arg;
P6: Gly;
P7: $^D$Pro;
P8: Arg;
P9: Arg;
P10: 2-Nal;
P11: Cys;
P12: Tyr;
P13: Cit; and
P14: Lys(FHS);

or

P1: Tyr;
P2: Arg;
P3: Thr;
P4: Cys;
P5: Arg;
P6: Gly;
P7: $^D$Pro;
P8: Arg;

P9: Arg;
P10: 2-Nal;
P11: Cys;
P12: Tyr;
P13: Cit; and
P14: Lys(FITC);
or
P1: Tyr;
P2: Arg;
P3: Cit;
P4: Cys;
P5: Arg;
P6: Gly;
P7: $^D$Pro;
P8: Arg;
P9: Arg;
P10: Trp;
P11: Cys;
P12: Tyr;
P13: Lys(FHS); and
P14: Gln;
or
P1: Tyr;
P2: Lys(FHS);
P3: Cit;
P4: Cys;
P5: Arg;
P6: Gly;
P7: $^D$Pro;
P8: Arg;
P9: Arg;
P10: Trp;
P11: Cys;
P12: Tyr;
P13: Cit; and
P14: Gln;
or
P1: Tyr;
P2: Arg;
P3: Thr;
P4: Cys;
P5: Arg;
P6: Gly;
P7: Pro;
P8: Arg;
P9: Arg;
P10: 2-Nal;
P11: Cys;
P12: Tyr;
P13: Cit; and
P14: Lys(ALX);
or
P1: His;
P2: His;
P3: Gln;
P4: Cys;
P5: Ser;
P6: Ala;
P7: DPro;
P8: Phe;
P9: Arg;
P10: Tyr;
P11: Cys;
P12: Tyr;
P13: Gln; and
P14: Lys(FITC);
or
P1: Leu;
P2: His;
P3: Thr;
P4: Cys;
P5: Arg;
P6: Ala;
P7: $^D$Pro;
P8: Arg;
P9: Arg;
P10: Tyr;
P11: Cys;
P12: Tyr;
P13: Gln; and
P14: Lys(FITC);
or
P1: His;
P2: His;
P3: Tyr;
P4: Cys;
P5: Arg;
P6: Ala;
P7: $^D$Pro;
P8: Phe;
P9: Arg;
P10: Phe;
P11: Cys;
P12: Tyr;
P13: Gln; and
P14: Lys(FITC);
or
P1: Ser;
P2: His;
P3: Tyr;
P4: Cys;
P5: Arg;
P6: Ala;
P7: $^D$Pro;
P8: Phe;
P9: Arg;
P10: Phe;
P11: Cys;
P12: Tyr;
P13: Gln; and
P14: Lys(FITC);
or
P1: Tyr;
P2: Arg;
P3: Thr;
P4: Cys;
P5: Arg;
P6: Gly;
P7: $^D$Pro;
P8: Arg;
P9: Arg;
P10: Tyr;
P11: Cys;
P12: Tyr;
P13: Gln; and
P14: Lys(FITC);
or
P1: Tyr;
P2: Arg;
P3: Thr;
P4: Cys;
P5: Arg;
P6: Ala;
P7: $^D$Pro;

P8: Arg;
P9: Arg;
P10: Tyr;
P11: Cys;
P12: Tyr;
P13: Gln; and
P14: Lys(FITC);
or
P1: Tyr;
P2: Arg;
P3: Tyr;
P4: Cys;
P5: Arg;
P6: Ala;
P7: $^D$Pro;
P8: Phe;
P9: Arg;
P10: Phe;
P11: Cys;
P12: Tyr;
P13: Gln; and
P14: Lys(FITC);
or
P1: Tyr;
P2: His;
P3: Tyr;
P4: Cys;
P5: Ser;
P6: Ala;
P7: $^D$Pro;
P8: Phe;
P9: Arg;
P10: Tyr;
P11: Cys;
P12: Tyr;
P13: Gln; and
P14: Lys(FITC);
  with said Lys(Dsl) standing for L-N$^\epsilon$-Dansyl-lysine, Dpr(Dsl) standing for L-N$^\omega$-Dansyl-2,3-Diaminopropionic acid; Lys(FHS) standing for L-N$^\epsilon$-Fluorescin-5(6)-carboxamidocaproic-lysin; Lys(FITC) standing for L-N$^\epsilon$-Fluorescin-isomer I-lysine; and Lys(Alx) standing for L-N$^\epsilon$-Alexa Fluor 647-lysine;
  with the proviso that Cys at P4 and P11 can form a disulfide bridge; and
  with the further proviso that the molecule contains at least one Lys(Dsl) and/or Lys(FHS) and/or Lys(FITC), and/or Lys(Alx) and/or Dpr(Dsl) moiety;
and pharmaceutically acceptable salts thereof.

2. Enantiomers of the compound of formula I as defined in claim 1.

3. The compound according to claim 1 for use as therapeutically active substance and/or for diagnostic purpose.

4. The compound according to claim 3 wherein said use is as having CXCR4 antagonizing activity and/or anticancer activity and/or for diagnostic purposes as imaging agents.

5. A pharmaceutical composition comprising a compound according to claim 1 and a pharmaceutically inert carrier.

6. The composition according to claim 5 in a form suitable for oral, topical, transdermal, injection, buccal, transmucosal, pulmonary or inhalation administration.

7. The composition according to claim 5 in form of tablets, dragees, capsules, solutions, liquids, gels, plaster, creams, ointments, syrup, slurries, suspensions, spray, nebuliser or suppositories.

8. A diagnostic kit for labelling tumor tissues or cells, containing an effective amount of a compound according to claim 1.

9. A process for the manufacture of a compound according to claim 1 which process comprises
  (a) coupling an appropriately functionalized solid support with an appropriately N-protected derivative of that amino acid which in the desired end-product is in position 6, 7 or 8, any functional group which may be present in said N-protected amino acid derivative being likewise appropriately protected;
  (b) removing the N-protecting group from the product thus obtained;
  (c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;
  (d) removing the N-protecting group from the product thus obtained;
  (e) repeating steps (c) and (d) until the N-terminal amino acid residue has been introduced;
  (f) coupling the product thus obtained with a compound of the general formula

II wherein

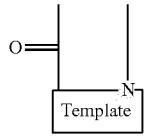

is as defined in claim 1 and X is an N-protecting group,
  (fa) coupling the product obtained in step (e) with an appropriately N-protected derivative of $^L$Pro or $^D$Pro;
  (fb) removing the N-protecting group from the product thus obtained; and
  (fc) coupling the product thus obtained with an appropriately N-protected derivative of $^D$Pro and, respectively, $^L$Pro;
  (g) removing the N-protecting group from the product obtained in step (f) or (fc);
  (h) coupling the product thus obtained with an appropriately N-protected derivative of that amino acid which in the desired end-product is in position 14, any functional group which may be present in said N-protected amino acid derivative being likewise appropriately protected;
  (i) removing the N-protecting group from the product thus obtained;
  (j) coupling the product thus obtained with an appropriately N-protected derivative of that amino acid which in the desired end-product is one position farther away from position 14, any functional group which may be present in said N-protected amino acid derivative being likewise appropriately protected;
(k) removing the N-protecting group from the product thus obtained;
(l) repeating steps (j) and (k) until all amino acid residues have been introduced;
(m) if desired, selectively deprotecting one or several protected functional group(s) present in the molecule and appropriately substituting the reactive group(s) thus liberated, if required by attaching one or several residues of a Dye;
(n) if desired, forming an interstrand linkages between the side-chains of Cys residues at positions P4 and P11;
(o) detaching the product thus obtained from the solid support;
(p) cyclizing the product cleaved from the solid support;
(q) removing any protecting groups present on functional groups of any members of the chain of amino acid residues and, if desired, any protecting group(s) which may in addition be present in the molecule; and
(r) if required, attaching one or several residues of a Dye; and
(s) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

10. A process for the manufacture of a compound according to claim 1 which process comprises
(a') coupling an appropriately functionalized solid support with a compound of the general formula

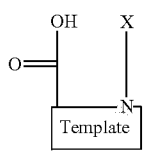

II wherein

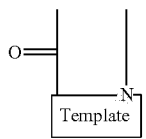

is as defined in claim 1 and X is an N-protecting group,
(a'a) coupling said appropriately functionalized solid support with an appropriately N-protected derivative of $^L$Pro or $^D$Pro;
(a'b) removing the N-protecting group from the product thus obtained; and
(a'c) coupling the product thus obtained with an appropriately N-protected derivative of $^D$Pro and, respectively, $^L$Pro;
(b') removing the N-protecting group from the product obtained in step (a'), or (a'c);
(c') coupling the product thus obtained with an appropriately N-protected derivative of that amino acid which in the desired end-product is in position 14, any functional group which may be present in said N-protected amino acid derivative being likewise appropriately protected;
(d') removing the N-protecting group from the product thus obtained;
(e') coupling the product thus obtained with an appropriately N-protected derivative of that amino acid which in the desired end-product is one position farther away, or from position 14, any functional group which may be present in said N-protected amino acid derivative being likewise appropriately protected;
(f) removing the N-protecting group from the product thus obtained;
(g') repeating steps (e') and (f) until all amino acid residues have been introduced;
(h') if desired, selectively deprotecting one or several protected functional group(s) present in the molecule and appropriately substituting the reactive group(s) thus liberated, if required by attaching one or several residues of a Dye;
(i') if desired, forming an interstrand linkages between the side-chains of Cys residues at opposite positions of the β-strand region;
(j') detaching the product thus obtained from the solid support;
(k') cyclizing the product cleaved from the solid support;
(l') removing any protecting groups present on functional groups of any members of the chain of amino acid residues and, if desired, any protecting group(s) which may in addition be present in the molecule;
(m') if required, attaching one or several residues of a Dye; and
(n') if desired, converting the product thus obtained into a pharmaceutically acceptable salt or pharmaceutically acceptable salt or converting a pharmaceutically acceptable, or unacceptable, salt thus obtained into the corresponding free compound of formula I or into a different, pharmaceutically acceptable, salt.

11. The process according to claim 9 wherein the process is modified for the manufacture of enantiomers of the compounds in which enantiomers of all chiral starting materials are used.

* * * * *

SEQUENCE LISTING

```
<160> NUMBER OF SEQ ID NOS: 18

<210> SEQ ID NO 1
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (3)..(3)
<223> OTHER INFORMATION: Cit
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (13)..(13)
<223> OTHER INFORMATION: Cit
<220> FEATURE:
<221> NAME/KEY: MOD_RES
<222> LOCATION: (14)..(14)
<223> OTHER INFORMATION: Lys(Dsl)

<400> SEQUENCE: 1

Tyr Arg Xaa Cys Arg Gly Xaa Arg Arg Trp Cys Tyr Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (3)..(3)
<223> OTHER INFORMATION: Cit
<220> FEATURE:
<221> NAME/KEY: MOD_RES
<222> LOCATION: (8)..(8)
<223> OTHER INFORMATION: Dpr(Dsl)
<220> FEATURE:
<221> NAME/KEY: MOD_RES
<222> LOCATION: (13)..(13)
<223> OTHER INFORMATION: Cit
```

```
<400> SEQUENCE: 2

Tyr Arg Xaa Cys Arg Gly Pro Xaa Arg Trp Cys Tyr Xaa Lys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (1)..(1)
<223> OTHER INFORMATION: Lys(FHS)
<220> FEATURE:
<221> NAME/KEY: MOD_RES
<222> LOCATION: (3)..(3)
<223> OTHER INFORMATION: Cit
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (13)..(13)
<223> OTHER INFORMATION: Cit

<400> SEQUENCE: 3

Xaa Arg Xaa Cys Arg Gly Xaa Arg Arg Trp Cys Tyr Xaa Gln
1               5                   10

<210> SEQ ID NO 4
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (3)..(3)
<223> OTHER INFORMATION: Cit
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (13)..(13)
<223> OTHER INFORMATION: Cit

<400> SEQUENCE: 4

Tyr Arg Xaa Cys Arg Gly Xaa Arg Arg Trp Cys Tyr Xaa Gln
1               5                   10

<210> SEQ ID NO 5
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (3)..(3)
<223> OTHER INFORMATION: Lys(FHS)
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
```

<222> LOCATION: (13)..(13)
<223> OTHER INFORMATION: Cit

<400> SEQUENCE: 5

Tyr Arg Xaa Cys Arg Gly Xaa Arg Arg Trp Cys Tyr Xaa Gln
1               5                   10

<210> SEQ ID NO 6
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (10)..(10)
<223> OTHER INFORMATION: 2-Nal
<220> FEATURE:
<221> NAME/KEY: MOD_RES
<222> LOCATION: (13)..(13)
<223> OTHER INFORMATION: Cit
<220> FEATURE:
<221> NAME/KEY: MOD_RES
<222> LOCATION: (14)..(14)
<223> OTHER INFORMATION: Lys(FHS)

<400> SEQUENCE: 6

Tyr Arg Thr Cys Arg Gly Xaa Arg Arg Xaa Cys Tyr Xaa Xaa
1               5                   10

<210> SEQ ID NO 7
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (10)..(10)
<223> OTHER INFORMATION: 2-Nal
<220> FEATURE:
<221> NAME/KEY: MOD_RES
<222> LOCATION: (13)..(13)
<223> OTHER INFORMATION: Cit
<220> FEATURE:
<221> NAME/KEY: MOD_RES
<222> LOCATION: (14)..(14)
<223> OTHER INFORMATION: Lys(FITC)

<400> SEQUENCE: 7

Tyr Arg Thr Cys Arg Gly Xaa Arg Arg Xaa Cys Tyr Xaa Xaa
1               5                   10

<210> SEQ ID NO 8
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (3)..(3)

```
<223> OTHER INFORMATION: Cit
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (13)..(13)
<223> OTHER INFORMATION: Lys(FHS)

<400> SEQUENCE: 8

Tyr Arg Xaa Cys Arg Gly Xaa Arg Arg Trp Cys Tyr Xaa Gln
1               5                   10

<210> SEQ ID NO 9
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (2)..(2)
<223> OTHER INFORMATION: Lys(FHS)
<220> FEATURE:
<221> NAME/KEY: MOD_RES
<222> LOCATION: (3)..(3)
<223> OTHER INFORMATION: Cit
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (13)..(13)
<223> OTHER INFORMATION: Cit

<400> SEQUENCE: 9

Tyr Xaa Xaa Cys Arg Gly Xaa Arg Arg Trp Cys Tyr Xaa Gln
1               5                   10

<210> SEQ ID NO 10
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (10)..(10)
<223> OTHER INFORMATION: 2-Nal
<220> FEATURE:
<221> NAME/KEY: MOD_RES
<222> LOCATION: (13)..(13)
<223> OTHER INFORMATION: Cit
<220> FEATURE:
<221> NAME/KEY: MOD_RES
<222> LOCATION: (14)..(14)
<223> OTHER INFORMATION: Lys(ALX)

<400> SEQUENCE: 10

Tyr Arg Thr Cys Arg Gly Pro Arg Arg Xaa Cys Tyr Xaa Xaa
1               5                   10

<210> SEQ ID NO 11
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
```

-continued

```
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (14)..(14)
<223> OTHER INFORMATION: Lys(FITC)

<400> SEQUENCE: 11

His His Gln Cys Ser Ala Xaa Phe Arg Tyr Cys Tyr Gln Xaa
1               5                   10

<210> SEQ ID NO 12
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (14)..(14)
<223> OTHER INFORMATION: Lys(FITC)

<400> SEQUENCE: 12

Leu His Thr Cys Arg Ala Xaa Arg Arg Tyr Cys Tyr Gln Xaa
1               5                   10

<210> SEQ ID NO 13
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (14)..(14)
<223> OTHER INFORMATION: Lys(FITC)

<400> SEQUENCE: 13

His His Tyr Cys Arg Ala Xaa Phe Arg Phe Cys Tyr Gln Xaa
1               5                   10

<210> SEQ ID NO 14
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (14)..(14)
<223> OTHER INFORMATION: Lys(FITC)

<400> SEQUENCE: 14

Ser His Tyr Cys Arg Ala Xaa Phe Arg Phe Cys Tyr Gln Xaa
1               5                   10
```

```
<210> SEQ ID NO 15
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (14)..(14)
<223> OTHER INFORMATION: Lys(FITC)

<400> SEQUENCE: 15

Tyr Arg Thr Cys Arg Gly Xaa Arg Arg Tyr Cys Tyr Gln Xaa
1               5                   10

<210> SEQ ID NO 16
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (14)..(14)
<223> OTHER INFORMATION: Lys(FITC)

<400> SEQUENCE: 16

Tyr Arg Thr Cys Arg Ala Xaa Arg Arg Tyr Cys Tyr Gln Xaa
1               5                   10

<210> SEQ ID NO 17
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (7)..(7)
<223> OTHER INFORMATION: DPro
<220> FEATURE:
<221> NAME/KEY: MOD_RES
<222> LOCATION: (14)..(14)
<223> OTHER INFORMATION: Lys(FITC)

<400> SEQUENCE: 17

Tyr Arg Tyr Cys Arg Ala Xaa Phe Arg Phe Cys Tyr Gln Xaa
1               5                   10

<210> SEQ ID NO 18
<211> LENGTH: 14
<212> TYPE: PRT
<213> ORGANISM: Artificial Sequence
<220> FEATURE:
<223> OTHER INFORMATION: dye conjugates of template-fixed
      peptidomimetics
<220> FEATURE:
<221> NAME/KEY: MOD_RES
<222> LOCATION: (7)..(7)
<223> OTHER INFORMATION: DPro
```

```
<220> FEATURE:
<221> NAME/KEY: MOD_RES
<222> LOCATION: (14)..(14)
<223> OTHER INFORMATION: Lys(FITC)

<400> SEQUENCE: 18

Tyr His Tyr Cys Ser Ala Xaa Phe Arg Tyr Cys Tyr Gln Xaa
1               5                   10
```